(12) United States Patent
Betzemeier et al.

(10) Patent No.: US 7,691,888 B2
(45) Date of Patent: Apr. 6, 2010

(54) THIAZOLYL-DIHYDRO-INDAZOLE

(75) Inventors: Bodo Betzemeier, Vienna (AT); Trixi Brandl, Warthausen (DE); Steffen Breitfelder, Assmannshardt (DE); Ralph Brueckner, Vienna (AT); Thomas Gerstberger, Vienna (AT); Michael Gmachl, Vienna (AT); Matthias Grauert, Biberach (DE); Frank Hilberg, Vienna (AT); Christoph Hoenke, Ingelheim (DE); Matthias Hoffmann, Mittelbiberach (DE); Maria Impagnatiello, Vienna (AT); Dirk Kessler, Vienna (AT); Christian Klein, Vienna (AT); Bernd Krist, Vienna (AT); Udo Maier, Senden (DE); Darryl McConnell, Vienna (AT); Charlotte Reither, Vienna (AT); Stefan Scheuerer, Warthausen (DE); Andreas Schoop, Vienna (AT); Norbert Schweifer, Vienna (AT); Oliver Simon, Vienna (AT); Martin Steegmaier, Vienna (AT); Steffen Steurer, Vienna (AT); Irene Waizenegger, Vienna (AT); Ulrike Weyer-Czernilofsky, Baden (AT); Andreas Zoephel, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 11/243,796

(22) Filed: Oct. 5, 2005

(65) Prior Publication Data

US 2006/0100254 A1 May 11, 2006

(30) Foreign Application Priority Data

| Oct. 7, 2004 | (DE) | 10 2004 048 877 |
| Feb. 9, 2005 | (DE) | 10 2005 005 813 |
| Aug. 5, 2005 | (EP) | 05107230 |

(51) Int. Cl.
*A61K 31/429* (2006.01)
*A61K 31/4162* (2006.01)
*C07D 513/02* (2006.01)
*C07D 417/14* (2006.01)

(52) U.S. Cl. ........................ 514/366; 514/405; 548/151; 548/359.5

(58) Field of Classification Search ................. 514/366, 514/406, 407, 405; 548/359.5, 151
See application file for complete search history.

(56) References Cited

U.S. PATENT DOCUMENTS

| 6,245,796 B1 * | 6/2001 | Maeno et al. ............... 514/403 |
| 2006/0106013 A1 * | 5/2006 | Breitfelder et al. ........ 514/232.5 |
| 2007/0001122 A1 * | 1/2007 | Gros D'aillon et al. 250/370.13 |
| 2007/0259855 A1 * | 11/2007 | Maier et al. ................. 514/215 |
| 2008/0081802 A1 * | 4/2008 | Mcconnell et al. ..... 514/210.21 |

FOREIGN PATENT DOCUMENTS

WO WO03035618 5/2003

OTHER PUBLICATIONS

P. Workman; "Inhibiting the phosphoinositide 3-kinase pathway for cancer treatment" 2004, vol. 32, part2, Biochemcial Society Transactions, Cancer Research UK Centre for Therapeutics, Institute of Cancer Research, Surrey, UK pp. 393-396.
Yardena Samuels, et al: "High frequency of mutation of the PIK3CA Gene in human cancers" Science (2004) vol. 304 p. 554.
Von Alfred Courtin; "Notiz zur Synthese von Alkyl, Cycloalkyl-und Aryl-3-amiophenylsulfonen" Helvetica Chimica Acta (1981) vol. 64 No. 177 pp. 1849-1853.
International Search Report PCT/EP2005/055021, May 10, 2005.
Beilstein Institute for Organic Chemistry; Frankfurt, Germany, XP002359147 (1988-2003).
Fravolini et al.; New Heterocyclic Ring Systems from a-Hydroxymethylene-ketones.III. Pyrazolo-Benzothiazoles and Thiazolo-Benzoisoxazoles; Gazzetta Chimica Italiana; 1973; No. 103; pp. 755-770.

* cited by examiner

*Primary Examiner*—Yong Chu
(74) *Attorney, Agent, or Firm*—Michael P. Morris; Mary-Ellen M. Devlin

(57) ABSTRACT

The present invention encompasses compounds of the general formula (1)

in which
$R^1$ to $R^3$ are defined as in claim 1, which are suitable for treating diseases which are characterized by excessive or anomalous cell proliferation, and their use for producing a pharmaceutical having the abovementioned properties.

6 Claims, No Drawings

THIAZOLYL-DIHYDRO-INDAZOLE

The present invention relates to novel thiazolyldihydroindazoles of the general formula (1)

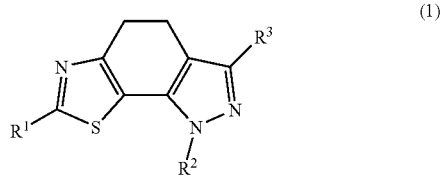

where the radicals $R^1$ to $R^3$ have the meanings given in the claims and the description, to their isomers, to processes for preparing these thiazolyl-dihydroindazoles, and to the use of the latter as pharmaceuticals.

BACKGROUND TO THE INVENTION

The phosphorylation of proteins and lipids is an important cellular regulation mechanism which plays a role in many different biological processes such as cell proliferation, differentiation, apoptosis, metabolism, inflammation, immune reactions and angiogenesis. More than 500 kinases are encoded in the human genome. In general, tyrosine protein kinases are stimulated by growth factors or other mitogenic signals and phosphorylate proteins which initiate rapid signal transmissions. Serine/threonine protein kinases mostly phosphorylate proteins which crosslink and amplify intracellular signals. Lipid kinases are likewise important switching sites in intracellular signal pathways, with these sites linking various biological processes.

A number of protein kinases have already proved to be suitable target molecules for therapeutic intervention in a variety of indications, e.g. cancer and inflammatory and autoimmune diseases. Since a high percentage of the genes involved in the development of cancer which have been identified thus far encode kinases, these enzymes are attractive target molecules for the therapy of cancer in particular.

Phosphatidylinositol 3-kinases (PI3 kinases) are a subfamily of the lipid kinases and catalyse the transfer of a phosphate radical to the 3' position of the inositol ring of phosphoinositides. They play a crucial role in a large number of cellular processes such as cell growth and differentiation processes, the regulation of cytoskeletal changes and the regulation of intracellular transport processes. The PI3 kinases can be subdivided into different classes on the basis of their in-vitro specificity for particular phosphoinositide substrates.

Among the members of the class I PI3 kinases, the α, β and δ PI3 kinases (class IA) are principally activated by receptor tyrosine kinases (RTKs) or soluble tyrosine kinases. On the other hand, the γ PI3 kinase (class IB) is principally activated by Gβγ subunits which are released from heterotrimeric G proteins following activation of heptahelical receptors. As a result of these differences in the coupling to cell surface receptors, in combination with a more or less restricted expression, the 4 class I PI3 kinases inevitably have very different tasks and functions in the intact organism.

Many independent findings indicate that class IA PI3 kinases are involved in uncontrolled processes of cell growth and differentiation. Thus, the first PI3 kinase activity which was detected was associated with the transforming activity of viral oncogenes such as the middle T antigen of polyoma viruses, Src tyrosine kinases or activated growth factors (Workman, Biochem Soc Trans. 2004; 32(Pt 2):393-6). Akt/PKB, which is activated directly by the lipid products of the class I PI3 kinases and in this way transmits the signals into the cell, is found to be hyperactive in many tumours such as breast cancer and ovarian or pancreatic carcinoma. In addition, it has recently been found that the PIK3 CA gene, which encodes the p110 subunit of PI3Kα, exhibits a high frequency of mutation in many tumour types such as colon, mammary and lung carcinomas, with some of the mutations being representatively characterized as being activating mutations (Samuels et al., Science 2004; 304(5670):554).

DETAILED DESCRIPTION OF THE INVENTION

It has now been found, surprisingly, that compounds of the general formula (1), in which the radicals $R^1$ to $R^3$ have the meanings given below, act as inhibitors of specific cell cycle kinases. Consequently, the compounds according to the invention can be used, for example, for treating diseases which are connected to the activity of specific cell cycle kinases and are characterized by excessive or anomalous cell proliferation.

The present invention relates to compounds of the general formula (1)

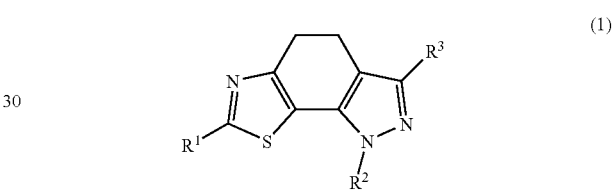

in which $R^1$ is selected from the group consisting of —NHR$^c$, —NHC(O)R$^c$, —NHC(O)OR$^c$, —NHC(O)NR$^c$R$^c$ and —NHC(O)SR$^c$;

$R^2$ is a radical which is optionally substituted by one or more $R^4$ and which is selected from the group consisting of $C_{1-6}$alkyl, $C_{3-8}$cycloalkyl, 3-8-membered heterocycloalkyl, $C_{6-10}$aryl and 5-10-membered heteroaryl;

$R^3$ is a radical which is optionally substituted by one or more $R^e$ and/or $R^f$ and is selected from the group consisting of $C_{6-10}$aryl and 5-10-membered heteroaryl;

$R^4$ is a radical selected from the group consisting of $R^a$, $R^b$ and $R^a$ which is substituted by one or more, identical or different, $R^c$ and/or $R^b$;

each $R^a$ is, independently of each other, selected from the group consisting of $C_{1-6}$alkyl, $C_{3-8}$cycloalkyl, $C_{4-11}$cycloalkylalkyl, $C_{6-10}$aryl, $C_{2-16}$arylalkyl, 2-6-membered heteroalkyl, 3-8-membered heterocycloalkyl, 4-14-membered heterocycloalkylalkyl, 5-10-membered heteroaryl and 6-16-membered heteroarylalkyl;

each $R^b$ is a suitable radical and in each case selected, independently of each other, from the group consisting of =O, —OR$^c$, $C_{1-3}$haloalkyloxy, —OCF$_3$, =S, —SR$^c$, =NR$^c$, =NOR$^c$, —NR$^c$R$^c$, halogen, —CF3, —CN, —NC, —OCN, —SCN, —NO, —NO$_2$, =N$_2$, —N$_3$, —S(O)R$^c$, —S(O)$_2$R$^c$, —S(O)$_2$OR$^c$, —S(O)NR$^c$R$^c$, —S(O)$_2$NR$^c$R$^c$, —OS(O)R$^c$, —OS(O)$_2$R$^c$, —OS(O)$_2$OR$^c$, —OS(O)$_2$NR$^c$R$^c$, —C(O)R$^c$, —C(O)OR$^c$, —C(O)NR$^c$R$^c$, —C(O)N(R$^g$)NR$^c$R$^c$, —C(O)N(R$^g$)OR$^c$, —CN(R$^g$)NR$^c$R$^c$, —OC(O)R$^c$, —OC(O)OR$^c$, —OC(O)NR$^c$R$^c$, —OCN(R$^g$)NR$^c$R$^c$, —N(R$^g$)C(O)R$^c$, —N(R$^g$)C(O)R$^c$, —N(R$^g$)C(S)R$^c$, —N(R$^g$)S(O)$_2$R$^c$, —N(R$^g$)S(O)$_2$NR$^c$R$^c$, —N[S(O)$_2$]$_2$R$^c$, —N(R$^g$)C(O)OR$^c$, —N(R$^g$)C(O)NR$^c$R$^c$, and —N(R$^g$)CN(R$^g$)NR$^c$R$^c$;

each R$^c$ is, independently of each other, hydrogen or a radical which is optionally substituted by one or more, identical or different, R$^d$ and/or R$^e$ and which is selected from the group consisting of C$_{1-6}$alkyl, C$_{3-8}$cycloalkyl, C$_{4-11}$cycloalkylalkyl, C$_{6-10}$aryl, C$_{7-16}$arylalkyl, 2-6-membered heteroalkyl, 3-8-membered heterocycloalkyl, 4-14-membered heterocycloalkylalkyl, 5-10-membered heteroaryl and 6-16-membered heteroarylalkyl, each R$^d$ is, independently of each other, hydrogen or a radical which is optionally substituted by one or more, identical or different, R$^e$ and/or R$^f$ and which is selected from the group consisting of C$_{1-6}$alkyl, C$_{3-8}$cycloalkyl, C$_{4-11}$cycloalkylalkyl, C$_{6-10}$aryl, C$_{2-16}$arylalkyl, 2-6-membered heteroalkyl, 3-8-membered heterocycloalkyl, 4-14-membered heterocycloalkylalkyl, 5-10-membered heteroaryl and 6-16-membered heteroarylalkyl, each R$^e$ is a suitable radical and in each case selected, independently of each other, from the group consisting of =O, —OR$^f$, C$_{1-3}$haloalkyloxy, —OCF$_3$, =S, —SR$^f$, =NR$^f$, =NOR$^f$, —NR$^f$R$^f$, halogen, —CF3, —CN, —NC, —OCN, —SCN, —NO, —NO$_2$, =N$_2$, —N$_3$, —S(O)R$^f$, —S(O)$_2$R$^f$, —S(O)$_2$OR$^f$, —S(O)NR$^f$R$^f$, —S(O)$_2$NR$^f$R$^f$, —OS(O)R$^f$, —OS(O)$_2$R$^f$, —OS(O)$_2$OR$^f$, —OS(O)$_2$NR$^f$R$^f$, —C(O)R$^f$, —C(O)OR$^f$, —C(O)NR$^f$R$^f$, —CN(R$^g$)NR$^f$R$^f$, —OC(O)R$^f$, —OC(O)OR$^f$, —OC(O)NR$^f$R$^f$, —OCN(R$^g$)NR$^f$R$^f$, —N(R$^g$)C(O)R$^f$, —N(R$^g$)C(S)R$^f$, —N(R$^g$)S(O)$_2$R$^f$, —N(R$^g$)C(O)OR$^f$, —N(R$^g$)C(O)NR$^f$R$^f$, and —N(R$^g$)CN(R$^g$)NR$^f$R$^f$;

each R$^f$ is, independently of each other, hydrogen or a radical which is optionally substituted by one or more, identical or different, R$^g$ and which is selected from the group consisting of C$_{1-6}$alkyl, C$_{3-8}$cycloalkyl, C$_{4-11}$cycloalkylalkyl, C$_{6-10}$aryl, C$_{7-16}$arylalkyl, 2-6-membered heteroalkyl, 3-8-membered heterocycloalkyl, 4-14-membered heterocycloalkylalkyl, 5-10-membered heteroaryl and 6-16-membered heteroarylalkyl, each R$^g$ is, independently of each other, hydrogen, C$_{1-6}$alkyl, C$_{3-8}$cycloalkyl, C$_{4-11}$cycloalkylalkyl, C$_{6-10}$aryl, C$_{7-16}$arylalkyl, 2-6-membered heteroalkyl, 3-8-membered heterocycloalkyl, 4-14-membered heterocycloalkylalkyl, 5-10-membered heteroaryl and 6-16-membered heteroarylalkyl, where appropriate in the form of their tautomers, their racemates, their enantiomers, their diastereomers and their mixtures, as well as, where appropriate, their pharmacologically harmless acid addition salts.

One aspect of the invention relates to compounds of the general formula (1) where R$^3$ is a radical which is selected from the group consisting of phenyl, furyl, pyridyl, pyrimidinyl and pyrazinyl, where appropriate substituted by one or more R$^4$.

Another aspect of the invention relates to compounds of the general formula (1) where R$^3$ is pyridyl.

Another aspect of the invention relates to compounds of the general formula (1) where R$^1$ is —NHC(O)R$^c$.

Another aspect of the invention relates to compounds of the general formula (1) where R$^1$ is —NHC(O)CH$_3$.

One aspect of the invention relates to compounds of formula (A)

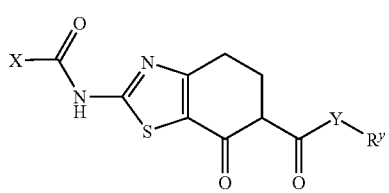

where

X is —CH$_3$, —OR$^4$ or —SR$^4$, and

Y is phenyl, 5-10-membered heteroaryl or the group —C(O)O, and

R$^y$ is hydrogen, —NO$_2$ or C$_{1-6}$alkyl and R$^4$ is defined as above.

Another aspect of the invention relates to compounds of the general formula (A) where R$^4$ is —C$_{1-6}$alkyl.

Another aspect of the invention relates to the use of compounds of the formula (A) as synthesis intermediates.

One aspect of the invention relates to compounds of the general formula (1), or their pharmaceutically active salts, as pharmaceuticals.

One aspect of the invention relates to the use of compounds of the general formula (1), or their pharmaceutically active salts, for producing a pharmaceutical having an antiproliferative effect.

One aspect of the invention relates to a pharmaceutical composition which comprises, as the active compound, one or more compounds of the general formula (1) or their physiologically tolerated salts, where appropriate in combination with customary auxiliary substances and/or carrier substances.

Another aspect of the invention relates to the use of compounds of the general formula (1) for producing a pharmaceutical for treating and/or preventing cancer.

One aspect of the invention relates to a pharmaceutical preparation which comprises a compound of the general formula (1) and at least one further cytostatic or cytotoxic active substance which differs from formula (1), where appropriate in the form of their tautomers, their racemates, their enantiomers, their diastereomers and their mixtures, as well as, where appropriate, their pharmacologically harmless acid addition salts.

DEFINITIONS

As used herein, the following definitions apply unless otherwise described.

Alkyl substituents are in each case to be understood as being saturated, unsaturated, straight-chain or branched aliphatic hydrocarbon radicals (alkyl radicals) and comprise both saturated alkyl radicals and unsaturated alkenyl and alkynyl radicals. Alkenyl substituents are in each case straight-chain or branched, unsaturated alkyl radicals which possess at least one double bond. Alkynyl substituents are in each case to be understood as being straight-chain or branched, unsaturated alkyl radicals which possess at least one triple bond.

Heteroalkyl represents straight-chain or branched aliphatic hydrocarbon chains which are interrupted by from 1 to 3 heteroatoms, with it being possible for each of the available carbon and nitrogen atoms in the heteroalkyl chain to be optionally substituted, in each case independently of each other, and with the heteroatoms being selected, in each case independently of each other, from the group consisting of O, N and S (e.g. dimethylaminomethyl, dimethylaminoethyl, dimethylaminopropyl, diethylaminomethyl, diethylaminoethyl, diethylaminopropyl, 2-diisopropylaminoethyl, bis-2-methoxyethylamino, [2-(dimethylaminoethyl)-ethylamino]methyl, 3-[2-(dimethylaminoethyl)ethylamino]propyl, hydroxymethyl, 2-hydroxyethyl, 3-hydroxypropyl, methoxy, ethoxy, propoxy, methoxymethyl and 2-methoxyethyl).

Haloalkyl refers to alkyl radicals in which one or more hydrogen atom(s) has/have been replaced by halogen atoms. Haloalkyl includes both saturated alkyl radicals and unsaturated alkenyl and alkynyl radicals, such as —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —$CF=CF_2$, —$CCl=CH_2$, —$CBr=CH_2$, —$CI=CH_2$, —$CC≡CF_3$, —$CHFCH_2CH_3$ and —$CHFCH_2CF_3$.

Halogen refers to fluorine, chlorine, bromine and/or iodine atoms.

Cycloalkyl is to be understood as being a monocyclic or bicyclic ring where the ring system can be a saturated ring, or else an unsaturated, nonaromatic ring, which can, where appropriate, also contain double bonds, such as cyclopropyl, cyclopropenyl, cyclobutyl, cyclobutenyl, cyclopentyl, cyclopentenyl, cyclohexyl, cyclohexenyl, norbornyl and norbornenyl.

Cycloalkylalkyl comprises a noncyclic alkyl group in which a hydrogen atom which is bonded to a carbon atom, usually to a terminal C atom, has been replaced by a cycloalkyl group.

Aryl refers to monocyclic or bicyclic rings having 6-12 carbon atoms, such as phenyl and naphthyl.

Arylalkyl comprises a noncyclic alkyl group in which a hydrogen atom which is bonded to a carbon atom, usually to a terminal C atom, has been replaced by an aryl group.

Heteroaryl is to be understood as meaning monocyclic or bicyclic rings which contain one or more, identical or different heteroatoms, such as nitrogen, sulphur or oxygen atoms, in place of one or more carbon atoms. Those which may be mentioned by way of example are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl. Examples of bicyclic heteroaryl radicals are indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl and benzotriazinyl, indolizinyl, oxazolopyridyl, imidazopyridyl, naphthyridinyl, indolinyl, isochromanyl, chromanyl, tetrahydroisoquinolinyl, isoindolinyl, isobenzotetrahydrofuryl, isobenzotetrahydrothienyl, isobenzothienyl, benzoxazolyl, pyridopyridyl, benzotetrahydrofuryl, benzotetrahydrothienyl, purinyl, benzodioxolyl, triazinyl, phenoxazinyl, phenothiazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridyl-N-oxide tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl-N-oxide, pyrimidinyl-N-oxide, pyridazinyl-N-oxide, pyrazinyl-N-oxide, quinolinyl-N-oxide, indolyl-N-oxide, indolinyl-N-oxide, isoquinolyl-N-oxide, quinazolinyl-N-oxide, quinoxalinyl-N-oxide, phthalazinyl-N-oxide, imidazolyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-N-oxide, oxadiazolyl-N-oxide, thiadiazolyl-N-oxide, triazolyl-N-oxide, tetrazolyl-N-oxide, benzothiopyranyl-S-oxide and benzothiopyranyl-S,S-dioxide.

Heteroarylalkyl comprises a noncyclic alkyl group in which a hydrogen atom which is bonded to a carbon atom, usually to a terminal C atom, has been replaced by a heteroaryl group.

Heterocycloalkyl refers to saturated or unsaturated, non-aromatic monocyclic, bicyclic or bridged bicyclic rings which comprise 3-12 carbon atoms and which carry heteroatoms, such as nitrogen, oxygen or sulphur, in place of one or more carbon atoms. Examples of these heterocycloalkyl radicals are tetrahydrofuryl, pyrrolidinyl, pyrrolinyl, imidazolidinyl, imidazolinyl, pyrazolidinyl, pyrazolinyl, piperidinyl, piperazinyl, indolinyl, isoindolinyl, morpholinyl, thiomorpholinyl, homomorpholinyl, homopiperidinyl, homopiperazinyl, homothiomorpholinyl, thiomorpholinyl-5-oxide, thiomorpholinyl-S,S-dioxide, tetrahydropyranyl, tetrahydrothienyl, homothiomorpholinyl-S,S-dioxide, oxazolidinonyl, dihydropyrazolyl, dihydropyrrolyl, dihydropyrazinyl, dihydropyridyl, dihydropyrimidinyl, dihydrofuryl, dihydropyranyl, tetrahydrothienyl-5-oxide, tetrahydrothienyl-S,S-dioxide, homothiomorpholinyl-5-oxide, 2-oxa-5-azabicyclo[2.2.1]heptane, 8-oxa-3-azabicyclo[3.2.1]octane, 3,8-diazabicyclo-[3.2.1]octane, 2,5-diazabicyclo[2.2.1]heptane, 3,8-diazabicyclo[3.2.1]octane, 3,9-diazabicyclo[4.2.1]nonane and 2,6-diazabicyclo[3.2.2]nonane.

Heterocycloalkylalkyl refers to a noncyclic alkyl group in which a hydrogen atom which is bonded to a carbon atom, usually to a terminal C atom, has been replaced by a heterocycloalkyl group.

The following examples illustrate the present invention without, however, limiting its scope.

Synthesizing the Reagents

R-1)
cis-1-Methylamino-4-(pyrrolidin-1-yl)cyclohexane

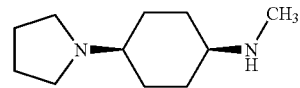

R-1a) tert-Butyl
cis-4-(pyrrolidin-1-yl)cyclohexanecarbamate

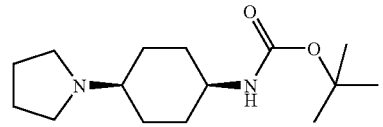

25 mg of potassium hydrogen carbonate are added to a solution of tert-butyl cis-4-aminocyclohexanecarbamate (10 g, 46 mmol) and 1,4-dibromobutane (12.1 g, 56 mmol) in 400 ml of DMF, and the mixture is stirred at RT for 24 h. The reaction mixture is then evaporated and the residue is taken up in diethyl ether; this solution is washed with water. The organic phase is dried and evaporated in vacuo. Yield: 12 g.

R-1b) tert-Butyl N-methyl-cis-4-(pyrrolidin-1-yl)-cyclohexanecarbamate

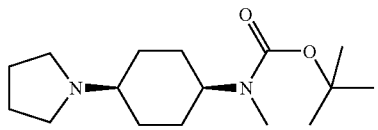

R-1a (5 g, 18 mmol) is dissolved in 20 ml of N,N-dimethylacetamide and this solution is added, at 37° C., to a suspension of sodium hydride (60% in liquid paraffin, 0.8 g, 20 mmol) in 20 ml of N,N-dimethylacetamide such that the temperature does not exceed 48° C. After the foam formation has come to an end, methyl iodide (2.9 g, 20 mmol) is added and the mixture is stirred at RT for 10 min. Ethyl acetate is added to the reaction mixture and the whole is washed with water. The organic phase is then treated with oxalic acid and washed with ethyl acetate. After that, the mixture is made alkaline with potassium hydrogen carbonate and extracted with ethyl acetate. The organic phases are evaporated and the residue is reacted without further purification. Yield: 1.4 g.

R-1b (1.4 g, 5 mmol) is dissolved in 50 ml of dichloromethane after which 25 ml of trifluoroacetic acid are added and the whole is stirred at RT for 4 h. After the reaction mixture has been evaporated, the desired product is precipitated as the dihydrochloride using hydrochloric acid (1 N in diethyl ether). Yield: 1 g R-2) trans-1-Amino-4-(8-oxa-3-azabicyclo[3.2.1]oct-3-yl)cyclohexane

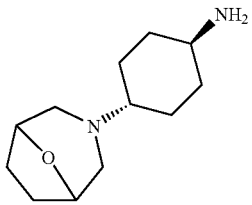

Triethylamine (21 g, 0.21 mol), benzyl trans-4-aminocyclohexylcarbamate (24.8 g, 0.1 mol) and a catalytic quantity of DMAP are added consecutively to a solution of 2,5-bis(p-tosyloxymethyl)tetrahydrofuran (44 g, 0.1 mol) in 440 ml of toluene. The reaction mixture is heated under reflux for 6 d. After cooling down, the organic phase is decanted off from the insoluble resin and the residue is purified chromatographically. The intermediate which is obtained in this way is suspended in 300 ml of methanol in an autoclave, after which 37 ml of hydrochloric acid (6 N in isopropanol) and 6 g of palladium on active charcoal are added. The reaction mixture is stirred under a hydrogen atmosphere (50 bar) at RT for 15 h. After filtering through Celite®, the filtrate is evaporated and the residue is taken up in hot ethyl acetate; 37 ml of hydrochloric acid (6 N in isopropanol) are added to this solution. On cooling, the desired product precipitates as the hydrochloride salt, which is filtered and dried.

R-3) 1-Amino-4-(methylpropylamino)cyclohexane

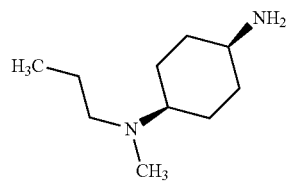

R-3a) tert-Butyl cis-4-(2,2,2-trifluoroacetylamino)cyclohexanecarbamate

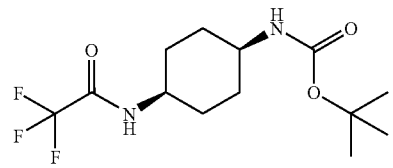

A solution of tert-butyl cis-4-aminocyclohexanecarbamate (22.1 g, 103 mmol) and methyl trifluoroacetate (11 ml, 110 mmol) in 110 ml of methanol is stirred at RT for 4 h. After the reaction mixture has been cooled down to 0° C., the precipitate is filtered off, washed with diethyl ether and dried. Yield: 17.6 g.

R-3b) ten-Butyl cis-4-methyl-(2,2,2-trifluoroacetyl)aminocyclohexanecarbamate

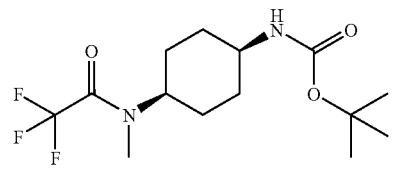

Sodium hydride (60% in liquid paraffin, 1.3 g, 32 mmol) is added, at RT and under a nitrogen atmosphere, to a suspension of R-3a (8.3 g, 27 mmol) in 100 ml of N,N-dimethylacetamide. After 20 min, methyl iodide (4.5 g, 32 mmol) is added and the mixture is stirred at RT for 15 h. Following hydrolysis with 800 ml of ice water, the precipitate is filtered off and washed with water and petroleum ether. The residue is recrystallized from 200 ml of diisopropyl ether to which 10 ml of acetonitrile have been added. Yield: 11 g.

R-3c) tert-Butyl cis-4-methylaminocyclohexanecarbamate

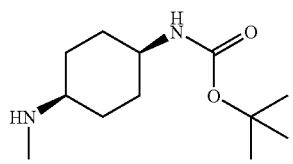

In order to eliminate the trifluoroacetate group, 117 ml of sodium hydroxide solution (2 N) are added to R-3b (39.7 g, 123 mmol) in 536 ml of methanol and the mixture is stirred at RT for 5 h. The reaction mixture is evaporated and the residue is extracted by shaking with water and ethyl acetate. The organic phase is dried, filtered and evaporated in vacuo. Yield: 28.4 g.

R-3d) tert-Butyl cis-4-(methylpropylamino)cyclohexanecarbamate

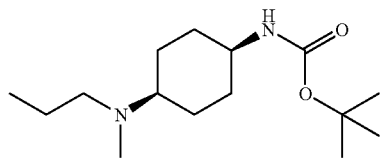

Triethylamine (0.98 g, 9.7 mmol) and n-propyl bromide (1.2 g, 9.7 mmol) are added to a solution of R-3c (2 g, 8.8 mmol) in 5 ml of acetonitrile and the mixture is stirred at 60° C. for 3 h in a pressure tube. The reaction mixture is then evaporated and the residue is extracted by shaking with water and ethyl acetate. Yield: 1 g.

The BOC protecting group is eliminated, in analogy with the preparation of R-1, using R-3d (1 g, 3.7 mmol), 20 ml of trifluoroacetic acid and 20 ml of dichloromethane. Yield: 0.6 g R-4) Cyclopropylpiperidin-4-ylamine

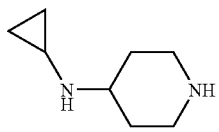

A solution of 1-tert-butoxycarbonylpiperidin-4-one (1 g, 5 mmol) and cyclopropylamine (352 μl) in 15 ml of 1,2-dichloroethane is stirred at RT for 20 min after which sodium triacetoxyborohydride (1.6 g, 7 mmol) and 0.3 ml of acetic acid are added. After having been stirred at RT for 15 h, the reaction mixture is hydrolysed with a saturated solution of sodium hydrogen carbonate and extracted with 2×50 ml of dichloromethane. The combined organic phases are washed with a saturated solution of sodium chloride, dried, filtered and evaporated. The residue is taken up in 4 ml of diethyl ether after which 8 ml of hydrochloric acid (4 N in dioxane) are added. After stirring at RT for 15 h, the precipitate is filtered off and washed with diethyl ether. The desired product is obtained as hydrochloride. Yield: 0.96 g R-5) 1-Cyclopentylpiperidine-4-carboxylic acid

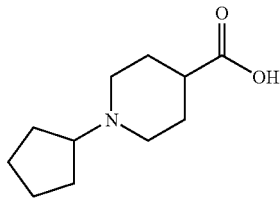

Catalytic quantities of p-toluenesulphonic acid (750 mg) and 12.5 ml of glacial acetic acid are added to a solution of ethyl piperidine-4-carboxylate (22.9 g, 145 mmol) and cyclo-pentanone (13.5 g, 160 mmol) in 400 ml of THF. After stirring at RT for 30 min, sodium triacetoxyborohydride (42 g, 190 mmol) is added in portions. The reaction mixture is stirred at RT for 15 h and, after evaporating, the residue is extracted by shaking with sodium carbonate solution and dichloromethane. The organic phase is dried, filtered and evaporated. Yield: 32 g of ethyl 1-cyclopentylpiperidine-4-carboxylate. The intermediate compound (1 g, 4.4 mmol) is then hydrolysed, in 10 ml of EtOH, at 80° C. for 15 h with 10 ml of NaOH (5 N). After having been cooled down, the reaction mixture is acidified and the resulting precipitate is filtered off.

R-6) cis-4-(Pyrrolidin-1-yl)cyclohexanecarboxylic acid

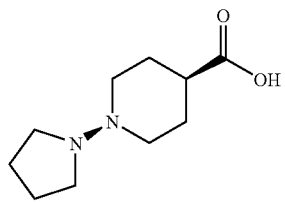

1,4-Dichlorobutane (2.3 ml, 21 mmol), potassium carbonate (12.6 g, 91 mmol) and potassium iodide (400 mg) are added to a solution of methyl cis-4-aminocyclo-hexanecarboxylate hydrochloride (4 g, 21 mmol) in 32 ml of DMF and the mixture is stirred at 100° C. for 6 h and then at RT for 3 d. The reaction mixture is diluted with 200 ml of water, neutralized with glacial acetic acid, saturated with sodium chloride and extracted with dichloromethane. The organic phases are dried, filtered and evaporated. Yield: 3.8 g of methyl cis-4-(pyrrolidin-1-yl)cyclohexanecarboxylate. The intermediate is then stirred, in 10 ml of methanol, with 25 ml of sodium hydroxide solution (1 N) at RT for 15 h. After the methanol has been removed in vacuo, the reaction mixture is adjusted to pH 6 with hydrochloric acid and evaporated further. The residue is taken up in methanol and purified by filtration through silica gel. Yield: 3.5 g.

R-7) 3-Morpholin-4-ylcyclobutylamine

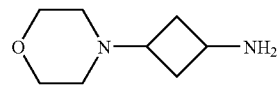

R-7a) 3-tert-Butoxycarbonylaminocyclobutyl toluene-4-sulphonate

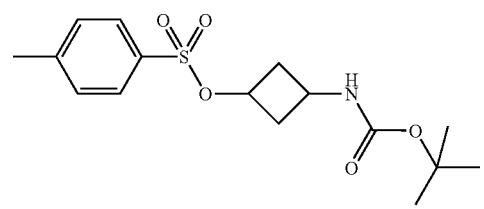

A solution of toluene-4-sulphonyl chloride (20.5 g, 0.105 mol) in 150 ml of chloroform is added dropwise, at 0° C., to a solution of 3-tert-butoxycarbonyl-aminocyclobutanol (18.7 g, 0.1 mol) and triethylamine (12.1 g, 0.12 mol) in 500 ml of chloroform and the mixture is then warmed to RT. The organic phase is washed consecutively with water, dilute hydrochloric acid, sodium hydrogen carbonate solution and once again with water before it is dried, filtered and evaporated.

R-7b) 1-Morpholin-1-yl-3-tert-butoxycarbony-lamino-cyclobutane

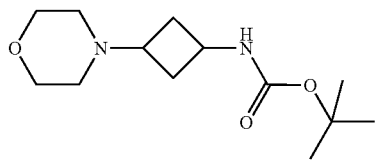

R-7a (34 g, 0.1 mol) is dissolved in 750 ml of morpholine after which a catalytic quantity of DMAP is added and the mixture is stirred at 100° C. for 3 h under an argon atmosphere. The reaction mixture is then evaporated in vacuo, after which the residue is coevaporated with 100 ml of toluene and then taken up in 500 ml of ethyl acetate. The organic phase is washed with a saturated solution of sodium hydrogen carbonate, dried, filtered and evaporated, with the desired compound, which is used without any further purification, being obtained. 260 ml of hydrochloric acid (2 N) are added to R-7b (25.6 g, 0.1 mol) and the mixture is stirred at 40° C. for 2 h. After the reaction has been completed, the reaction mixture is made alkaline with methanolic ammonia solution, filtered and evaporated. The residue is then recrystallized from ethanol, with R-7 being obtained.

H-1) Methyl 4-hydrazino-3-methylbenzoate

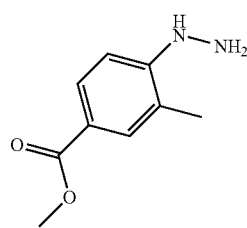

50 ml of conc. hydrochloric acid are added to methyl 4-amino-3-methylbenzoate (10 g, 61 mmol) and the mixture is cooled down to −15° C. A solution of sodium nitrite (6.3 g, 91 mmol) in 50 ml of water is added dropwise in such a way that the temperature does not exceed −5° C. After stirring at −10° C. for 4 h, a solution of tin(II) chloride dihydrate in 50 ml of conc. hydrochloric acid is added dropwise to the suspension, with the reaction temperature not exceeding −5° C. The viscous suspension is stirred at RT for 15 h before it is adjusted to pH 14 with 200 ml of sodium hydroxide solution (10 N). The reaction mixture is filtered through kieselguhr and Extrelut® (60 g) and rinsed with 2 l of chloroform. The organic phase which is obtained is washed with water (2×200 ml), dried over sodium sulphate and evaporated in vacuo. The residue is stirred up with 120 ml of petroleum ether and filtered. Yield: 6.3 g H-2) Methyl 4-hydrazino-3-fluorobenzoate

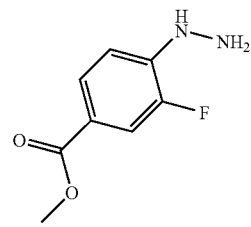

The desired compound is obtained in analogy with the preparation of H-1, starting from methyl 4-amino-3-fluorobenzoate (3.9 g, 23 mmol), sodium nitrite (2.4 g, 34 mmol) and tin(II) chloride dihydrate (20.8 g, 92 mmol). Yield: 3.4 g H-3) 3-Iodophenylhydrazine

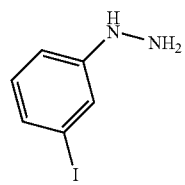

The desired compound is thus obtained, as hydrochloride, in analogy with the preparation of H-1, starting from 3-iodoaniline (2.75 g, 22.8 mmol), sodium nitrite (1.58 g, 22.8 mmol) and tin(II) chloride dihydrate (15.4 g, 68.5 mmol). Yield: 3.55 g H-4) 3-Hydrazinophenylacetic acid

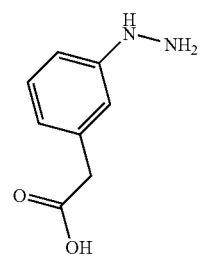

The desired compound is obtained in analogy with the preparation of H-1, starting from 3-aminophenylacetic acid (2 g, 13.2 mmol), sodium nitrite (0.91 g, 13.2 mmol) and tin(II) chloride dihydrate (6.1 g, 26.4 mmol).

H-5) Piperidin-4-yl-hydrazine

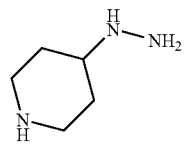

4-Oxopiperidine-1-tert-butoxycarbonyl (500 mg, 2.5 mmol) is dissolved, under an argon atmosphere, in hexane, after which tert-butyl carbazate (332 mg, 2.5 mmol) is added. After 20 min of heating under reflux, the reaction mixture is cooled down and the resulting precipitate is filtered off. Borane-THF complex (1 M in THF; 2.2 ml) is added to 4-(tert-butoxycarbonylhydrazono)piperidine-1-tert-butoxycarbonyl (707 mg, 2.3 mmol) and the mixture is stirred at RT for 1 h. The desired product is then precipitated, as hydrochloride, with 6 ml of hydrochloric acid (4 N in dioxane), and filtered off.

H-6) Ethyl 4-hydrazinocyclohexanecarboxylate

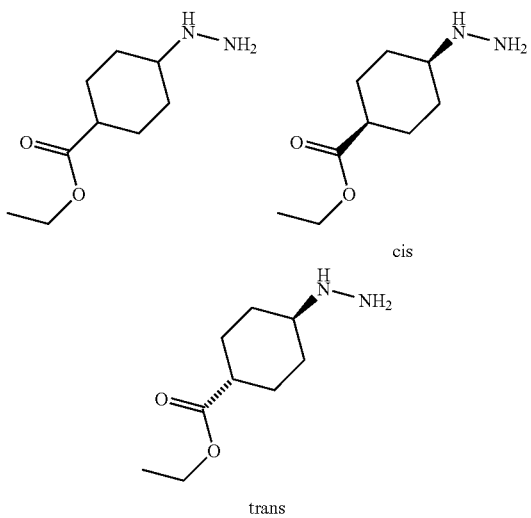

The desired product is obtained, as a cis/trans mixture, in analogy with the preparation of H-5, starting from ethyl 4-oxocyclohexanecarboxylate (4.5 g, 26.4 mmol), tert-butyl carbazate (3.5 g, 26.4 mmol) and borane-THF complex (1 M in THF; 26.5 ml); the cis/trans mixture is then subjected to further use without any additional purification or separated chromatographically on silica gel using 0-33% ethyl acetate in cyclohexane.

Yield: cis: 2.2 g
trans: 2.6 g

H-7) 2-Chloro-4-hydroxymethylphenylhydrazine

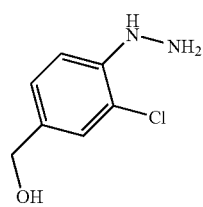

Diisobutylaluminium hydride (1M in toluene, 190 ml) is added dropwise, under a nitrogen atmosphere and at −73° C., to a solution of methyl 3-chloro-4-hydrazinobenzoate (9.5 g, 47 mmol) in 1 l of toluene in such a way that the temperature does not rise above −70° C. The reaction mixture is stirred at −73° C. for 30 min and then warmed to −5° C. Following hydrolysis with 500 ml of water, the precipitate is filtered off and washed with ethyl acetate (5×500 ml). The organic phase is evaporated, after which the residue is taken up in a little ethyl acetate and precipitated with petroleum ether/diethyl ether and filtered off. The solid which is obtained in this way is purified chromatographically on silica gel using cyclohexane/ethyl acetate. Yield: 2.9 g H-8) Methyl 3-hydrazinomethylbenzoate

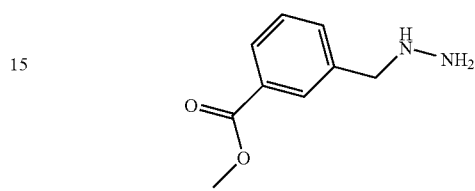

A solution of 3 g of methyl 3-bromomethylbenzoate (13 mmol), 2.6 g of tert-butoxycarbonylhydrazine (19 mmol) and 3.1 g of potassium carbonate (23 mmol) in 30 ml of DMF is stirred at RT for 24 h. After water has been added, the reaction mixture is extracted with dichloromethane. The organic phase is dried, filtered and evaporated, and the residue is purified chromatographically. The BOC protecting group is then eliminated using 30 ml of hydrochloric acid (4 M in dioxane). Yield: 1.25 g H-9) (4-Trifluoromethylpyridin-3-yl)hydrazine

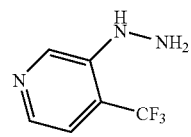

The desired compound is obtained in analogy with the preparation of H-1, starting from 3-amino-4-trifluoromethylpyridine (5.1 g, 31 mmol), sodium nitrite (2.2 g, 31 mmol) and tin(II) chloride dihydrate (21.6 g, 94 mmol). Yield: 3.8 g H-10) N-(4-Hydrazinophenyl)-N-methylacetamide

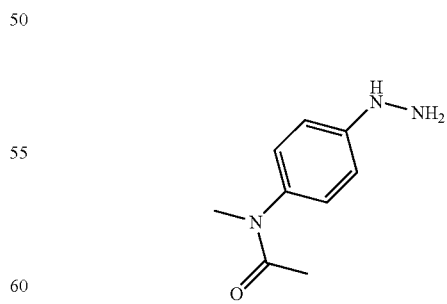

The desired compound is obtained in analogy with the preparation of H-1, starting from N-(4-aminophenyl)-N-methylacetamide (0.4 g, 2.4 mmol), sodium nitrite (0.2 g, 2.7 mmol) and tin(II) chloride dihydrate (1.6 g, 7.3 mmol). Yield: 0.2 g H-11) (4-Morpholin-4-ylmethylphenyl)hydrazine

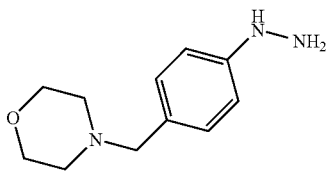

The desired compound is obtained in analogy with the preparation of H-1, starting from 4-morpholin-4-ylmethylphenylamine (1.1 g, 5 mmol), sodium nitrite (0.3 g, 5 mmol) and tin(II) chloride dihydrate (5.8 g, 25 mmol). Yield: 0.3 g H-12) Pyrrolidin-3-ylhydrazine

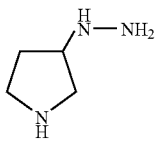

The desired compound is obtained, as the hydrochloride, in analogy with the preparation of H-5, starting from tert-butyl 3-oxopyrrolidine-1-carboxylate.

H-13) [3-(2-Methylpropane-1-sulphonyl)phenyl]hydrazine

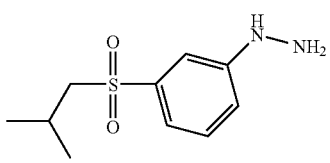

The desired compound is obtained, as the hydrochloride, in analogy with the preparation of H-1, starting from 3-(2-methylpropane-1-sulphonyl)phenylamine (1.5 g, 7 mmol), which can be prepared in analogy with the literature (A. Courtin, Helv. Chim. Acta 1981, 64, 1849), sodium nitrite (0.5 g, 7 mmol) and tin(II) chloride dihydrate (4.9 g, 21 mmol). Yield: 1.8 g H-14) 4-Hydrazinophenylacetonitrile

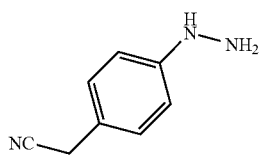

The desired compound is obtained, as the hydrochloride, in analogy with the preparation of H-1, starting from 4-aminophenylacetonitrile (5 g 37.8 mmol), sodium nitrite (2.6 g, 37.4 mmol) and tin(II) chloride dihydrate (25.8 g, 112 mmol). Yield: 5.4 g H-15) (1-Methyl-1H-indazol-5-yl)hydrazine

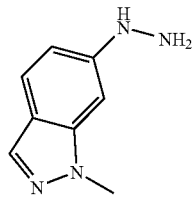

The desired compound is obtained, as the hydrochloride, in analogy with the preparation of H-1, starting from 1-methyl-1H-indazol-5-ylamine (0.9 g 6 mmol), sodium nitrite (0.44 g, 6.4 mmol) and tin(II) chloride dihydrate (2.8 g, 12.6 mmol). Yield: 1.2 g Synthesizing the Intermediate Compounds Z-1) N-[7-Oxo-6-(pyrimidine-5-carbonyl)-4,5,6,7-tetrahydrobenzothiazol-2-yl]acetamide

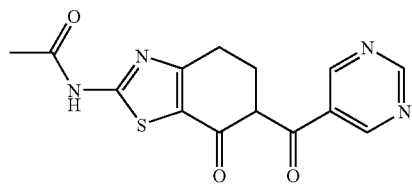

A solution of 10 g (48 mmol) of Z-6 in 1 l of THF is cooled to −40° C. after which 143 ml (143 mmol) of Li-HMDS (1 N in THF) are added dropwise in such a way that the temperature does not exceed −20° C. After 3.5 h at −40 to −20° C., pyrimidine-5-carbonyl chloride hydrochloride (10.2 g, 57 mmol) is added to the suspension and the mixture is stirred at RT for 16 h. 200 ml of hydrochloric acid (1 N in Et$_2$O) are then added to the clear reaction mixture, in connection with which a precipitate is formed. 300 ml of phosphate buffer are added to a suspension and the mixture is extracted with ethyl acetate after the organic phase has been separated off. The combined organic phases are dried over magnesium sulphate and evaporated to dryness. The residue is crystallized from acetonitrile. Yield: 13.2 g. The crude product is used for further syntheses without any additional purification.

Z-3) N-[7-Oxo-6-(pyrazine-2-carbonyl)-4,5,6,7-tetrahydrobenzthiazol-2-yl]acetamide

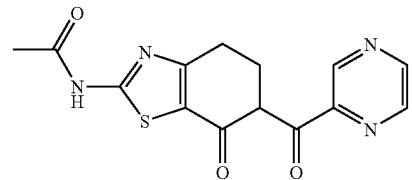

10 g (48 mmol) of Z-6 are added in portions to a suspension of 8.1 g (143 mmol) of sodium methoxide in 100 ml of DMF in such a way that the temperature does not rise above 30° C. After it has been stirred at RT for 1 h, the reaction mixture is heated to 55° C., at which temperature a solution of 10 g (72 mmol) of methyl pyrazine-2-carboxylate in 40 ml of benzene is added. The solution is stirred at 55° C. for a further 3 h, and then at RT for 15 h, before it is adjusted to pH 3 with hydrochloric acid (4 N in dioxane). Following hydrolysis with phosphate buffer, the reaction mixture is extracted with ethyl acetate. The combined organic phases are dried and evaporated in vacuo. The residue is recrystallized from ether/petroleum ether. Yield: 8.7 g.

Z-4) N-[6-(3-Nitrobenzoyl)-7-oxo-4,5,6,7-tetrahydrobenzothiazol-2-yl]acetamide

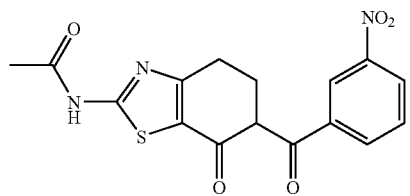

5.2 g of Z-4 are obtained, in analogy with the preparation of intermediate compound Z-1, from 2.5 g (12 mmol) of Z-6, 4.2 g (22 mmol) of 3-nitrobenzoyl chloride and 36 ml (36 mmol) of Li-HMDS (1N in THF). The crude product is used for further syntheses without any additional purification.

Z-5) N-[6-(4-Nitrobenzoyl)-7-oxo-4,5,6,7-tetrahydrobenzothiazol-2-yl]acetamide

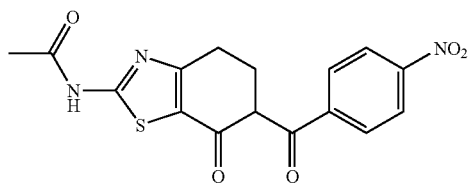

2.2 g of Z-5 are obtained, in analogy with the preparation of intermediate compound Z-1, from 1 g (4.8 mmol) of Z-6, 1.2 g (6.2 mmol) of 4-nitrobenzoyl chloride and 14.6 ml (14.6 mmol) of Li-HMDS (1 N in THF). The crude product is used for further syntheses without any additional purification.

Z-6) N-(7-Oxo-4,5,6,7-tetrahydrobenzothiazol-2-yl)acetamide

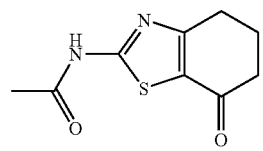

a) 112 g (1 mol) of 1,3-cyclohexanedione are suspended in 700 ml of ice water and 51.6 ml (1 mol) of bromine are added dropwise, at 0° C. and within 45 min. The suspension is subsequently stirred for 3.5 h at a max. of 10° C. The mixture is then filtered with suction and the solid is thoroughly stirred in 800 ml of water, filtered off with suction, washed with 3 l of water and dried. The solid which is obtained is recrystallized from ethanol. Yield: 37 g (Z-6a)

b) 15.5 g (0.2 mol) of thiourea are initially introduced, at room temperature, in 200 ml of ethanol. 37.1 g (0.2 mol) of Z-6a are added in portions to this suspension and the mixture is then rewashed with 60 ml of ethanol. The solution, which is forming gradually, is stirred under reflux for 2 h and then evaporated. The residue is extracted with water and diethyl ether; the water phase is made alkaline with sodium carbonate solution. The solid which is formed in this connection is filtered off with suction and washed with water. It is then thoroughly stirred with methanol and this mixture is evaporated to dryness. Yield: 22 g (Z-6b)

c) 230 ml (2.4 mol) of acetic anhydride are initially introduced at room temperature after which 22 g (0.13 mol) of Z-6b are added and the mixture is stirred under reflux for 3 h. During this period, the suspension partially goes into solution. After the mixture has been cooled down using an ice/sodium chloride bath, the solid is filtered off with suction, boiled up 2× in each case 150 ml of acetone, filtered off with suction and dried. Yield: 25 g (m.p.: 268-272° C.)

Z-7) N-(6-Formyl-7-oxo-4,5,6,7-tetrahydrobenzothiazol-2-yl)acetamide

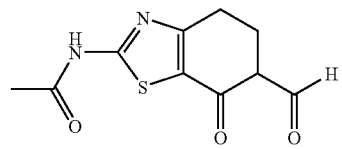

20 g (0.37 mol) of sodium methoxide are suspended in 50 ml of dimethylformamide and a suspension of 21 g (0.1 mol) of Z-6 in 100 ml of DMF is added dropwise. The mixture is subsequently stirred for 15 min and then cooled down to 0° C. A mixture of 29.9 ml (0.37 mol) of ethyl formate and 60 ml of benzene is added dropwise and the reaction mixture is diluted with a further 100 ml of benzene. A precipitate gradually sediments and the mixture is stirred for a further 3.5 h at 0° C. The suspension is hydrolysed with 370 ml of 1 molar hydrochloric acid and the solid which precipitates out in this connection is filtered off with suction. The two phases of the mother liquor are separated and the water phase is extracted with dichloromethane. The organic phase which results from this is dried and evaporated to dryness. The solid and the residue from the extraction are recrystallized from acetonitrile. Yield: 20 g

Z-8) N-[6-(Furan-2-carbonyl)-7-oxo-4,5,6,7-tetrahydrobenzothiazol-2-yl]acetamide

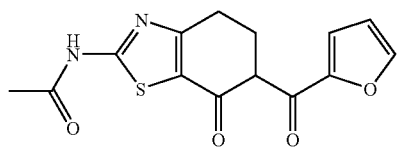

1.7 g of Z-8 are obtained, in analogy with the preparation of Z-7, from 2 g (10 mmol) of Z-6, 1.6 g (30 mmol) of sodium methoxide and 3.8 g (30 mmol) of methyl 2-furanate. (m.p.: 255-256° C.)

Z-10) Methyl (2-acetylamino-7-oxo-4,5,6,7-tetrahydrobenzothiazol-6-yl)oxo acetate

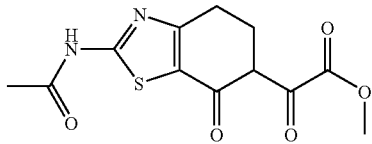

52 g of Z-10 are obtained, in analogy with the preparation of Z-7, from 40 g (190 mmol)of Z-6, 38 g (0.7 mmol) of sodium methoxide and 84 g (0.7 mol) of dimethyl oxalate.

Z-11) N-(6-Benzoyl-7-oxo-4,5,6,7-tetrahydrobenzothiazol-2-yl)acetamide

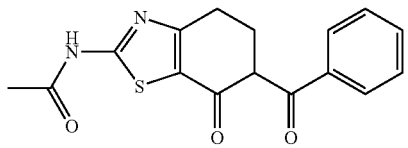

3.6 g of Z-11 are obtained, in analogy with the preparation of Z-7, from 10 g (50 mmol) of intermediate compound 1, 7.8 g (140 mmol) of sodium methoxide and 17.9 ml (140 mmol) of methyl benzoate.

Z-12) N-[7-Oxo-6-(pyridine-3-carbonyl)-4,5,6,7-tetrahydrobenzothiazol-2-yl]acetamide

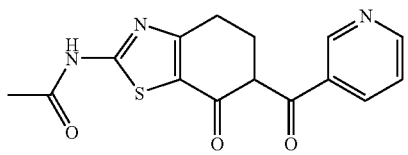

3.1 g of the product Z-12 are obtained, in analogy with the preparation of Z-7, from 4 g (19 mmol) of Z-6, 3.9 g (57 mmol) of sodium methoxide and 7.9 g (57 mmol) of methyl nicotinate.

Z-13) Methyl [7-oxo-6-(pyridine-3-carbonyl)-4,5,6,7-tetrahydrobenzothiazol-2-yl]carbamate

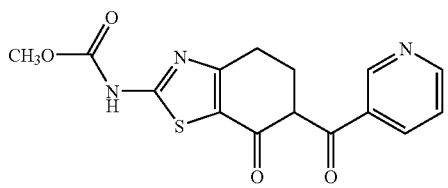

a) 2-Amino-5,6-dihydro-4H-benzothiazol-7-one

A suspension of 23 g of Z-6 (109 mmol) in a mixture of 300 ml of hydrochloric acid (4 M in dioxane) and 30 ml of water is stirred at 60° C. for 15 h. After it has been cooled down to 0° C., the reaction mixture is made alkaline (pH 10) with 8 N sodium hydroxide solution. The precipitate is filtered off, washed with diethyl ether and subjected to further use without any additional purification. Yield: 22.4 g b) Methyl (7-oxo-4,5,6,7-tetrahydrobenzothiazol-2-yl)carbamate 572 μl of methyl chloroformate (7.3 mmol) are added to a solution of 500 mg of 2-amino-5,6-dihydro-4H-benzothiazol-7-one (2.4 mmol) in 5 ml of pyridine. The reaction mixture is stirred at 50° C. for 15 h and then diluted with ethyl acetate; the mixture is then extracted by shaking, in each case 2×, with water and cold 1 N hydrochloric acid. The organic phase is dried and evaporated. Yield: 290 mg c) The desired compound is obtained, in analogy with the preparation of Z-1, from 340 mg of methyl (7-oxo-4,5,6,7-tetrahydrobenzothiazol-2-yl)carbamate (1.5 mmol), 4.7 ml of Li-HMDS (1N in THF) and 520 mg of imidazol-1-ylpyridin-3-ylmethanone (3 mmol) in 30 ml of THF. Yield: 480 mg Z-14) Ethyl [7-oxo-6-(pyridin-3-carbonyl)-4,5,6,7-tetrahydrobenzothiazol-2-yl]thiocarbamate

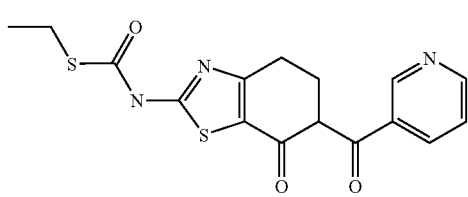

a) Ethyl (7-oxo-4,5,6,7-tetrahydrobenzothiazol-2-yl)thiocarbamate

The desired thiocarbamate is obtained in analogy with the preparation of Z-13 b, starting from 101 g of 2-amino-5,6-dihydro-4H-benzothiazol-7-one (602 mmol) in 3.4 l of pyridine and 75 g of ethyl chlorothioformate (602 mmol). Yield: 84 g b) The desired compound is obtained, in analogy with the preparation of Z-1, from 17 g of ethyl (7-oxo-4,5,6,7-tetrahydrobenzothiazol-2-yl)thiocarbamate (67 mmol), 200 ml of Li-HMDS (1N in THF) and 23 g of imidazol-1-ylpyridin-3-ylmethanone (133 mmol) in 400 ml of THF. Yield: 18 g Z-15) Ethyl [7-oxo-6-(pyrimidine-5-carbonyl)-4,5,6,7-tetrahydrobenzothiazol-2-yl]thiocarbamate

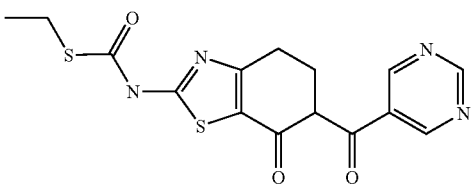

The desired compound is obtained, in analogy with the preparation of Z-1, from 12 g of ethyl (7-oxo-4,5,6,7-tetrahydrobenzothiazol-2-yl)thiocarbamate (Z-14a, 46 mmol), 140 ml of Li-HMDS (1N in THF) and 12 g of imidazol-1-ylpyrimidin-5-ylmethanone (56 mmol) in 300 ml of THF. Yield: 13 g I-1) 4-(7-Acetylamino-4,5-dihydropyrazolo[3',4':3,4]benzo[1,2-d]thiazol-1-yl)-3-chlorobenzoic acid

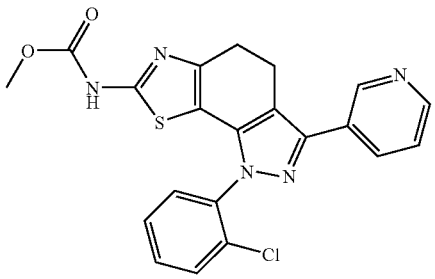

A suspension of Z-13 (480 mg, 1.5 mmol) and 2-chlorophenylhydrazine hydrochloride (267 mg, 1.5 mmol) in 10 ml of glacial acetic acid is stirred at 100° C. for 4 h. The reaction mixture is then diluted with 500 ml of water and the precipitate is filtered off. Yield: 116 mg I-3) N-[1-(2-Chloropyridin-4-yl)-3-furan-2-yl-4,5-dihydro-1H-pyrazolo[3',4':3,4]benzo[1,2-d]thiazol-7-yl]acetamide

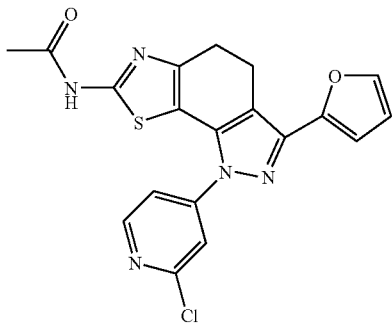

The desired product is obtained in analogy with the preparation of I-1, starting from Z-8 (1.5 g, 5 mmol) and 2-chloropyridin-4-ylhydrazine hydrochloride in 25 ml of glacial acetic acid. Yield: 1.6 g I-4) 4-(7-Acetylamino-3-furan-2-yl-4,5-dihydropyrazolo[3',4':3,4]benzo[1,2-d]thiazol-1-yl)-3-chlorobenzoic acid

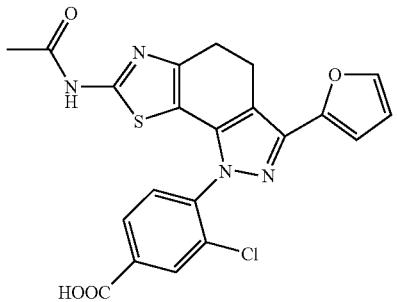

In analogy with the preparation of I-1, Z-8 (12 g, 35 mmol) and methyl 3-chloro-4-hydrazinobenzoate (8.5 g, 35 mmol) are stirred in 80 ml of glacial acetic acid at RT for 4 d. The methyl ester (1.1 g) which is obtained after precipitating in ice water is then hydrolysed using lithium hydroxide (178 mg in 15 ml of dioxane). Acidifying with 2 N hydrochloric acid yields the desired product as a solid. Yield: 0.8 g I-6) 7-Acetylamino-1-phenyl-4,5-dihydro-1H-pyrazolo[3',4':3,4]benzo[1,2-d]thiazole-3-carboxylic acid

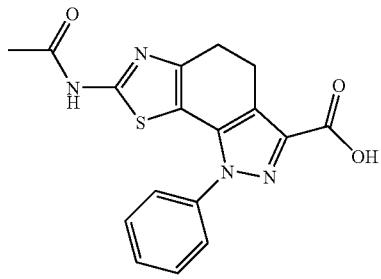

27 g of product are obtained in analogy to the preparation of I-1 from 30 g (0.1 mol) of Z-10 and 10.3 ml (0.1 mol) of phenyl hydrazine. (m.p.: 298-300° C.). 0.1 g of this compound (0.3 mmol) is suspended in 12 ml of methanol/water (1:1) after which 0.4 ml of a 10% potassium hydroxide solution is added. After 1.5 h, the reaction mixture is evaporated and the solution is acidified with dilute hydrochloric acid. The resulting precipitate is recrystallized from acetonitrile. Yield: 0.1 g (m.p.: >300° C.)

I-8) 4-(7-Acetylamino-3-phenyl-4,5-dihydropyrazolo[3',4':3,4]benzo[1,2-d]thiazol-1-yl)-3-chlorobenzonitrile

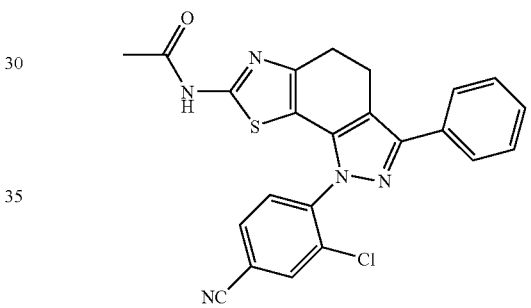

The desired product is obtained in analogy with the preparation of I-1, starting from Z-11 (10 g; 12.7 mmol) and 3-chloro-4-hydrazinobenzonitrile (4.5 g, 26.8 mmol) in 50 ml of glacial acetic acid. Yield: 1.6 g I-9) 4-(7-Acetylamino-3-phenyl-4,5-dihydropyrazolo[3',4':3,4]benzo[1,2-d]thiazol-1-yl)-3-chlorbenzoic acid

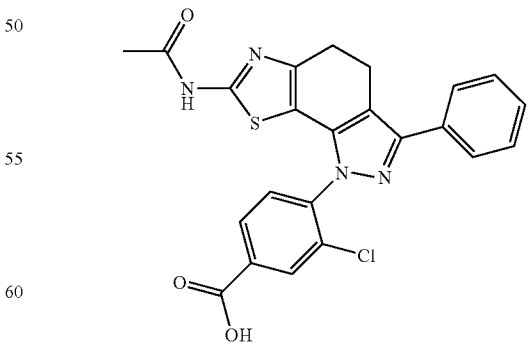

The desired compound is obtained in analogy with the preparation of I-4, starting from Z-11 (2.3 g, 7.1 mmol) and methyl 3-chloro-4-hydrazinobenzoate (1.8 g, 8.5 mmol). Yield: 0.36 g I-10) N-[1-(2-Chloro-4-nitrophenyl)-3-phenyl-4,5-dihydro-1H-pyrazolo[3',4':3,4]benzo[1,2-d]thiazol-7-yl]acetamide

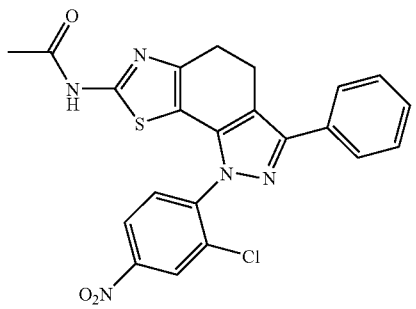

The desired product is obtained in analogy with the preparation of I-1, starting from Z-11 (7.5 g; 13.1 mmol) and 3-chloro-4-hydrazinonitrobenzene (3.2 g, 14.4 mmol) in 100 ml of glacial acetic acid. Yield: 1.1 g I-11) N-(1-Piperidin-4-yl-3-pyridin-3-yl-4,5-dihydro-1H-pyrazolo-[3',4':3,4]benzo[1,2-d]thiazol-7-yl)acetamide

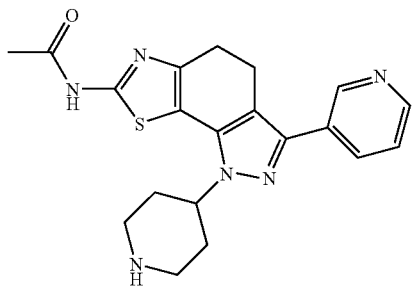

In analogy with the preparation of I-1, Z-12 (2.5 g, 7.9 mmol) and H-5 (1.2 g, 7.9 mmol) are stirred in 50 ml of glacial acetic acid at 60° C. for 15 h. The mixture is poured onto ice water and rendered alkaline with 1 N sodium hydroxide solution (pH 12). The resulting precipitate is filtered off, washed with water and dried at 40° C. in vacuo. Yield: 2 g I-12) 4-(7-Acetylamino-3-pyridin-3-yl-4,5-dihydro-pyrazolo[3',4':3,4]benzo[1,2-d]thiazol-1-yl)cyclohexanecarboxylic acid

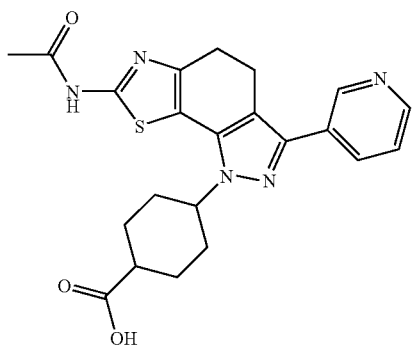

-continued

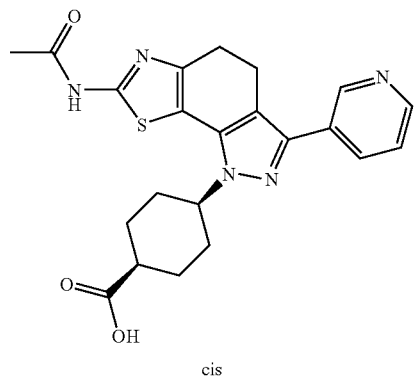

cis

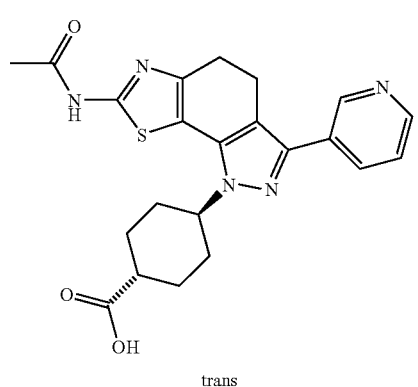

trans

The desired compound is obtained in analogy with the preparation of I-4 starting from Z-12 (1.9 g, 5.8 mmol) and H-6 (1.3 g, 5.8 mmol). Yield: 0.78 g.

The corresponding cis and trans compounds are obtained by using the isomerically pure cisH-6 and transH-6, respectively.

Other intermediate compounds which are prepared in analogy with the above-described syntheses.

| No. | Starting compound | Structure |
| --- | --- | --- |
| I-13 | Z-12 | 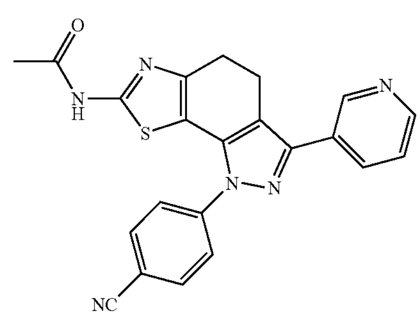 |

-continued

| No. | Starting compound | Structure |
|---|---|---|
| I-14 | Z-12 | (structure) |
| I-15 | Z-12 | (structure) |
| I-16 | Z-12 | (structure) |
| I-17 | Z-12 | (structure) |
| I-18 | Z-12 | (structure) |
| I-19 | Z-12 | (structure) |
| I-20 | Z-12 | (structure) |
| I-21 | Z-12 | (structure) |
| I-22 | Z-12 | (structure) |

-continued
| No. | Starting compound | Structure |
|---|---|---|
| I-23 | Z-12 H-2 | 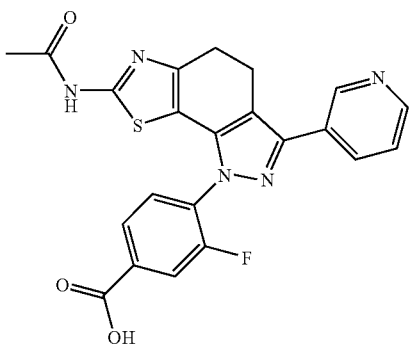 |
| I-24 | Z-12 H-3 | 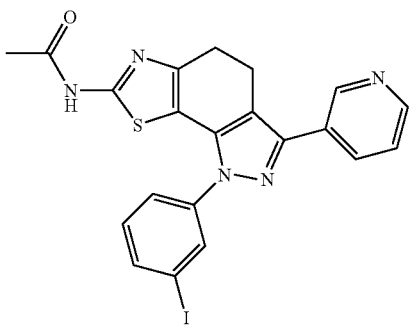 |
| I-25 | Z-12 | 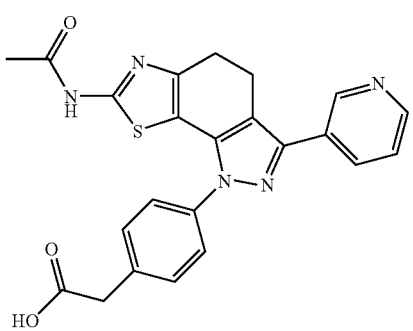 |
| I-26 | Z-12 H-4 | 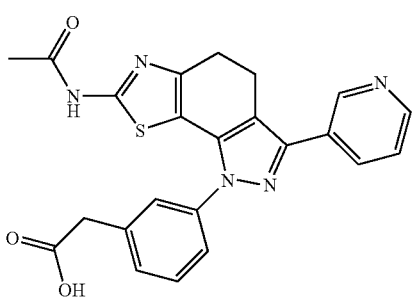 |
-continued
| No. | Starting compound | Structure |
|---|---|---|
| I-27 | Z-1 | 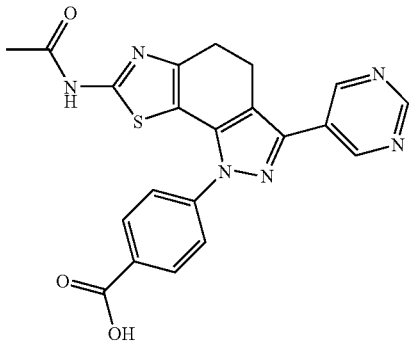 |
| I-28 | Z-3 H-1 | 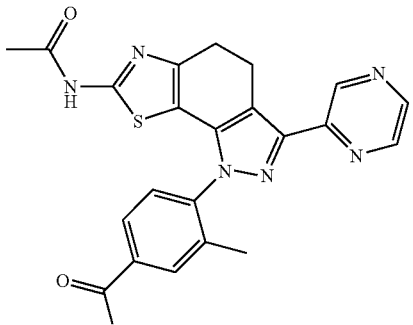 |
| I-29 | Z-3 H-7 | 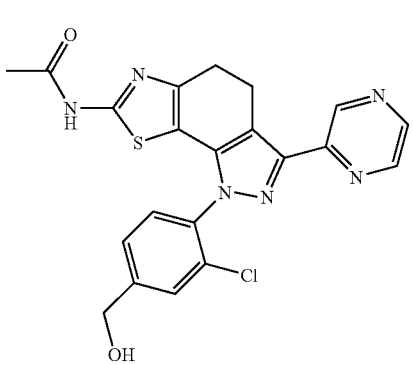 |
| I-30 | Z-3 | 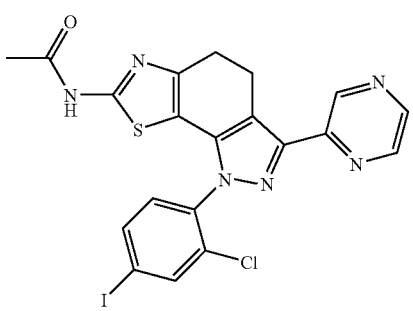 |

-continued
| No. | Starting compound | Structure |
|---|---|---|
| I-31 | Z-3 | 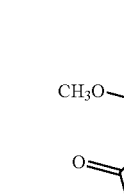 |
| I-32 | Z-4 | 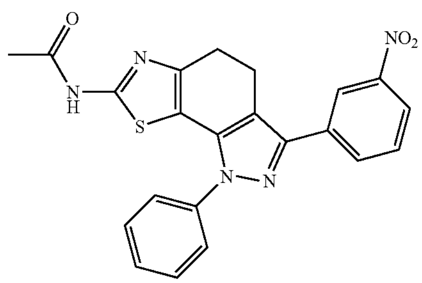 |
| I-33 | Z-4 | 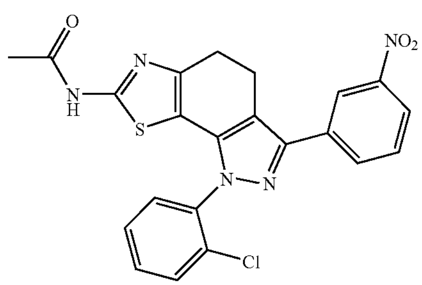 |
| I-34 | Z-5 | 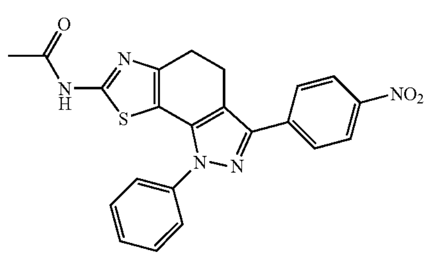 |
| I-35 | Z-5 | 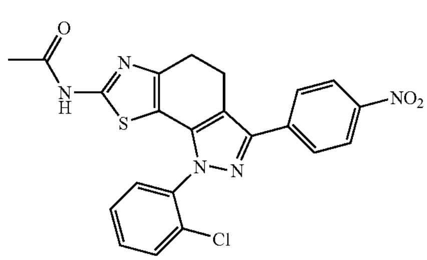 |
-continued
| No. | Starting compound | Structure |
|---|---|---|
| I-36 | Z-12 | 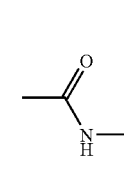 |
| I-37 | Z-11 | 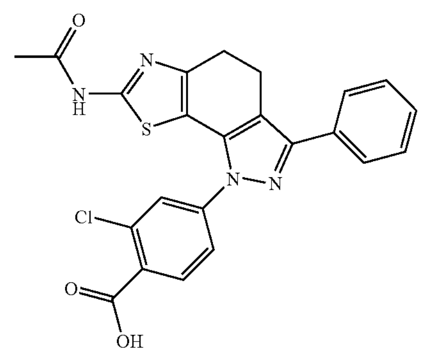 |
| I-38 | Z-11 | 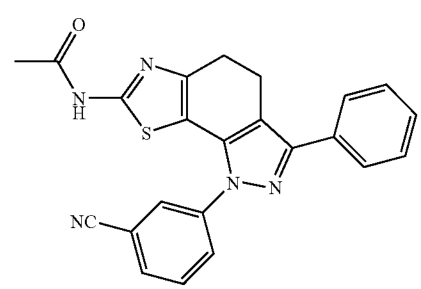 |
| I-39 | Z-12 | 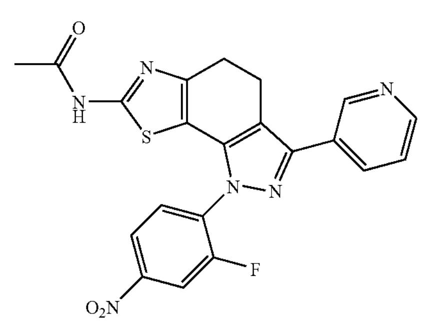 |

-continued

| No. | Starting compound | Structure |
|---|---|---|
| I-40 | Z-12 H-12 | 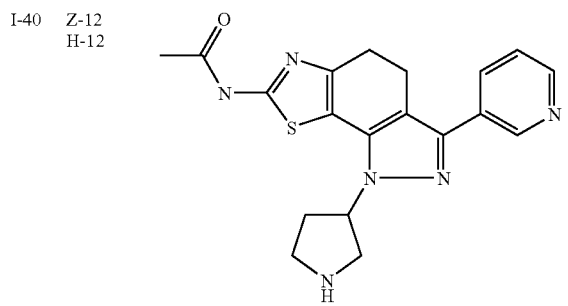 |
| I-41 | Z-14 | 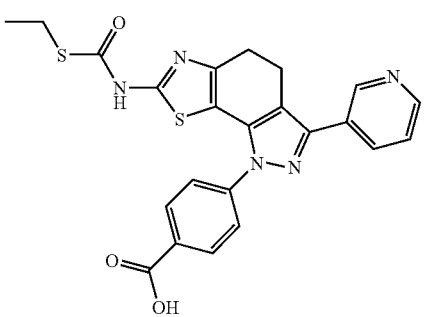 |
| I-42 | Z-14 | 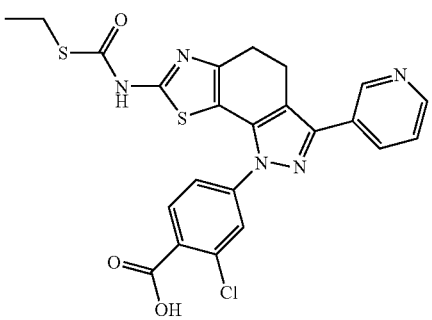 |
| I-43 | Z-14 | 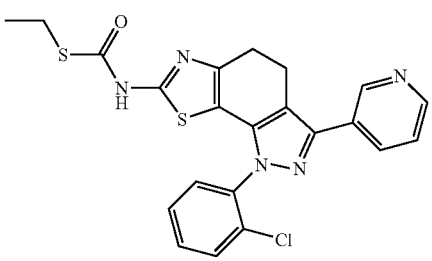 |
| I-44 | Z-15 | 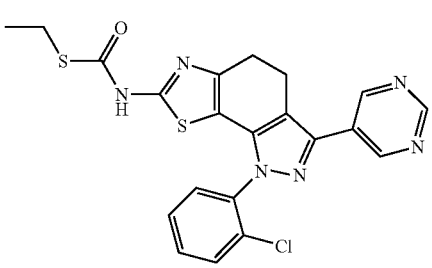 |

-continued

| No. | Starting compound | Structure |
|---|---|---|
| I-45 | Z-3 | 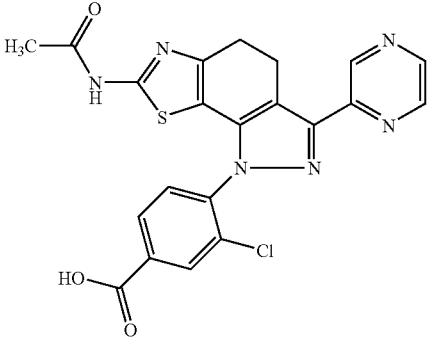 |
| I-45 | Z-12 | 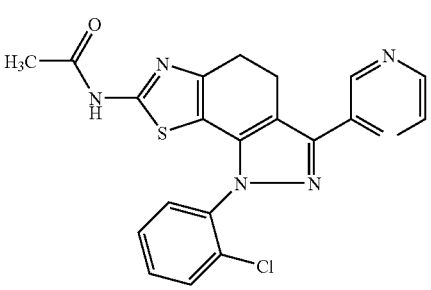 |

II-1) N-[1-(4-Amino-2-chlorophenyl)-3-furan-2-yl-4,5-dihydro-1H-pyrazolo[3',4':3,4]benzo[1,2-d]thiazol-7-yl]acetamide

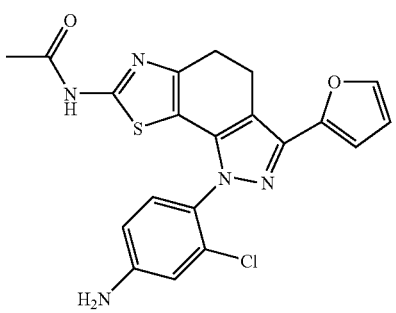

Diphenyl phosphoryl azide (1.1 ml, 5 mmol) and 0.7 ml of triethylamine are added to a solution of I-4 (2.1 g, 4.6 mmol) in 20 ml of DMF and the mixture is stirred at 50° C. for 6 h. p-Toluenesulphonic acid (1.5 g, 9.1 mmol) and 3 ml of water are added to the reaction mixture, which is stirred at 50° C. for 39 h. The mixture is then poured onto 300 ml of ice water and the resulting precipitate is filtered off. The residue is purified chromatographically on silica gel using dichloromethane: methanol:ammonia 98:2:0.2. Yield: 0.6 g II-3) N-[1-(4-Amino-2-chlorophenyl)-3-phenyl-4,5-dihydro-1H-pyrazolo[3',4':3,4]benzo[1,2-d]thiazol-7-yl]acetamide

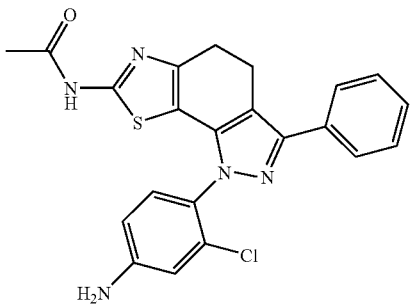

Iron powder (0.77 g, 13.8 mmol) is added to a solution of I-10 (1.1 g, 2 mmol) in 20 ml of glacial acetic acid and the mixture is stirred at 70° C. for 4 h. After filtering through kieselguhr, the solvent is removed in vacuo and the residue is purified chromatographically on silica gel using dichloromethane:methanol 99:1. Yield: 0.8

II-4) N-[1-(4-Aminophenyl)-3-pyridin-3-yl-4,5-dihydro-1H-pyrazolo[3',4':3,4]benzo[1,2-d]thiazol-7-yl]acetamide

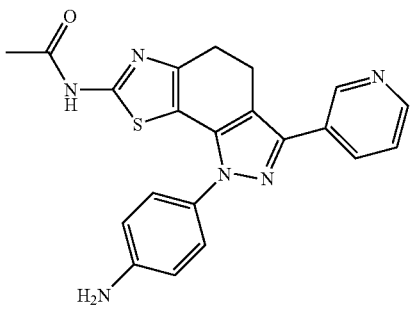

The desired product is obtained in analogy with the preparation of II-2, starting from I-16 (0.2 g, 0.5 mmol). Yield: 0.14 g II-5) N-[1-(3-Aminophenyl)-3-pyridin-3-yl-4,5-dihydro-1H-pyrazolo[3',4':3,4]benzo[1,2-d]thiazol-7-yl]acetamide

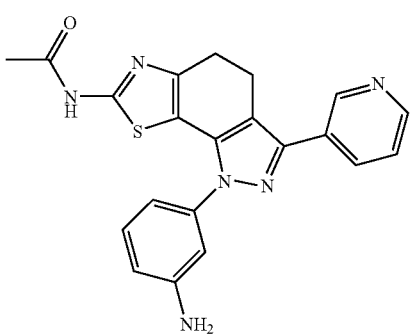

I-17 (1.2 g, 2.8 mmol) is suspended in 150 ml of methanol in a 250 ml hydrogenation reactor. Palladium (5% on active charcoal, 120 mg) is added to the suspension and the latter is stirred at RT and a hydrogen pressure of 50 psi. In each case the same quantity of catalyst is added once again after 18 h and after 40 h. After a further 15 h, the catalyst is filtered off and the solvent is removed in vacuo. Yield: 0.89 g II-6) N-[1-(4-Amino-2-chlorophenyl)-3-pyridin-3-yl-4,5-dihydro-1H-pyrazolo[3',4':3,4]benzo[1,2-d]thiazol-7-yl]acetamide

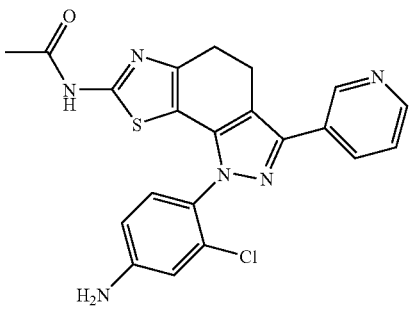

The desired product is obtained in analogy with the preparation of II-3, starting from I-18 (10 g, 21 mmol). Yield: 8.4 g II-9) Ethyl [4-(7-acetylamino-3-phenyl-4,5-dihydropyrazolo[3',4':3,4]benzo[1,2-d]thiazol-1-yl)-3-chlorophenyl]thiocarbamate

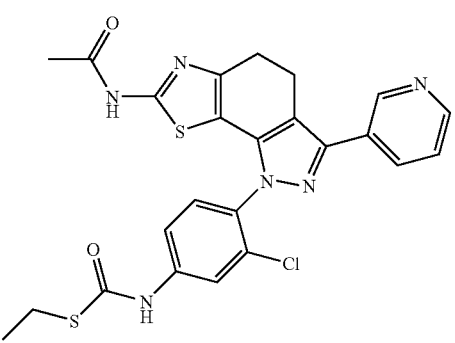

Ethyl chlorothioformate (0.7 ml) is added dropwise to a solution of II-6 (3 g, 5.8 mmol) in 75 ml of pyridine and the mixture is stirred at RT for 4 h. After the pyridine has been removed on a rotary evaporator, the residue is taken up in water and the precipitate is filtered off A solid, which is dried in vacuo at 60° C. for 15 h, is obtained. Yield: 3 g II-10) N-[1-(4-Aminomethyl-2-chlorophenyl)-3-phenyl-4,5-dihydro-1H-pyrazolo[3',4':3,4]benzo[1,2-d]thiazol-7-yl]acetamide

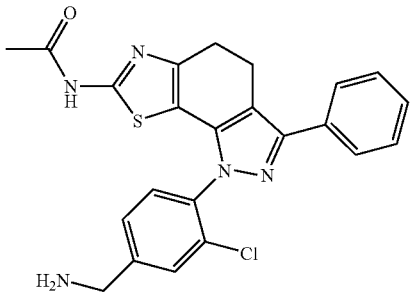

20 mg of Raney nickel are added to a solution of I-8 (1.5 g, 3.3 mmol) in 150 ml of ammoniacal methanol and the mixture is stirred at RT for 15 h under a hydrogen atmosphere (3.5 bar). The mixture is taken up in dichloromethane and this solution is filtered through silica gel. After the solvent has been removed in vacuo, the residue is crystallized from diethyl ether/petroleum ether. Yield: 1.1 g II-11) N-[1-(2-Chloro-4-formylphenyl)-3-pyrazin-2-yl-4,5-dihydro-1H-pyrazolo[3',4':3,4]benzo[1,2-d]thiazol-7-yl]acetamide

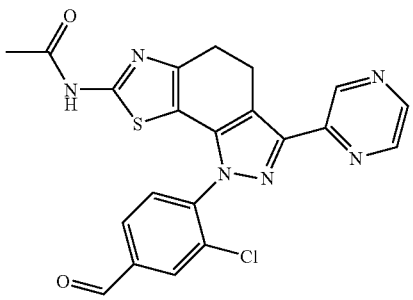

2 g of manganese dioxide are added to a solution of I-29 (0.5 g, 1.1 mmol) in 25 ml of acetone and the mixture is refluxed for 3 h. The reaction mixture is then filtered and the solvent is removed in vacuo. Yield: 0.25 g II-12) N-[1-(3-Aminomethyl)-3-phenyl-4,5-dihydro-1H-pyrazolo[3',4':3,4]benzo[1,2-d]thiazol-7-yl]acetamide

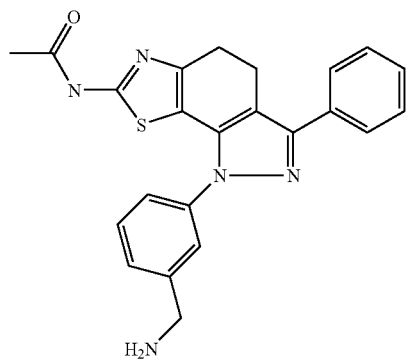

The desired product is obtained in analogy with the preparation of II-10, starting from I-38 (2.3 g, 5.6 mmol). Yield: 1.4 g II-13) N-[1-(4-Amino-2-fluorophenyl)-3-pyridin-3-yl-4,5-dihydro-1H-pyrazolo[3',4':3,4]benzo[1,2-d]thiazol-7-yl]acetamide

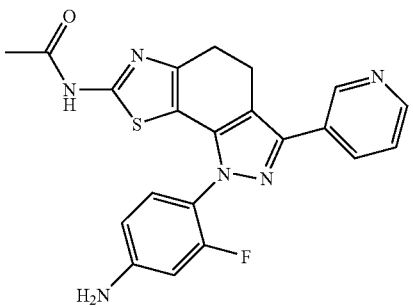

The desired product is obtained in analogy with the preparation of II-3, starting from I-39 (1 g, 2.2 mmol). Yield: 1 g II-14) 4-(7-Amino-3-pyridin-3-yl-4,5-dihydropyrazolo[3',4':3,4]benzo[1,2-d]thiazol-1-yl)-N,N-dimethylbenzamide

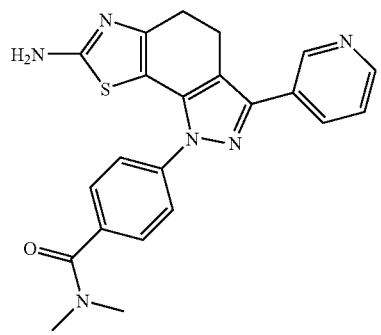

10 ml of conc. hydrochloric acid and 100 ml of water are added to a solution of I-20 (6.3 g, 14.5 mmol) in 150 ml of dioxane and the mixture is heated under reflux for 6 h. The clear solution is stirred at 50° C. for a further 16 h and then evaporated to dryness in vacuo. The deacetylation product (6.6 g, 14 mmol) is dissolved in 150 ml of DMF after which TBTU (5.1 g, 15 mmol) and 10 ml of triethylamine are added. The reaction mixture is stirred at RT for 30 min, after which dimethylamine hydrochloride (1.25 g, 15 mmol) is added and the mixture is stirred at RT for a further 6 h. Following hydrolysis with 1 l of water, the resulting precipitate is filtered off and dried in vacuo. Yield: 5.5 g II-15) 4-(7-Amino-3-pyridin-3-yl-4,5-dihydropyrazolo[3',4':3,4]benzo[1,2-d]thiazol-1-yl)-3-chloro-N,N-dimethylbenzamide dihydrochloride

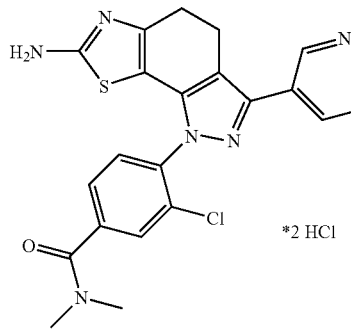

*2 HCl 5.5 ml of hydrochloric acid (4 M in dioxane) and 5.5 ml of water are added to a solution of Example 2.180 (500 mg, 1 mmol) and the mixture is heated at 80° C. for 2.5 h. The clear solution is stirred at 70° C. for a further 15 h and then evaporated to dryness in vacuo. Yield: 580 mg II-16) 4-(7-Amino-3-pyridin-3-yl-4,5-dihydropyrazolo[3',4':3,4]benzo[1,2-d]thiazol-1-yl)-3-fluoro-N,N-dimethylbenzamide

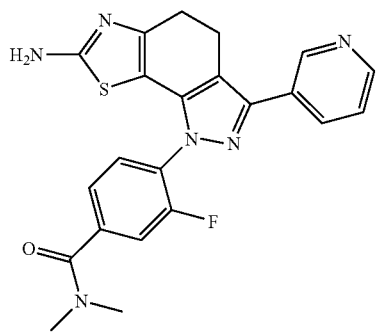

30 ml of hydrochloric acid (37%) and 35 ml of water are added to a solution of Example 2.182 (1.37 g, 2.9 mmol) and the mixture is heated at 50° C. for 12 h. After evaporating in vacuo, the residue is taken up in water and 4 N sodium hydroxide solution is added. The resulting precipitate is filtered and dried. Yield: 1.1 g II-17) 1-(2-Chlorophenyl)-3-pyridin-3-yl-4,5-dihydro-1H-pyrazolo[3',4':3,4]benzo[1,2-d]thiazol-7-ylamine

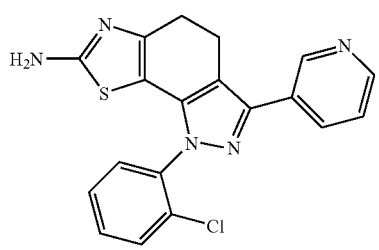

The desired product is obtained in analogy with the preparation of II-16, starting from I-46 (10.3 g, 24 mmol) and 280 ml of hydrochloric acid (37%) in 330 ml of water. Yield: 7.6 g II-18) 1-Phenyl-3-pyridin-3-yl-4,5-dihydro-1H-pyrazolo[3',4':3,4]benzo[1,2-d]thiazol-7-ylamine

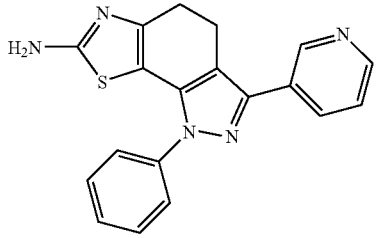

The desired product is obtained in analogy with the preparation of II-16, starting from Example 1.13 (7.7 g, 20 mmol), and 50 ml of hydrochloric acid (37%) in 30 ml of water. Yield: 6.8 g II-19) 4-(7-Amino-3-pyridin-3-yl-4,5-dihydropyrazolo[3',4':3,4]benzo[1,2-d]thiazol-1-yl)-3-chlorobenzoic acid

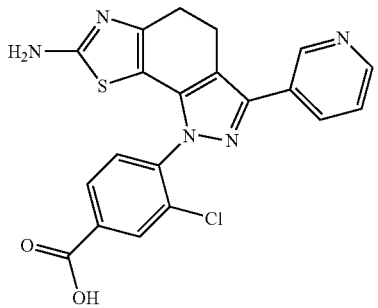

The desired product is obtained in analogy with the preparation of intermediate compound II-16, starting from Example 1.21 (2.9 g, 5 mmol) and 2 ml of hydrochloric acid (32%) in a mixture of 10 ml of water and 20 ml of dioxane. Yield: 2.7 g Analytical Methods Method AM1:

| | |
|---|---|
| HPLC: | Agilent 1100 series; MS: 1100 series LC/MSD (API-ES (+/−3000 V, Quadrupole, G1946D); mode: Scan pos 100-1000, neg 100-1000 |
| Column: | Waters; part no. 186000594; XTerra MS C18 2.5 μm; 2.1 × 50 mm column |
| Solvent: | A: H₂O, deionized and containing 0.1% added formic acid<br>B: Acetonitrile, HPLC grade and contaiing 0.1% added formic acid |
| Detection: | peak width > 0.1 min (2 s); 190-450 nm<br>UV 254 nm (bandwidth 8, reference off)<br>UV 230 nm (bandwidth 8, reference off) |
| Injection: | 1 μl standard injection |
| Flow rate: | 0.6 ml/min |

-continued

| | |
|---|---|
| Column temperature: | 35° C. |
| Pump gradient: | 0.0-0.5 min    5% B |
| | 0.5-1.5 min    5% -> 50% B |
| | 1.5-4.0 min    50% -> 95% B |
| | 4.0-6.0 min    95% B |
| | 6.0-6.5 min    95% -> 5% B |
| | 1.5 min post run    5% B |

Method AM2

| | |
|---|---|
| HPLC: | Agilent Series 1100 (G1379A/G1310A converted to G1311A/G1313A/G1316A/G1948D/G1315B/G1946D) mode: Scan pos 100-1000, neg 100-1000 |
| Column: | Agilent Zorbax SB-C8, 2.1 × 50 mm, 3.5 µm |
| Solvent: | A: $H_2O$, deionized and containing 0.1% added formic acid |
| | B: Acetonitrile HPLC grade and containing 0.1% added formic acid |
| Detection: | peak width > 0.1 min (2 s); 190-450 nm |
| | UV 254 nm (bandwidth 8, reference off) |
| | UV 230 nm (bandwidth 8, reference off) |
| Injection: | 2.5 µl standard injection |
| Flow rate: | 0.6 ml/min |
| Column temperature: | 35° C. |
| Pump gradient: | 0-3.0 min    10% -> 90% B |
| | 3.0-4.0 min    90% B |
| | 4.0-5.0 min    90% -> 10% B |

Method AM3

| | |
|---|---|
| HPLC: | Agilent Series 1100 (G1312A/G1315A/G1316A/G1367A) Agilent MSD SL ESI |
| Mode: | Scan pos 150-750 |
| Column: | Agilent Zorbax SB-C8, 2.1 × 50 mm, 3.5 µm |
| Solvent: | A: $H_2O$ deionized and containing 0.1% added formic acid |
| | B: Acetonitrile, HPLC grade and containing 0.1% added formic acid |
| Detection: | peak width > 0.01 min (0.2 s); 190-450 nm |
| | UV 254 nm (bandwidth 16, reference off) |
| | UV 230 nm (bandwidth 8, reference off) |
| | UV 214 nm (bandwidth 8, reference off) |
| Injection: | 3.0 µl overlap injection |
| Flow rate: | 1.1 ml/min |
| Column temperature: | 45° C. |
| Pump gradient: | 0-1.75 min    15% -> 95% B |
| | 1.75-1.90 min    95% B |
| | 1.90-1.92 min    950% -> 15% B |

Method AM4

| | |
|---|---|
| HPLC: | Agilent 1100 series |
| MS: | Agilent LC/MSD SL (LCMS1: 1100 series LC/MSD) |
| Column: | Waters, Xterra MS C18, 2.5 µm, 2.1 × 30 mm, part no. 186000592 |
| Solvent | A: $H_2O$ deionized and containing 0.1% added formic acid |
| | B: Acetonitrile, HPLC grade and containing 0.1% added formic acid |
| Detection: | MS: positive and negative |
| | mass range: 120-900 m/z |
| | fragmentor: 120 |
| | gain EMV: 1 |
| | threshold: 150 |
| | step size: 0.25 |
| | UV: 254 nm |
| | bandwidth: 1 (LCMS1: 2) |
| | reference: off |
| | spectrum: |
| | range: 250-400 nm |
| | range step: 1.00 nm |
| | threshold: 4.00 mAU |
| | peak width: <0.01 min (LCMS1: >0.05 min) |
| | slit: 1 nm (LCMS1: 2 nm) |
| Injection: | 5 µl |
| Flow rate: | 1.10 ml/min |
| Column temperture: | 40° C. |
| Gradient: | 0.00 min    5% B |
| | 0.00-2.50 min    5% -> 95% B |
| | 2.50-2.80 min    95% B |
| | 2.81-3.10 min    95% -> 5% B |

Method AM5

| | |
|---|---|
| HPLC: | Agilent 1100 series |
| MS: | Agilent LC/MSD SL (LCMS1: 1100 series LC/MSD) |
| Column: | Phenomenex, Synergy Polar RP 80A, 4 µm, 2.0 × 30 mm, part no. 00A-4336-B0 |
| Solvent: | A: $H_2O$ (Millipore purified purest water) containing 0.1% HCOOH |
| | B: Acetonitrile (HPLC grade) |
| Detection: | MS: positive and negative |
| | mass range: 120-900 m/z |
| | fragmentor: 120 |
| Gain EMV: | 1 |
| Threshold: | 150 |
| Step size: | 0.25 |
| UV: | 254 nm |
| Bandwidth: | 1 (LCMS1: 2) |
| Reference: | off |
| Spectrum: | |
| | range: 250-400 nm |
| | range step: 1.00 nm |
| | threshold: 4.00 mAU |
| | peak width: <0.01 min (LCMS1: >0.05 min) |
| | slit: 1 nm (LCMS1: 2 nm) |
| Injection: | inj. vol.: 5 µl |
| Inj. mode: | needle wash |
| Separation: | flow rate: 1.10 ml/min |
| | column temp.: 40° C. |
| | gradient: 0.00 min    5% solvent B |
| | 0.00-2.50 min    5% -> 95% solvent B |
| | 2.50-2.80 min    95% solvent B |
| | 2.81-3.10 min    95% -> 5% solvent B |

Method AM6

| | |
|---|---|
| HPLC: | Waters Alliance 2695 |
| Column: | Waters, Xterra MS C18, 2.5 µm, 4.6 × 30 mm, part no. 186000600 |
| Solvent | A: $H_2O$, deionized and containing 0.1% added formic acid |
| | B: Acetonitrile, HPLC grade and containing 0.08% added formic acid |
| Flow rate: | 1 ml/min |
| Column temperature: | 25° C. |
| Gradient: | 0.00 min    5% B |
| | 0.00-3.10 min    5% -> 98% B |
| | 3.10-4.50 min    98% B |
| | 4.50-5.00 min    98% -> 5% B |

| Abbreviations employed | |
|---|---|
| conc. | concentrated |
| d | day |
| DCM | dichloromethane |
| DMAP | N,N-dimethylaminopyridine |
| DMF | N,N-dimethylformamide |
| DMSO | dimethyl sulphoxide |
| EtOH | ethanol |
| h | hour |
| HATU | O-(7-Azabenzotriazol-1-yl)-N,N,N',N'-tetramethyluronium hexafluorophosphate |
| HPLC | high performance liquid chromatography |
| Li-HMDS | lithium hexamethyldisilazane |
| M | molar |
| MeOH | methanol |
| min | minute |
| ml | millilitre |
| m.p. | melting point |
| MS | mass spectrometry |
| N | normal |
| NMR | nuclear magnetic resonance spectroscopy |
| ppm | parts per million |
| Rf | retention factor |
| RP | reversed phase |
| RT | room temperature |
| Rt | retention time |
| TBTU | O-Benzotriazol-1-yl-N,N,N',N'-tetramethyluronium tetrafluoroborate |
| tert | tertiary |

| Abbreviations employed | |
|---|---|
| THF | tetrahydrofuran |
| TLC | thin layer chromatography |

Examples 1.1-1.13

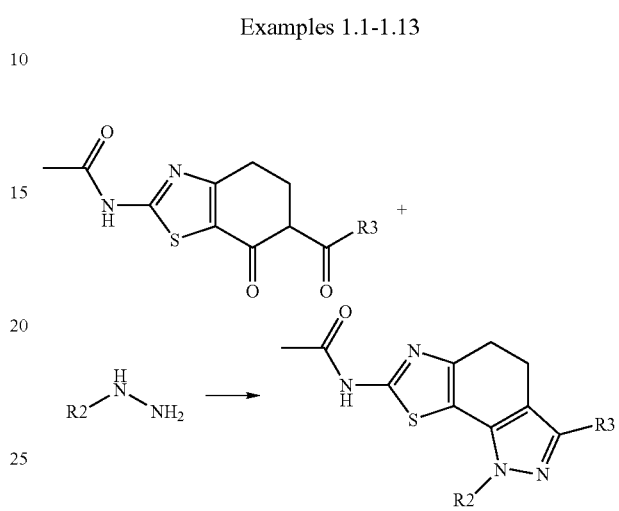

Examples 1.1-1.13 are prepared in analogy with the I-1 synthesis.

| # | Starting compound | Structure | Mass [M + 1]⁺ | HPLC Rt [min] |
|---|---|---|---|---|
| 1.1 | Z-12 | 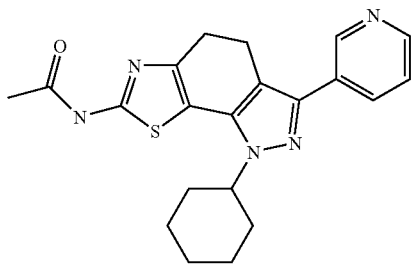 | 394 | 1.88 |

¹H-NMR DMSO-d6, δ [ppm]: 8.86 (s, 1H), 8.53 (d, 4 Hz, 1H), 8.02 (d, 7.7 Hz, 1H), 7.46 (dd, 7.7 and 4.8 Hz, 1 H),, 4.23 (m, 1H), 3.05-3.00 (m, 2H), 2.98-2.93 (m, 2H), 2.18 (s, 3H), 2.05-1.96 (m, 2H), 1.95-1.87 (m, 4H), 1.5-1.4 (m, 2H), 1.32-1.23 (m, 2H).

| 1.2 | Z-12 | 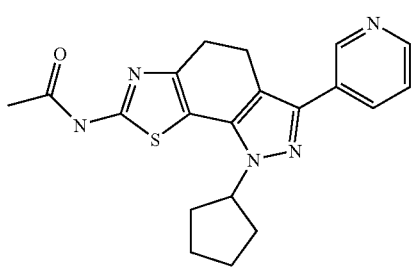 | 380 | 1.67 |

-continued

| # | Starting compound | Structure | Mass [M + 1]+ | HPLC Rt [min] |
|---|---|---|---|---|
| 1.3 | Z-8 H-8 | 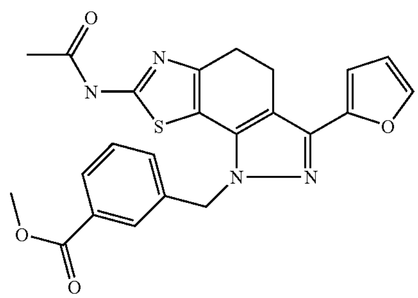 | 449 | 2.1 |
| 1.4 | Z-12 H-9 | 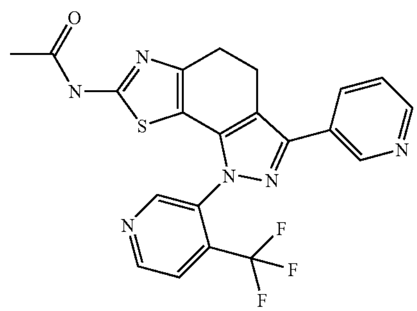 | 457 | 1.54 + 1.71 |
| 1.5 | Z-12 H-10 | 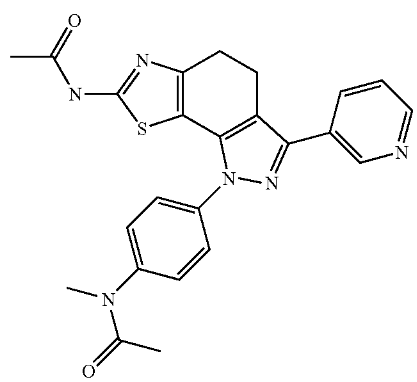 | 459 | 1.45 |
| 1.6 | Z-12 H-11 | 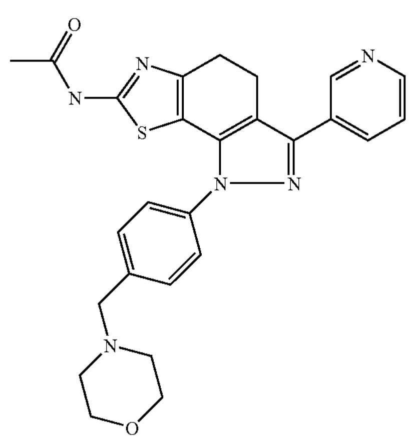 | 487 | 2.53 |

-continued

| # | Starting compound | Structure | Mass [M + 1]+ | HPLC Rt [min] |
|---|---|---|---|---|
| 1.7 | Z-1 | 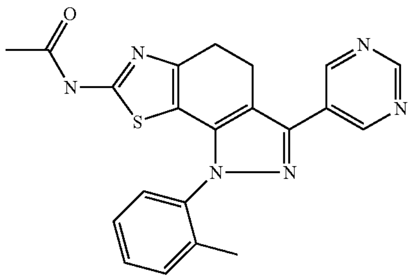 | 403 | 1.81 |
| 1.8 | Z-1 | 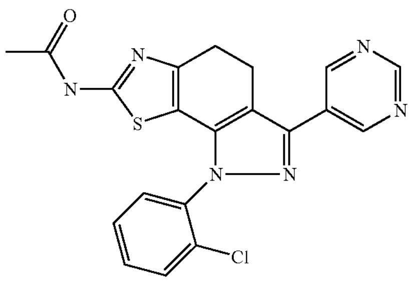 | 423 | 1.82 |
| 1.9 | Z-12 | 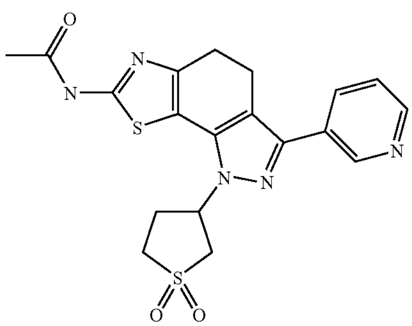 | 430 | 1.53 |
| 1.10 | Z-12 H-13 | 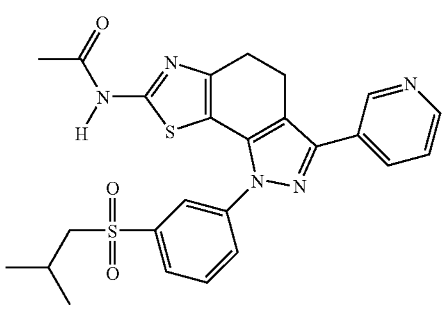 | 508 | 1.67 |
| 1.11 | Z-12 H-14 | 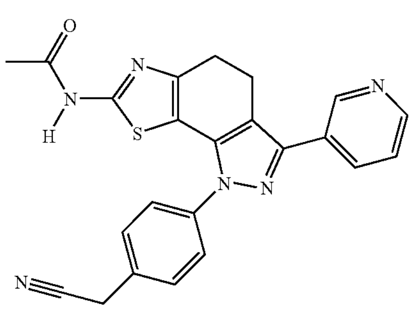 | 427 | 1.49 |

-continued

| # | Starting compound | Structure | Mass [M + 1]+ | HPLC Rt [min] |
|---|---|---|---|---|
| 1.12 | Z-12 H-15 | 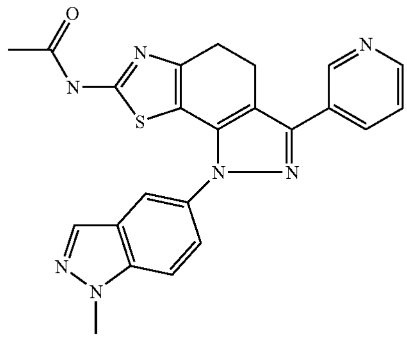 | 442 | 1.48 |
| 1.13 | | 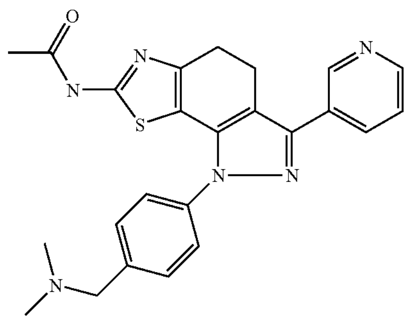 | 445 | 1.19 |

Examples 2

Reacting the Carboxylic Acids with Amines

Synthesis Method A

TBTU (0.15 mmol) and triethylamine (0.65 mmol) are added to a solution of the carboxylic acid (0.1 mmol) in 5 ml of dichloromethane and the mixture is stirred at RT for 15 min. The appropriate amine (0.1 mmol) is then added and the mixture is stirred at RT until the conversion is complete. The reaction mixture is treated with an aqueous 5% solution of potassium carbonate and extracted with dichloromethane. The combined organic phases are dried and evaporated in vacuo. The residue is crystallized from petroleum ether or purified chromatographically.

Synthesis Method B

HATU (0.55 mmol) and diisopropylethylamine (1.8 mmol) are added to a solution of the carboxylic acid (0.35 mmol) in 5 ml of DMF (or dichloromethane or THF) and the mixture is stirred at RT for 15 min. After the appropriate amine (0.39 mmol) has been added, the mixture is stirred at RT for 15 h, after which it is treated with aqueous 5% potassium carbonate solution and extracted with dichloromethane. The combined organic phases are dried and evaporated in vacuo. The residue is purified chromatographically.

Synthesis Method C

The synthesis is carried out in analogy with synthesis method B but using triethylamine instead of diisopropylethylamine.

Synthesis Method D

The carboxylic acid is first of all immobilized on a polymer. For this, 12 ml of dichloromethane are added to 1.2 g of PL-TFP resin (1.25 mmol/g, 150-300 μm; Polymer Laboratories), with the appropriate carboxylic acid (1.2 mmol in 6 ml of DMF), DMAP (0.7 mmol in 6 ml of dichloromethane) and 0.8 ml of diisopropylcarbodiimide then being pipetted in consecutively 5 minutes later. The mixture is left to stand at RT for 36 h. The resin is filtered off through a glass frit (porosity 4) and washed 4× with in each case 15 ml of DMF, 4× with in each case 20 ml of dichloromethane and 4× with in each case 20 ml of THF, with the solvent in each case dripping through the glass frit without any vacuum/pressure and with the frit being sucked dry before each new application of solvent. The washed resin is dried at RT and 0.2 mbar for 2 d. Yield of dry resin: 2.204 g.

For the reaction of the immobilized carboxylic acid, 110 mg (0.15 mmol) of the resin which has been prepared in this way are initially introduced in 1 ml of dichloromethane and 0.5 ml of DMF after which the amine (0.1 mmol) and diisopropylethylamine (0.1 mmol) are added. The mixture is then stirred slowly at RT for 15 h. After the reaction has come to an end, the resin is filtered off as described above and washed with 8×3 ml of dichloromethane. The filtrate is evaporated in vacuo and the residue is purified by means of RP-HPLC.

Examples 2.1-2.183

| # | Starting compound | Structure | Mass [M + 1]⁺ | HPLC Rt [min] or m.p. or TLC:R$_f$ |
|---|---|---|---|---|
| 2.1 | I-9 | (structure) | 534 | 2.06 |

¹H-NMR DMSO-d6, d [ppm]: 7.86 (s, 1H), 7.78 (d, 7.9 Hz, 1H), 7.75 (d, 7.7 Hz, 1H), 7.63-7.61 (m, 1H), 7.49-7.46 (m, 2H), 7.41-7.37 (m, 1H), 3.72-3.62 (m, 6H), 3.42-3.38 (m, 2H), 2.07 (s, 3H).

| # | Starting compound | Structure | Mass [M + 1]⁺ | HPLC Rt [min] or m.p. or TLC:R$_f$ |
|---|---|---|---|---|
| 2.5 | I-9 | (structure) | 478 | m.p.: 206° C. |
| 2.6 | I-9 | (structure) | 540 | R$_f$ = 0.5 DCM:MeOH 9:1 |

| # | Starting compound | Structure | Mass [M + 1]+ | HPLC Rt [min] or m.p. or TLC:R_f |
|---|---|---|---|---|
| 2.7 | I-9 | 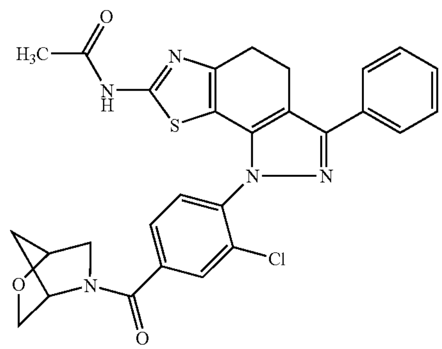 | 546 | 1.94 |
| 2.8 | I-9 | 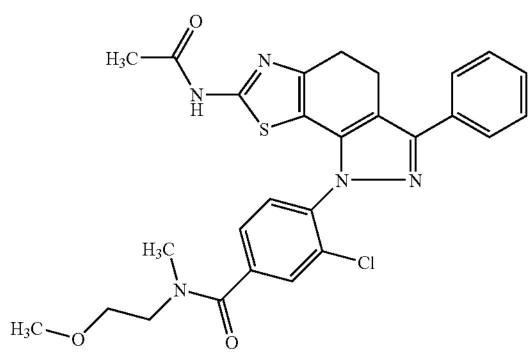 | 536 | 2.1 |
| 2.9 | I-9 | 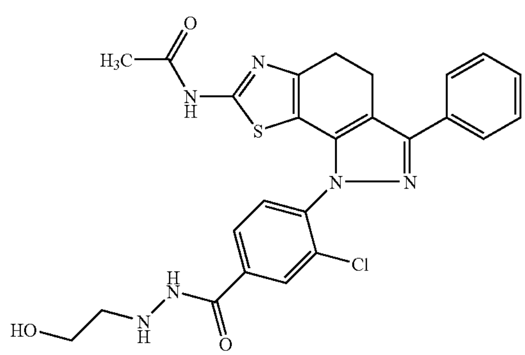 | 523 | 1.88 |
| 2.10 | I-9 | 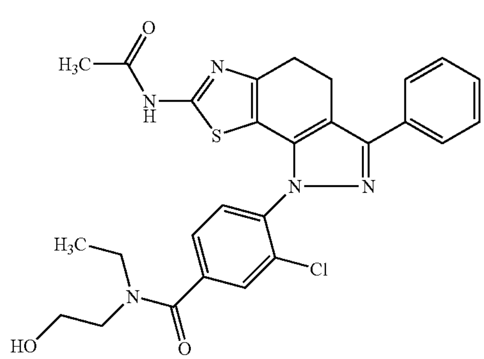 | 536 | 2.02 |

-continued

| # | Starting compound | Structure | Mass [M + 1]+ | HPLC Rt [min] or m.p. or TLC:R$_f$ |
|---|---|---|---|---|
| 2.11 | I-21 | 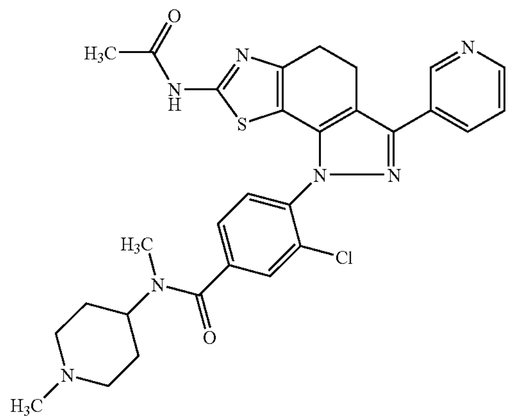 | 576 | 2.06 |
| 2.12 | I-21 | 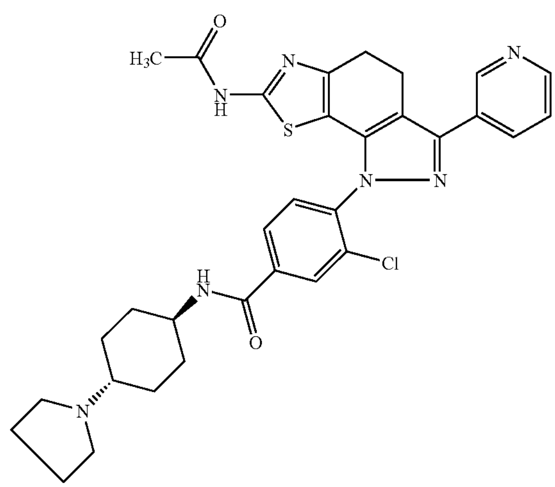 | 616 | 1.4 |
| 2.13 | I-21 | 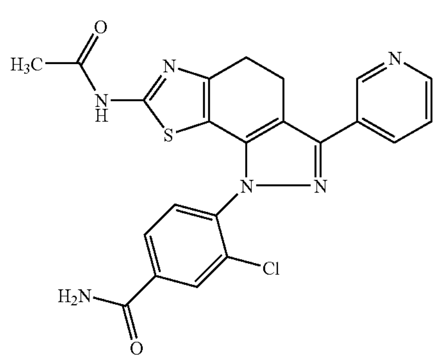 | 465 | 1.42 |

-continued

| # | Starting compound | Structure | Mass [M + 1]+ | HPLC Rt [min] or m.p. or TLC:R_f |
|---|---|---|---|---|
| 2.14 | I-21 | 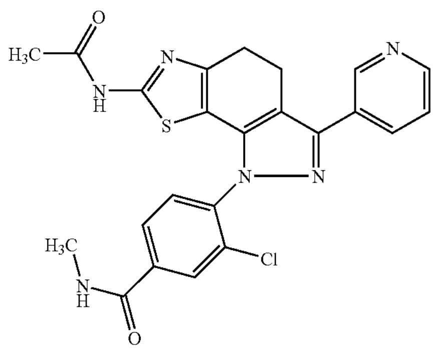 | 479 | 2.18 |
| 2.15 | I-21 | 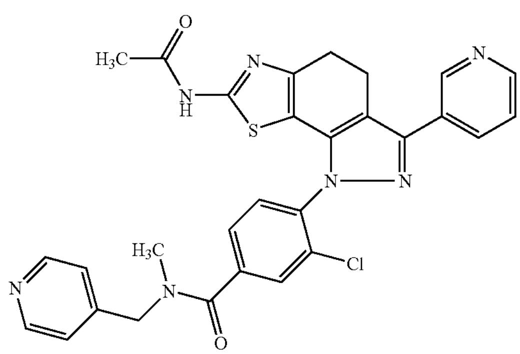 | 570 | 2.02 |
| 2.16 | I-21 | 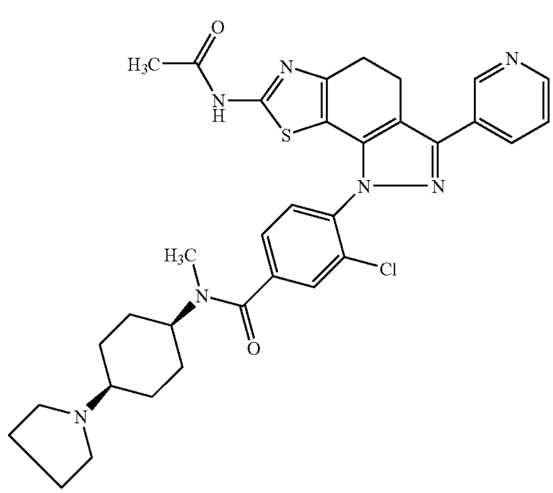 | 630 | 1.39 |

-continued

| # | Starting compound | Structure | Mass [M + 1]⁺ | HPLC Rt [min] or m.p. or TLC:R_f |
|---|---|---|---|---|
| 2.17 | I-21 | 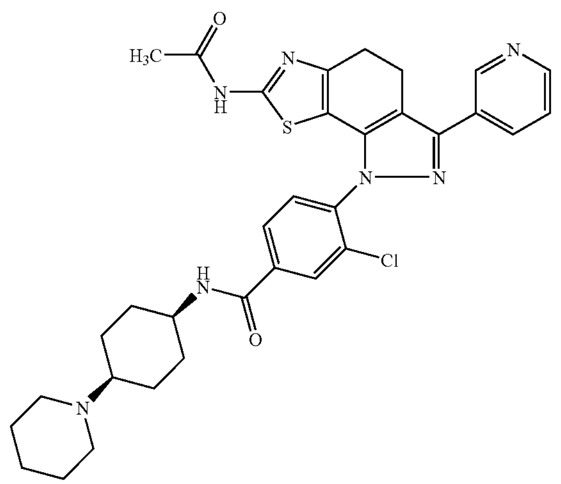 | 630 | 1.28 |
| 2.18* | I-21 | 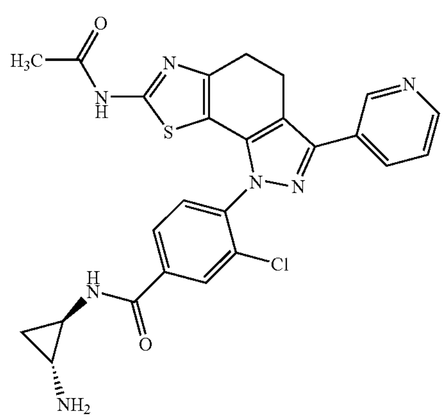 | 520 | 1.98 |
| 2.19 | I-21 | 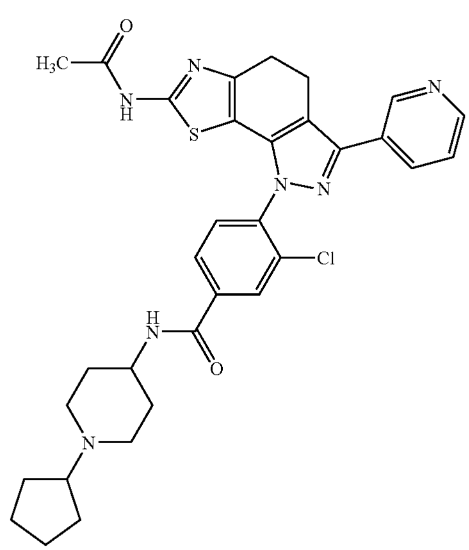 | 616 | 1.32 |

-continued
| # | Starting compound | Structure | Mass [M + 1]+ | HPLC Rt [min] or m.p. or TLC:R_f |
|---|---|---|---|---|
| 2.20 | I-21 | 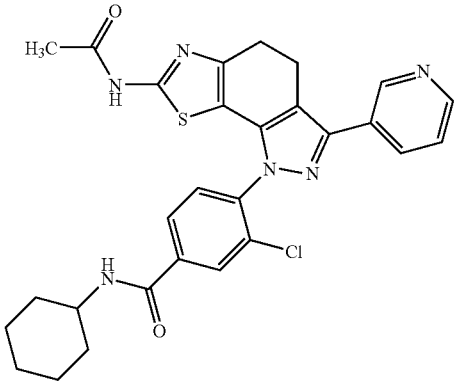 | 547 | 1.89 |
| 2.21 | I-21 | 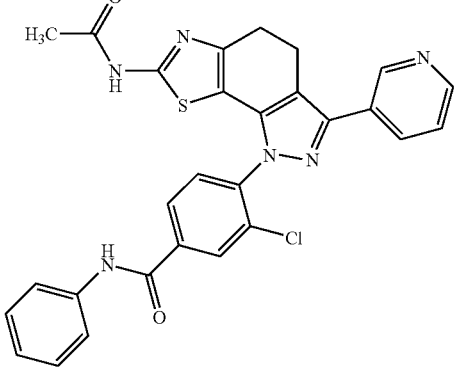 | 541 | 1.86 |
| 2.22 | I-21 | 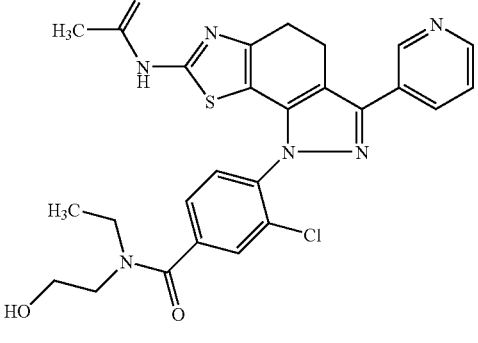 | 537 | 1.54 |
| 2.23 | I-21 | 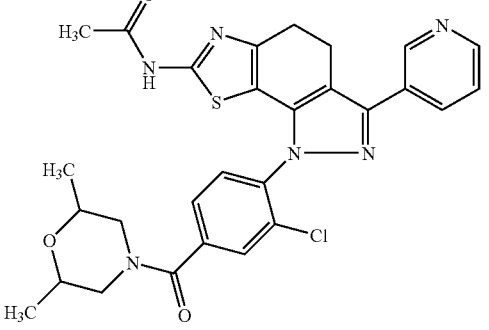 | 563 | 3.2 |

-continued
| # | Starting compound | Structure | Mass [M + 1]+ | HPLC Rt [min] or m.p. or TLC:R_f |
|---|---|---|---|---|
| 2.24 | I-21 | 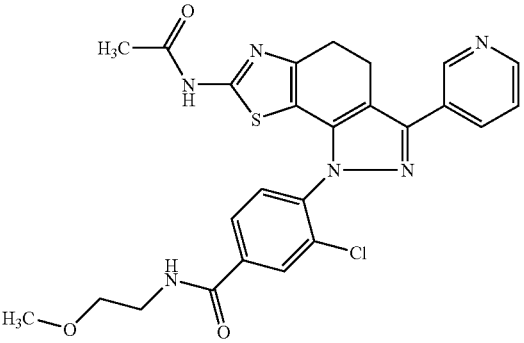 | 523 | 1.58 |
| 2.25 | I-21 | 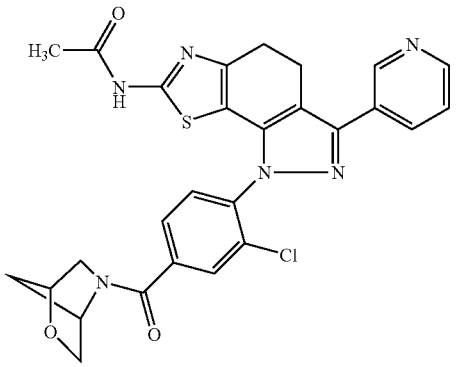 | 547 | 1.5 |
| 2.26 | I-21 | 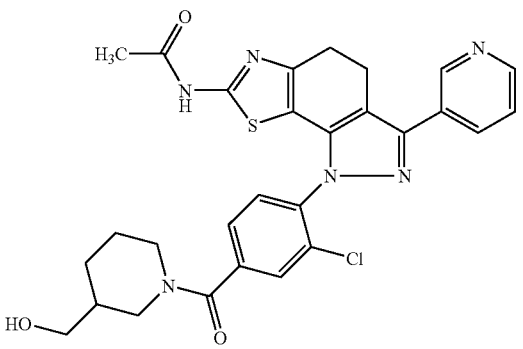 | 563 | 1.6 |
| 2.27 | I-21 | 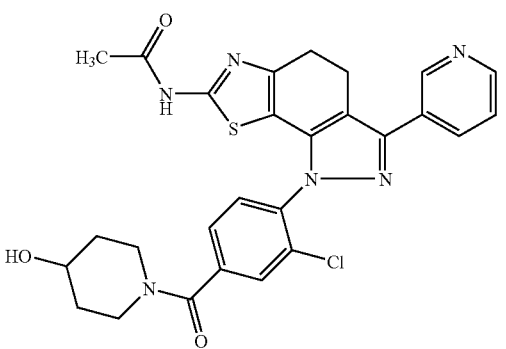 | 549 | 1.45 |

-continued

| # | Starting compound | Structure | Mass [M + 1]⁺ | HPLC Rt [min] or m.p. or TLC:R_f |
|---|---|---|---|---|
| 2.28 | I-21 | 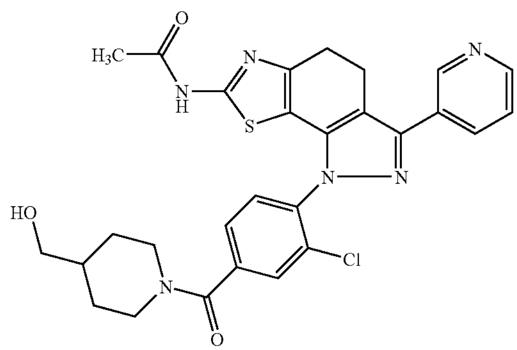 | 563 | 1.55 |
| 2.29 | I-21 | 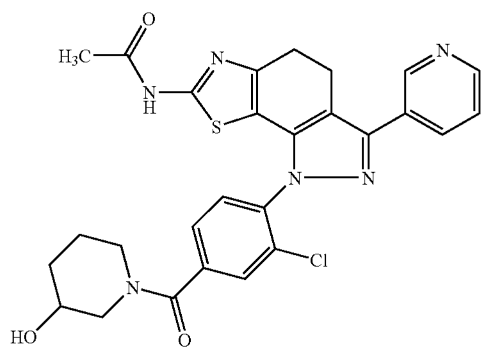 | 549 | 1.53 |
| 2.30 | I-21 | 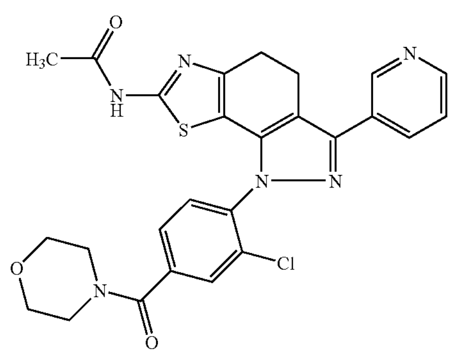 | 535 | 1.58 |
| 2.31 | I-21 | 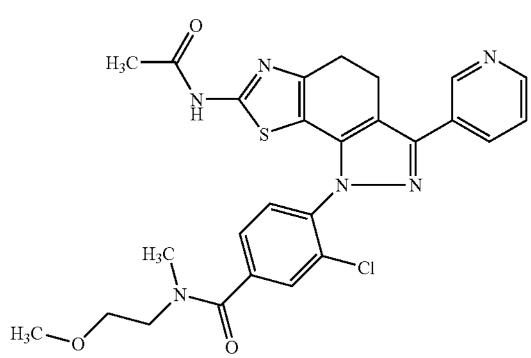 | 537 | 1.58 |

-continued

| # | Starting compound | Structure | Mass [M + 1]⁺ | HPLC Rt [min] or m.p. or TLC:R_f |
|---|---|---|---|---|
| 2.32 | I-21 | 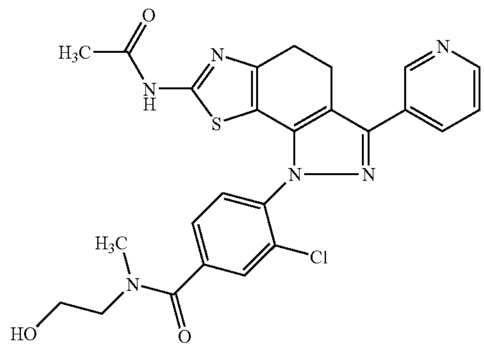 | 523 | 1.47 |
| 2.33 | I-21 | 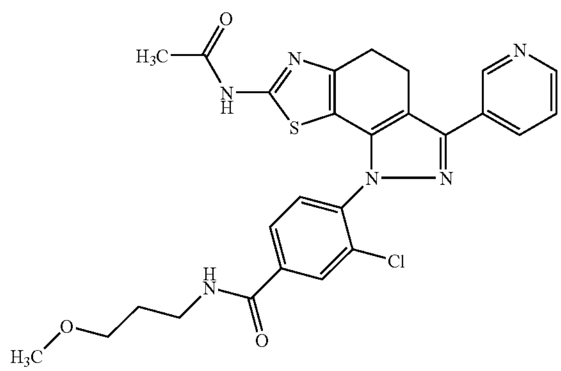 | 537 | 1.58 |
| 2.34 | I-21 | 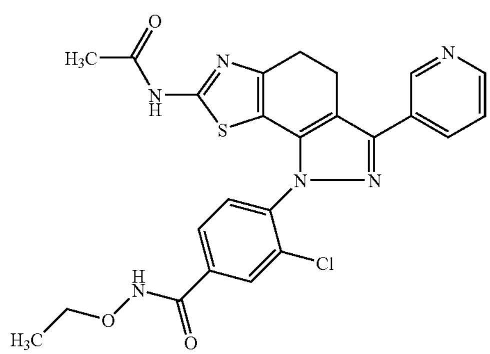 | 509 | 1.5 |
| 2.35 | I-21 | 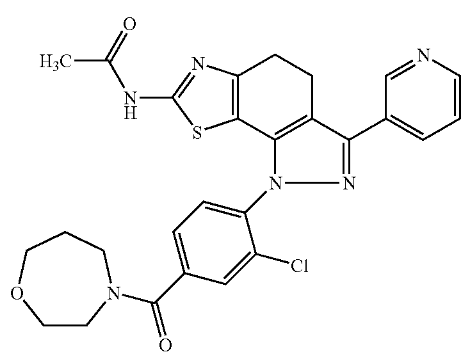 | 549 | 1.55 |

-continued

| # | Starting compound | Structure | Mass [M + 1]⁺ | HPLC Rt [min] or m.p. or TLC:R_f |
|---|---|---|---|---|
| 2.36 | I-21 | 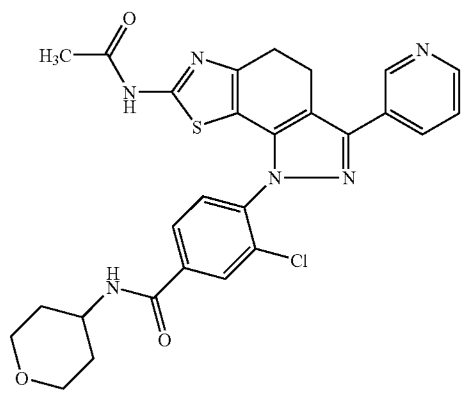 | 549 | 1.59 |
| 2.37 | I-21 | 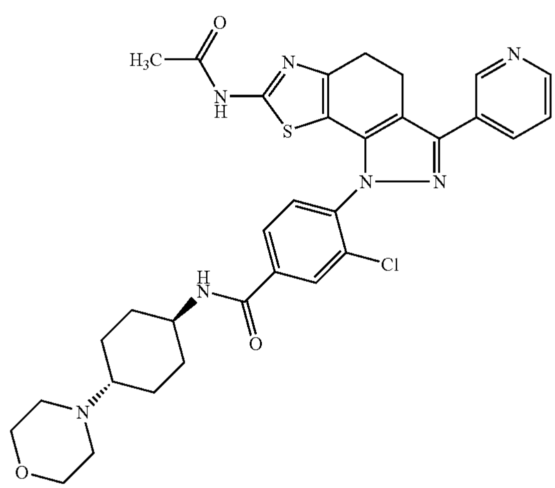 | 632 | 0.55 |
| 2.38 | I-21 | 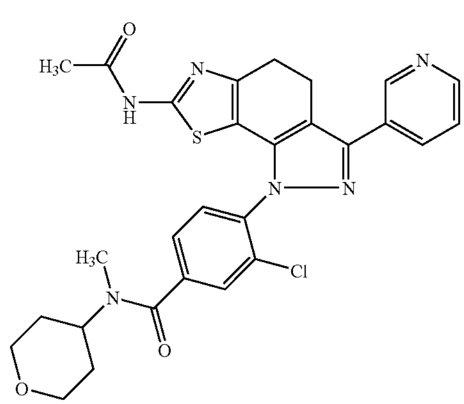 | 563 | 1.53 |

-continued

| # | Starting compound | Structure | Mass [M + 1]⁺ | HPLC Rt [min] or m.p. or TLC:R_f |
|---|---|---|---|---|
| 2.39 | I-21 | 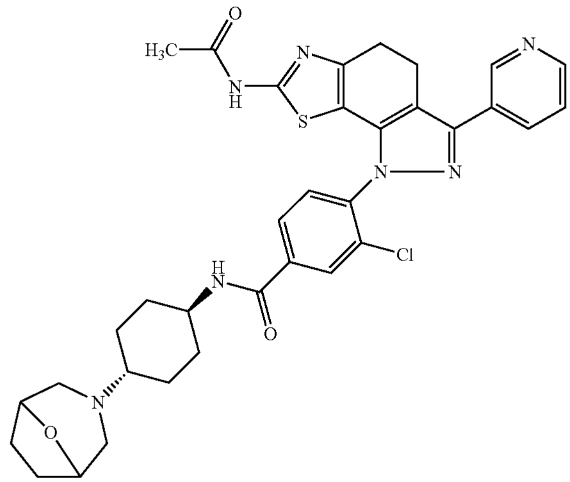 | 658 | 0.52 |
| 2.40 | I-21 | 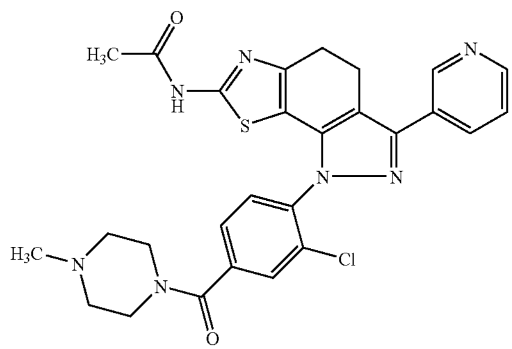 | 548 | 2.53 |
| 2.41 | I-21 | 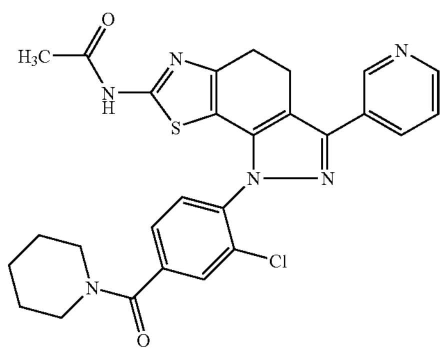 | 533 | 1.76 |
| 2.42 | I-21 | 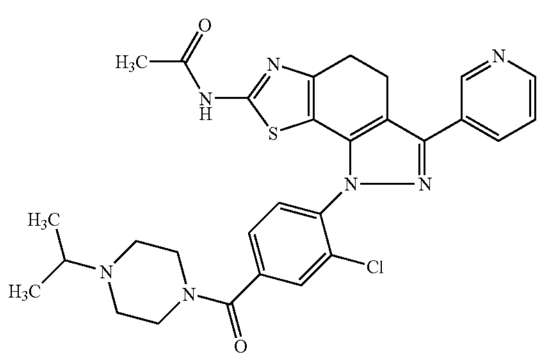 | 576 | 2.57 |

-continued

| # | Starting compound | Structure | Mass [M + 1]⁺ | HPLC Rt [min] or m.p. or TLC:R$_f$ |
|---|---|---|---|---|
| 2.43 | I-21 | 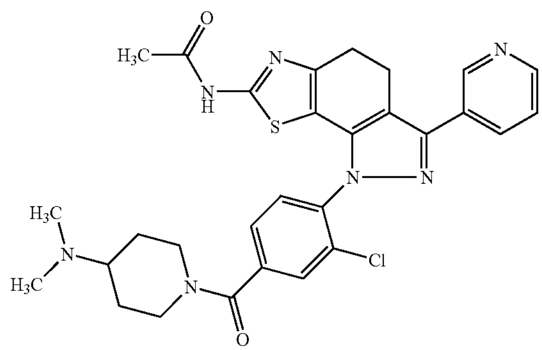 | 576 | 2.56 |
| 2.44 | I-21 | 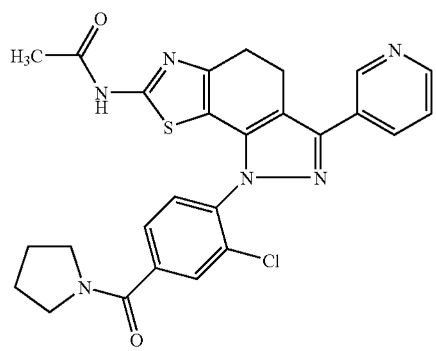 | 519 | 1.62 |
| 2.45 | I-21 | 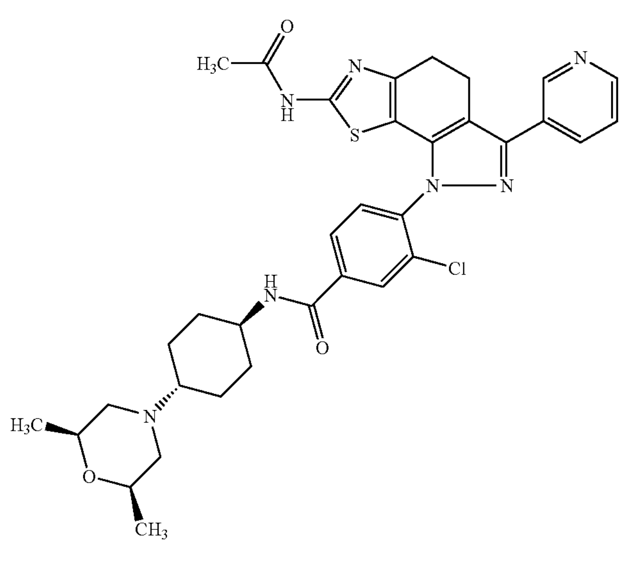 | 660 | 1.39 |

-continued
| # | Starting compound | Structure | Mass [M + 1]+ | HPLC Rt [min] or m.p. or TLC:R_f |
|---|---|---|---|---|
| 2.46 | I-21 | 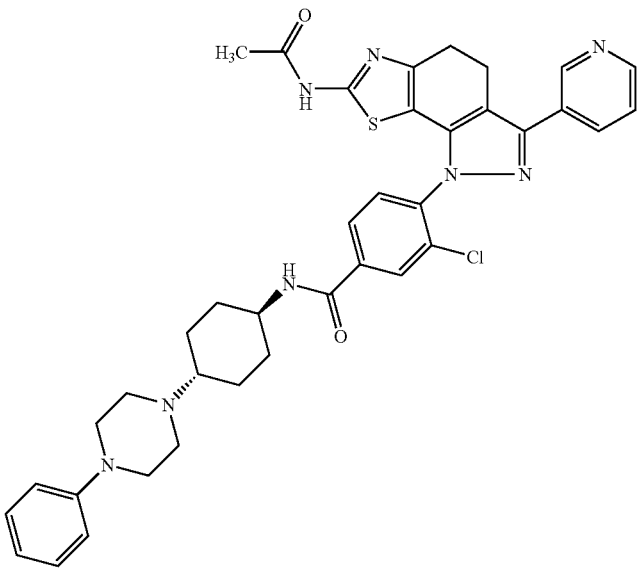 | 707 | 1.5 |
| 2.47 | I-21 | 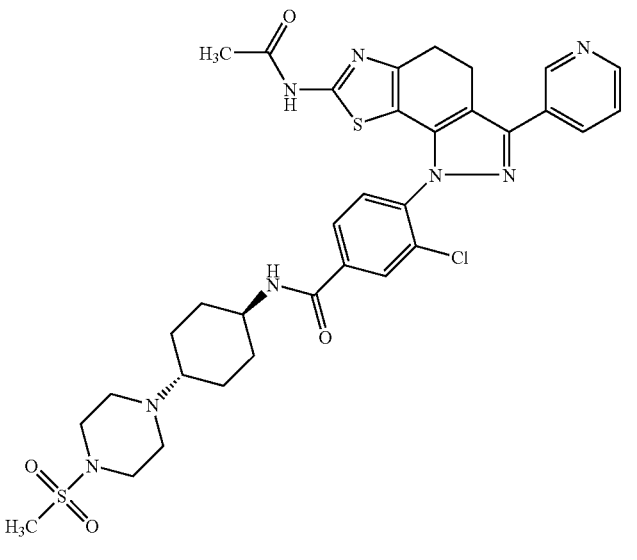 | 709 | 2.75 |

-continued

| # | Starting compound | Structure | Mass [M + 1]+ | HPLC Rt [min] or m.p. or TLC:R_f |
|---|---|---|---|---|
| 2.48 | I-21 | 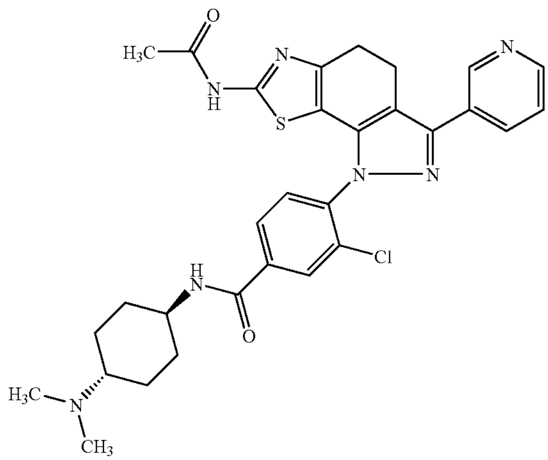 | 590 | 2.69 |
| 2.49 | I-21 | 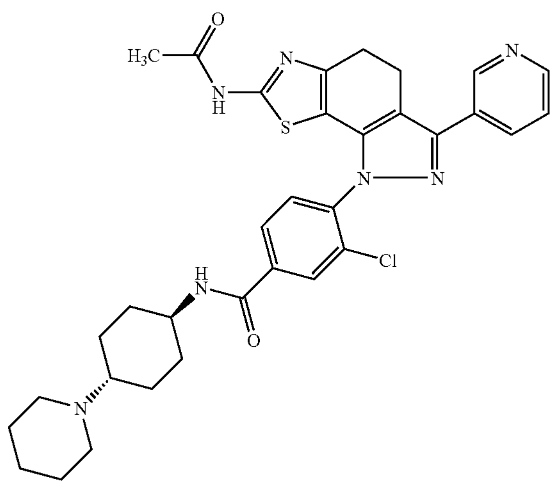 | 630 | 2.77 |
| 2.50 | I-21 | 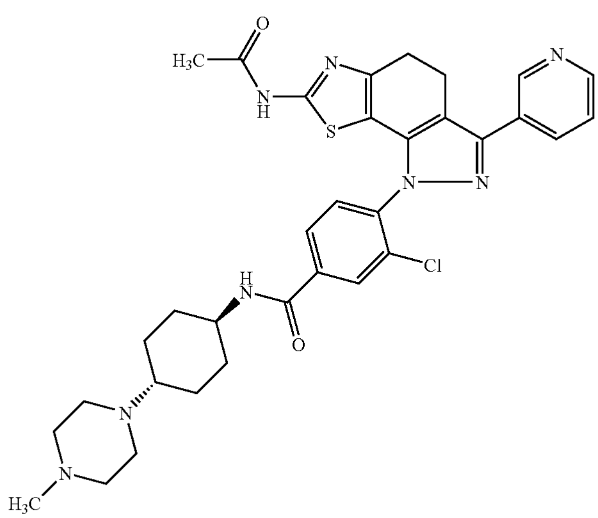 | 645 | 2.56 |

-continued

| # | Starting compound | Structure | Mass [M + 1]+ | HPLC Rt [min] or m.p. or TLC:R_f |
|---|---|---|---|---|
| 2.51 | I-20 | 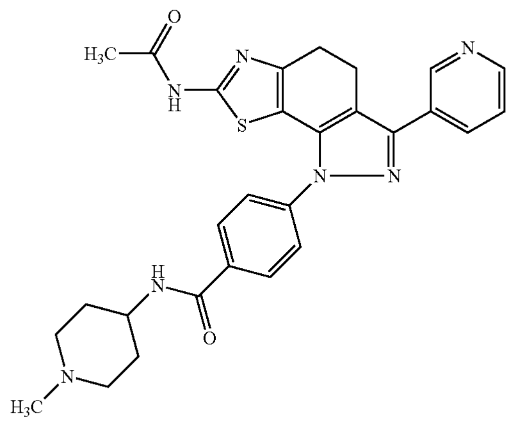 | 528 | 2 |
| 2.52 | I-20 | 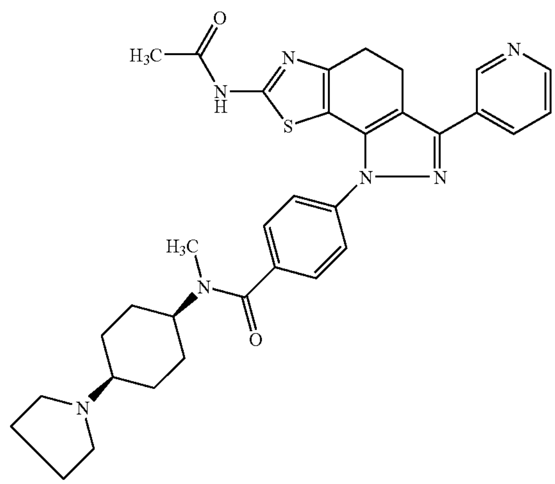 | 596 | 2.11 |
| 2.53 | I-20 | 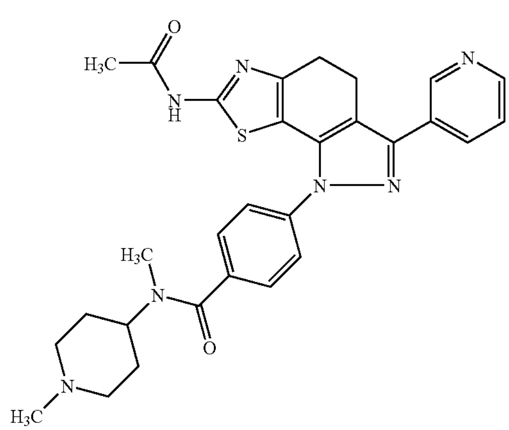 | 542 | 2.06 |

-continued

| # | Starting compound | Structure | Mass [M + 1]+ | HPLC Rt [min] or m.p. or TLC:Rf |
|---|---|---|---|---|
| 2.54 | I-20 | 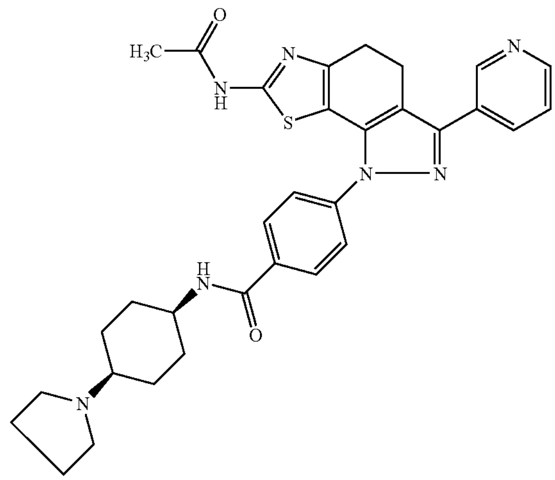 | 582 | 2.1 |
| 2.55 | I-20 | 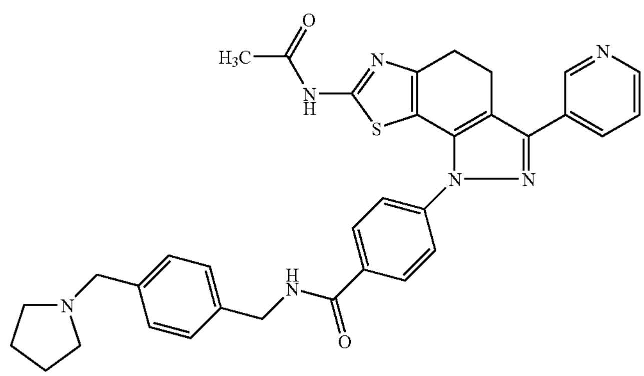 | 604 | 1.26 |
| 2.56 | I-20 | 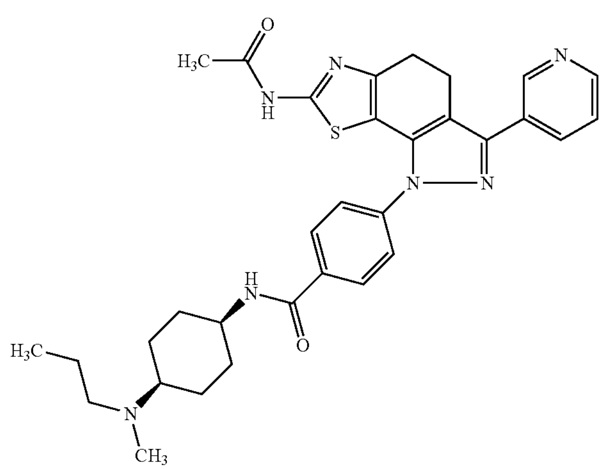 | 584 | 1.33 |

-continued

| # | Starting compound | Structure | Mass [M + 1]⁺ | HPLC Rt [min] or m.p. or TLC:R_f |
|---|---|---|---|---|
| 2.57 | I-20 | 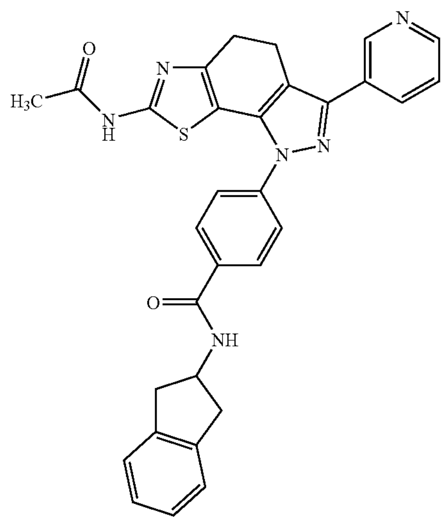 | 547 | 1.88 |
| 2.58 | I-20 | 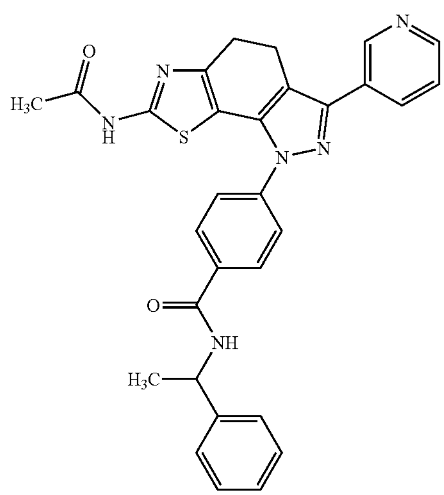 | 535 | 1.84 |
| 2.59 | I-20 | 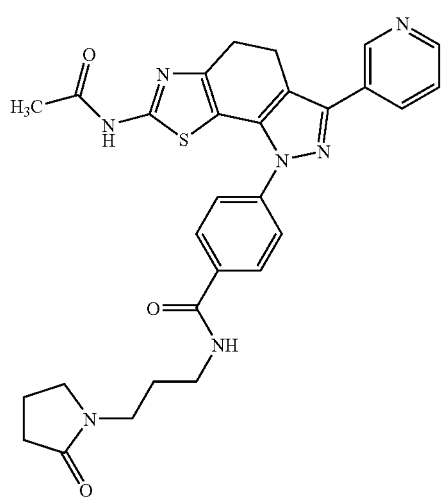 | 556 | 1.5 |

-continued

| # | Starting compound | Structure | Mass [M + 1]⁺ | HPLC Rt [min] or m.p. or TLC:R$_f$ |
|---|---|---|---|---|
| 2.60 | I-20 | 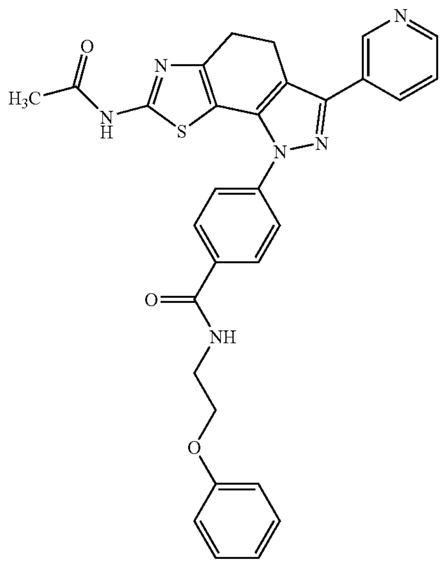 | 551 | 1.83 |
| 2.61 | I-22 | 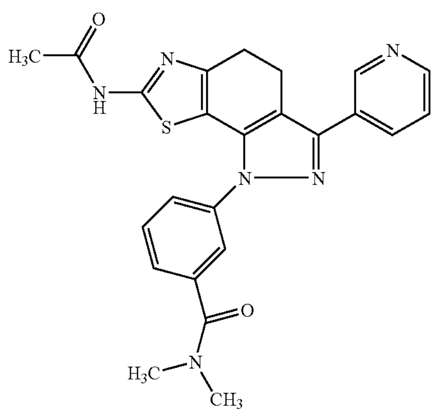 | 459 | 1.43 |
| 2.62 | I-23 | 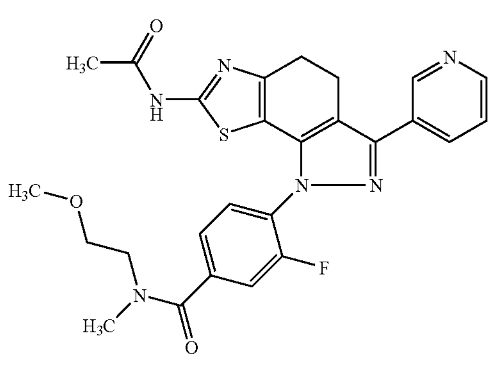 | 521 | 1.54 |

-continued

| # | Starting compound | Structure | Mass [M + 1]+ | HPLC Rt [min] or m.p. or TLC:R_f |
|---|---|---|---|---|
| 2.63 | I-23 | 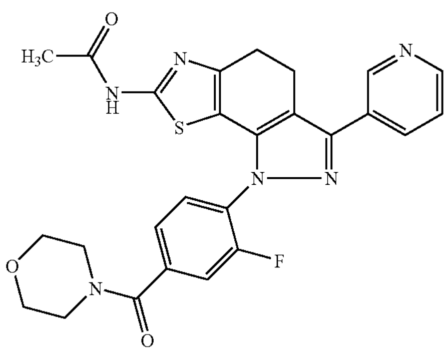 | 519 | 1.49 |
| 2.64 | I-23 | 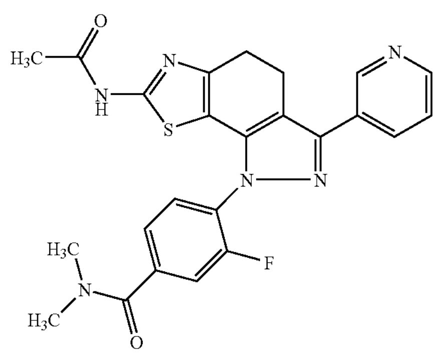 | 477 | 1.43 |
| 2.65 | I-23 | 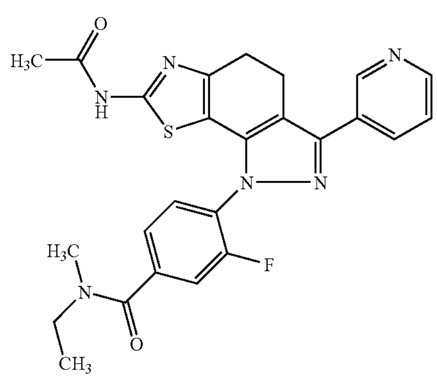 | 491 | 1.59 |
| 2.66 | I-23 | 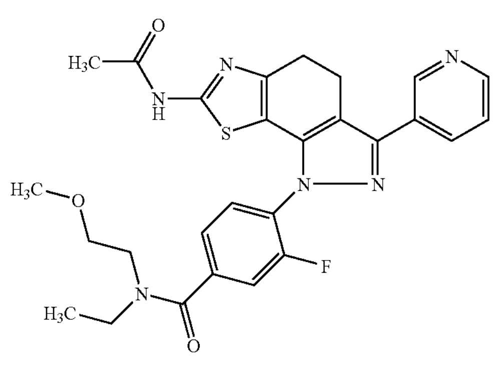 | 535 | 1.63 |

| # | Starting compound | Structure | Mass [M + 1]⁺ | HPLC Rt [min] or m.p. or TLC:R_f |
|---|---|---|---|---|
| 2.67 | I-23 | 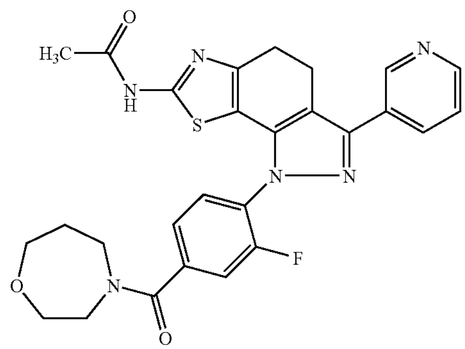 | 533 | 1.54 |
| 2.68 | I-25 | 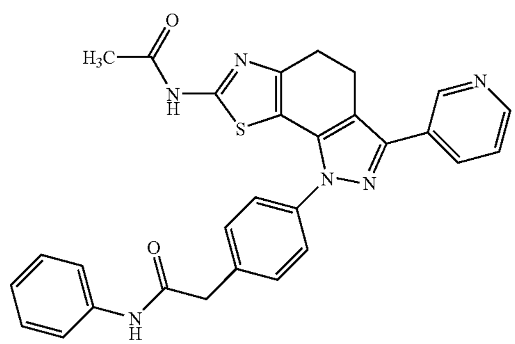 | 521 | 1.75 |
| 2.69 | I-25 | 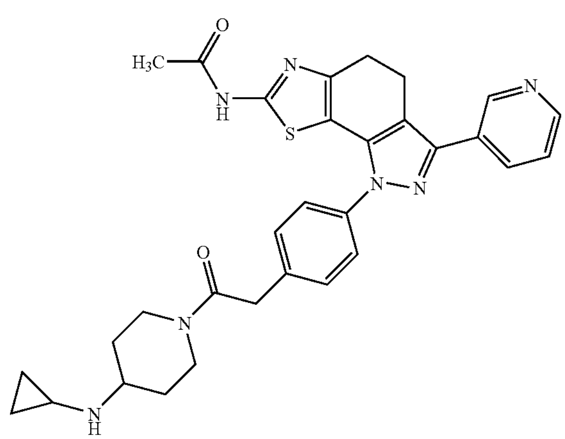 | 568 | 0.19 |

-continued
| # | Starting compound | Structure | Mass [M + 1]⁺ | HPLC Rt [min] or m.p. or TLC:R_f |
|---|---|---|---|---|
| 2.70 | I-25 | 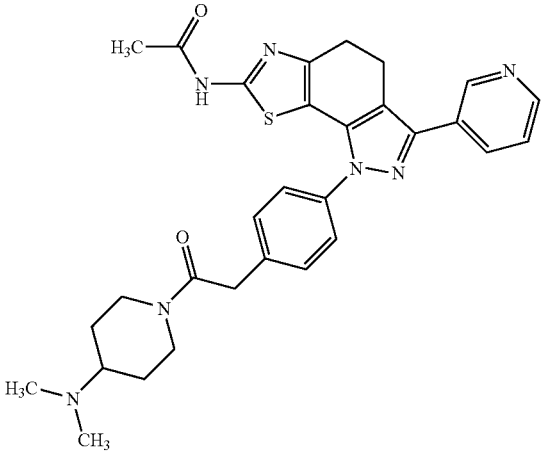 | 556 | Rf: 0.14 DCM:MeOH 7:3 |
| 2.71 | I-25 | 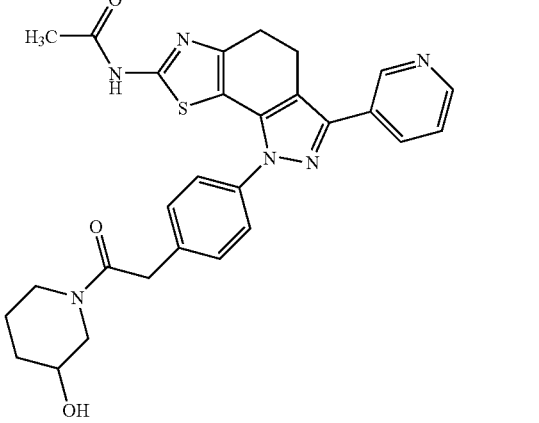 | 529 | 1.5 |
| 2.72 | I-25 | 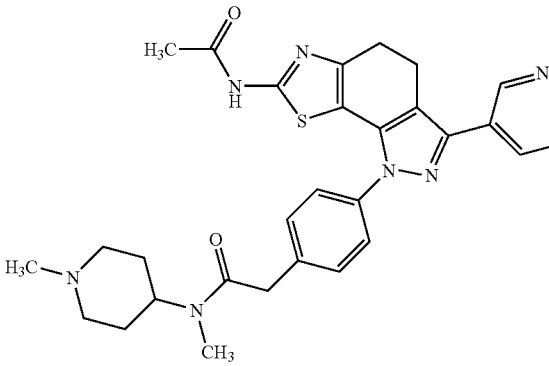 | 556 | R_f = 0.18 DCM:MeOH 7:3 |

-continued

| # | Starting compound | Structure | Mass [M + 1]+ | HPLC Rt [min] or m.p. or TLC:R_f |
|---|---|---|---|---|
| 2.73 | I-25 | 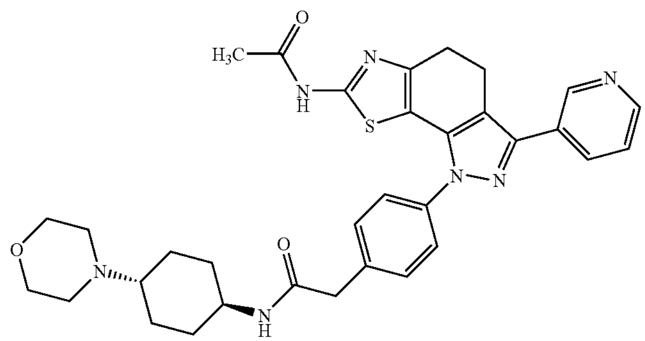 | 612 | R_f = 0.27 DCM:MeOH 8:2 |
| 2.74 | I-25 | 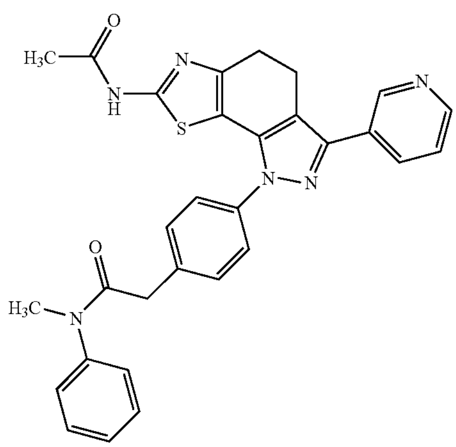 | 535 | 1.81 |
| 2.75 | I-25 | 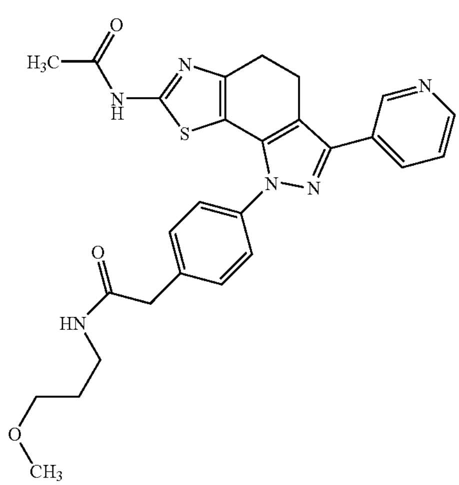 | 517 | 1.53 |

-continued
| # | Starting compound | Structure | Mass [M + 1]+ | HPLC Rt [min] or m.p. or TLC:R_f |
|---|---|---|---|---|
| 2.76 | I-25 | 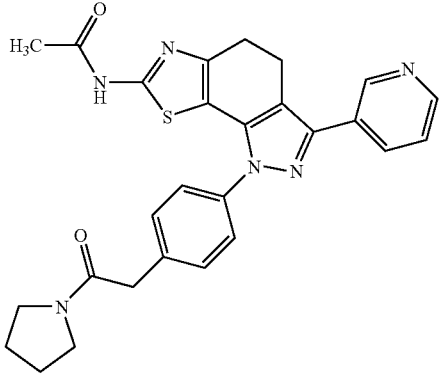 | 499 | 1.6 |
| 2.77 | I-25 | 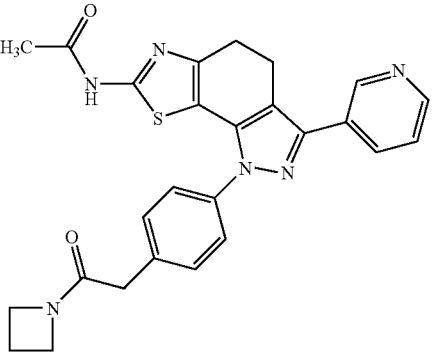 | 485 | 1.48 |
| 2.78 | I-25 | 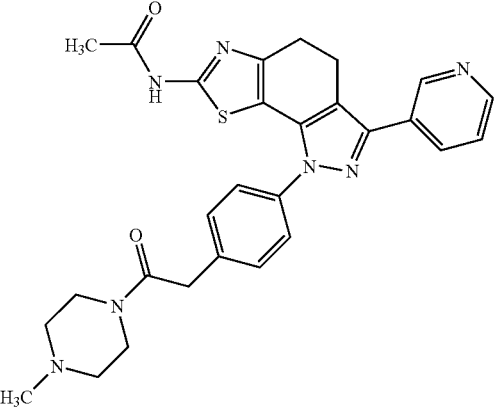 | 528 | 2.8 |

-continued

| # | Starting compound | Structure | Mass [M + 1]⁺ | HPLC Rt [min] or m.p. or TLC:R_f |
|---|---|---|---|---|
| 2.79 | I-25 | 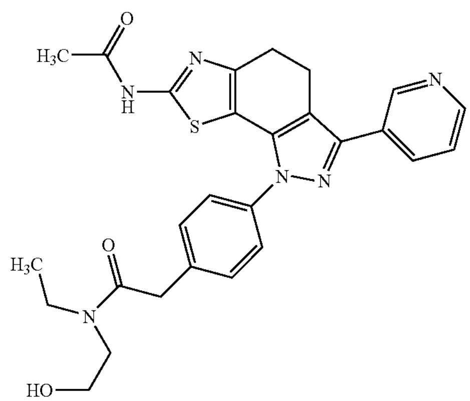 | 517 | 1.51 |
| 2.80 | I-25 EtOH | 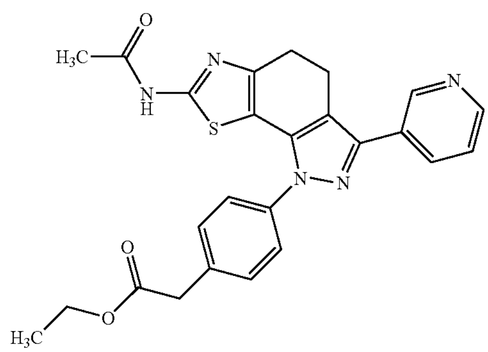 | 474 | 3.38 |
| 2.81 | I-26 | 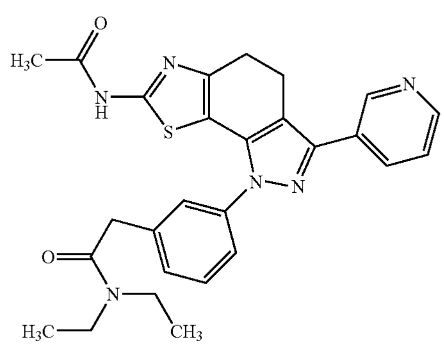 | 501 | 1.64 |
| 2.82 | I-27 | 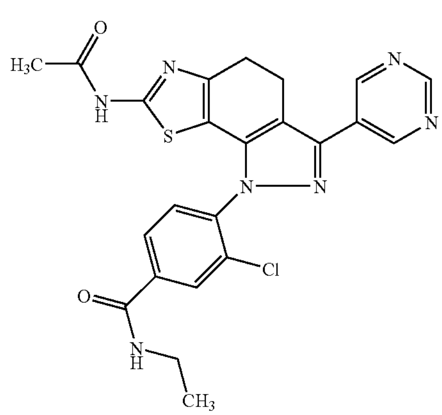 | 494 | 1.74 |

-continued

| # | Starting compound | Structure | Mass [M + 1]+ | HPLC Rt [min] or m.p. or TLC:R$_f$ |
|---|---|---|---|---|
| 2.83 | I-28 | 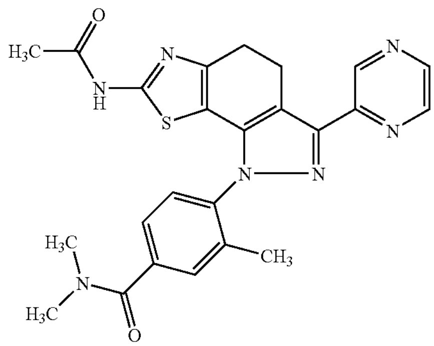 | 474 | m.p.: 283° C. |
| 2.84 | I-45 | 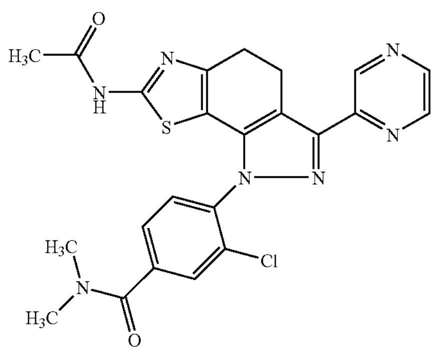 | 494 | 1.81 |
| 2.85 | I-12 | 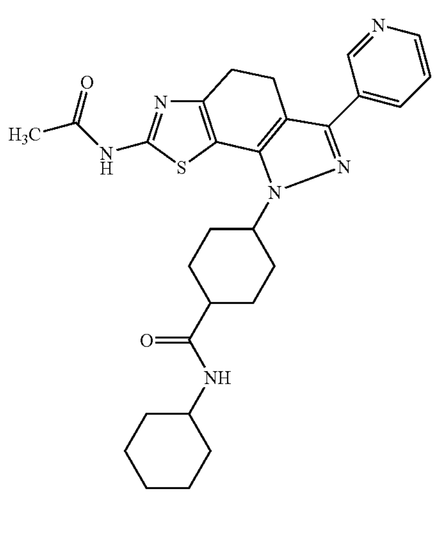 | 519 | 1.77 |

-continued

| # | Starting compound | Structure | Mass [M + 1]+ | HPLC Rt [min] or m.p. or TLC:R_f |
|---|---|---|---|---|
| 2.86 | I-12 | 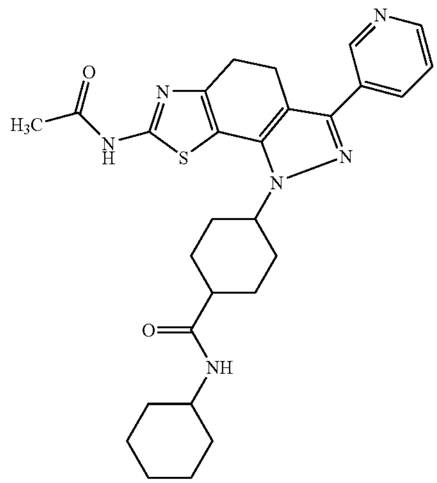 | 507 | 1.47 |
| 2.87 | I-12 | 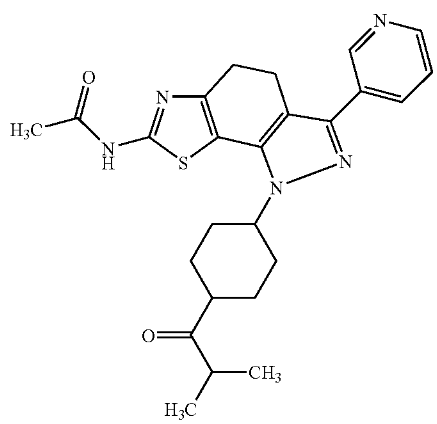 | 465 | 1.39 |
| 2.88 | I-36 | 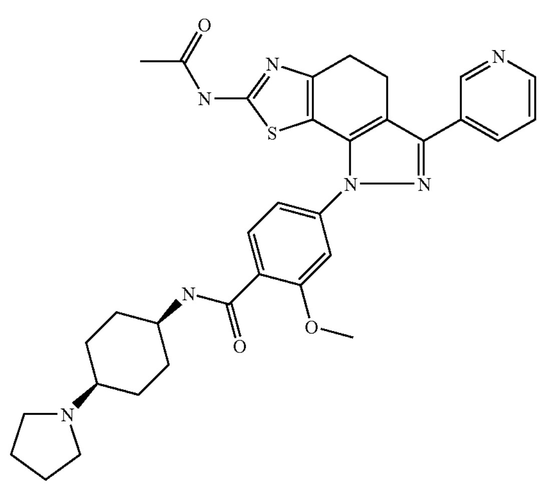 | 612 | 1.35 |

-continued

| # | Starting compound | Structure | Mass [M + 1]⁺ | HPLC Rt [min] or m.p. or TLC:R_f |
|---|---|---|---|---|
| 2.89 | I-36 | 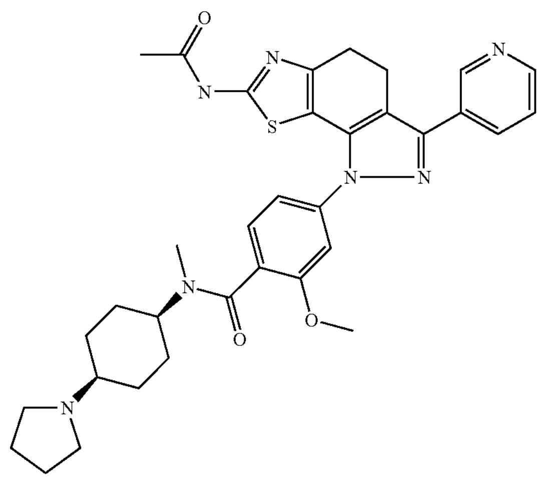 | 626 | 1.33 |
| 2.90 | I-36 | 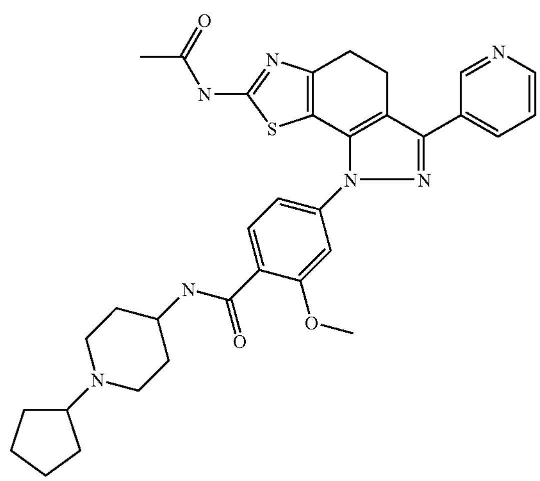 | 612 | 1.38 |
| 2.91 | I-36 | 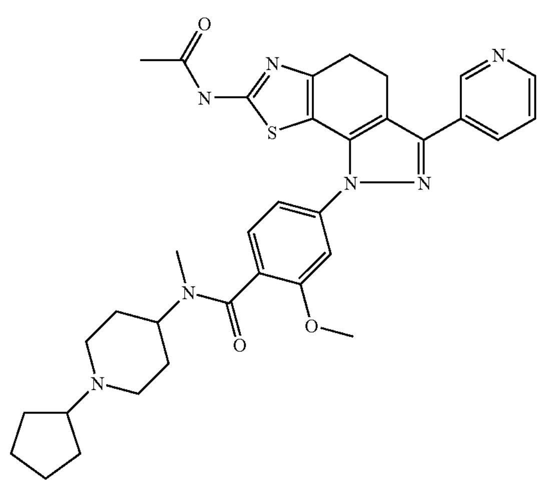 | 626 | 1.36 |

-continued

| # | Starting compound | Structure | Mass [M + 1]⁺ | HPLC Rt [min] or m.p. or TLC:R_f |
|---|---|---|---|---|
| 2.92 | I-36 | 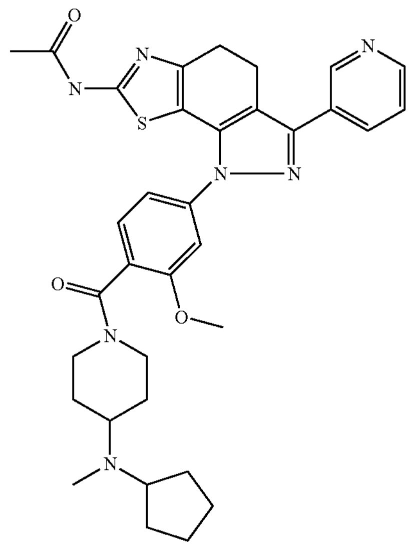 | 626 | 1.37 |
| 2.93 | I-37 | 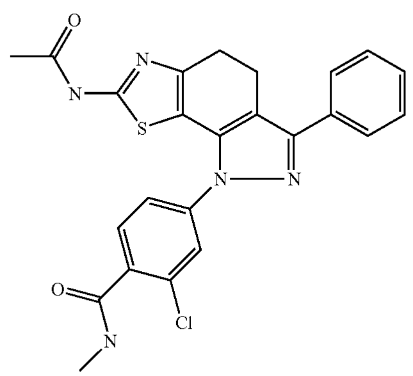 | 478 | 2.00 |
| 2.94 | I-37 | 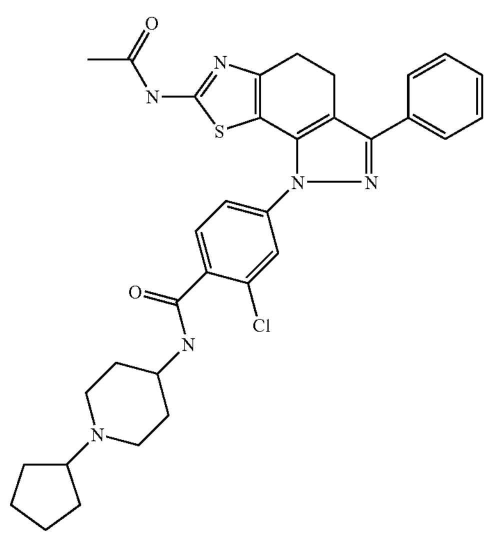 | 615 | 1.67 |

-continued

| # | Starting compound | Structure | Mass [M + 1]+ | HPLC Rt [min] or m.p. or TLC:R_f |
|---|---|---|---|---|
| 2.95 | I-37 | 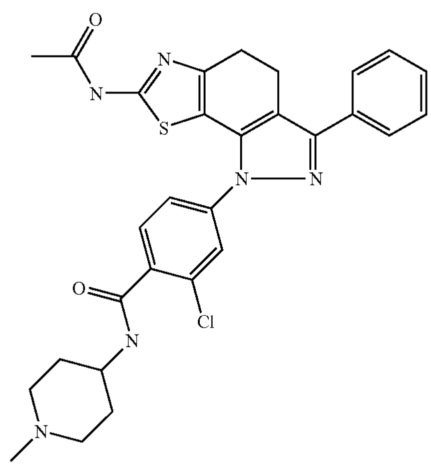 | 561 | 1.60 |
| 2.96 | I-37 | 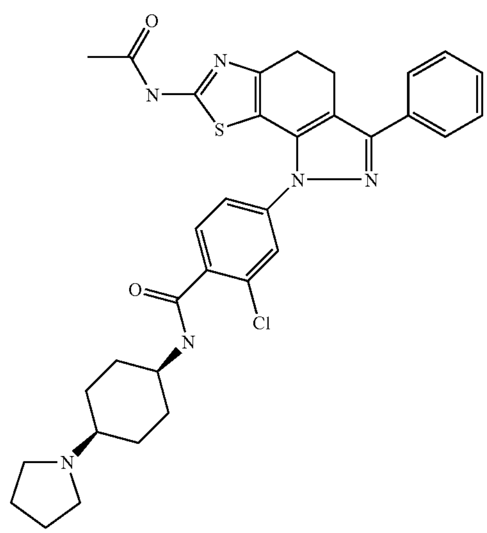 | 615 | 1.65 |
| 2.97 | I-37 | 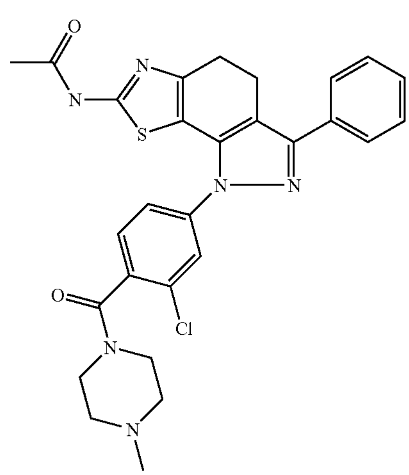 | 547 | 1.60 |

-continued

| # | Starting compound | Structure | Mass [M + 1]+ | HPLC Rt [min] or m.p. or TLC:R$_f$ |
|---|---|---|---|---|
| 2.98 | I-37 | 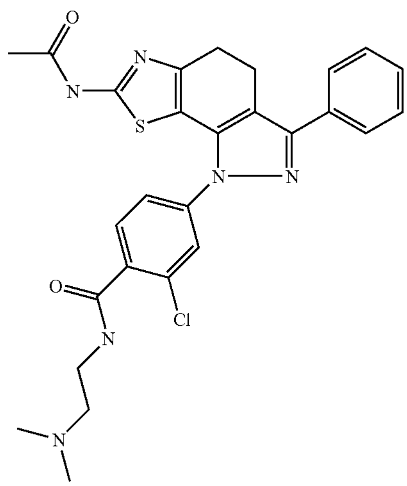 | 535 | 1.60 |
| 2.99 | I-9 | 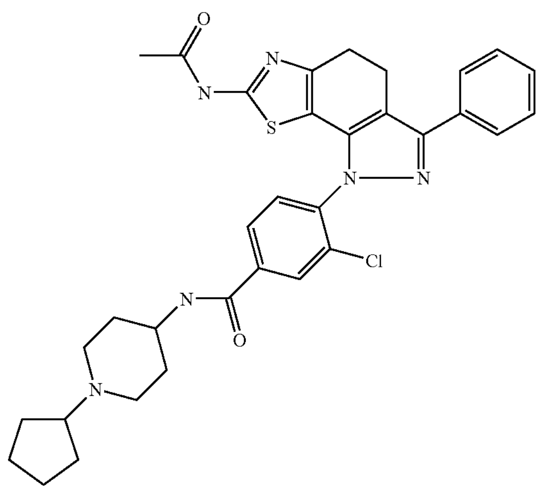 | 615 | m.p.: 280° C. |
| 2.100 | I-9 | 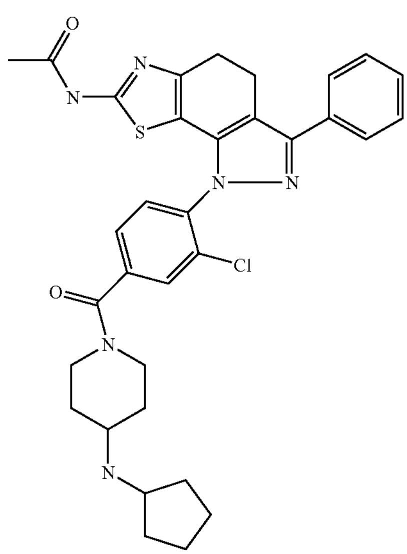 | 629 | m.p.: 286° C. |

-continued
| # | Starting compound | Structure | Mass [M + 1]+ | HPLC Rt [min] or m.p. or TLC:R$_f$ |
|---|---|---|---|---|
| 2.101 | I-12 | 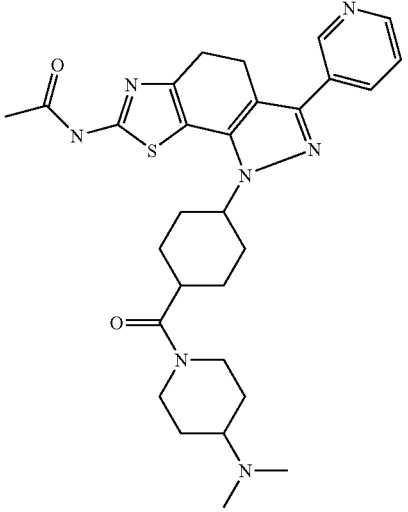 | 548 | 1.45 |
| 2.102 | I-12 | 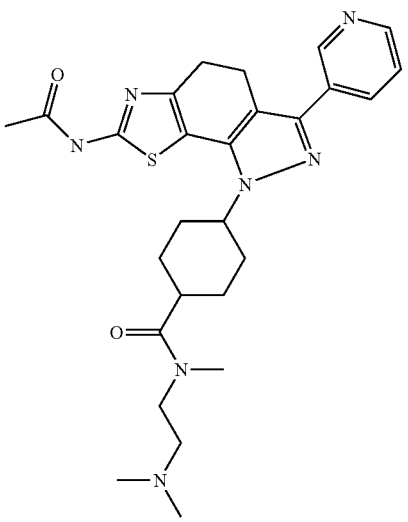 | 522 | 1.46 |
| 2.103 | trans-I-12 | 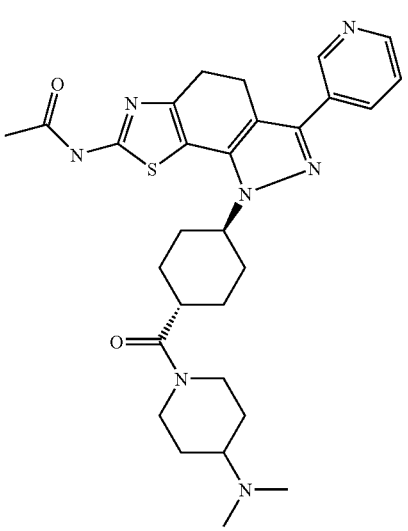 | 548 | 1.43 |

-continued
| # | Starting compound | Structure | Mass [M + 1]+ | HPLC Rt [min] or m.p. or TLC:R_f |
|---|---|---|---|---|
| 2.104 | trans-I-12 | 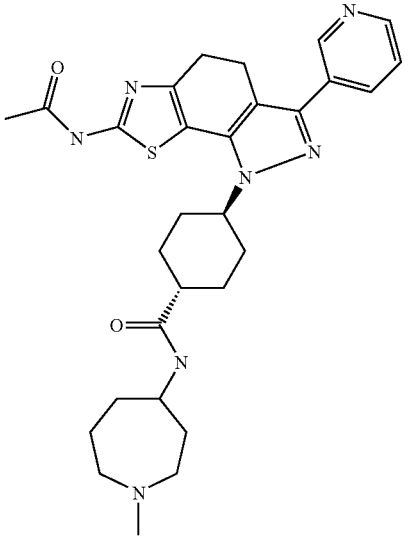 | 548 | 1.43 |
| 2.105 | trans-I-12 | 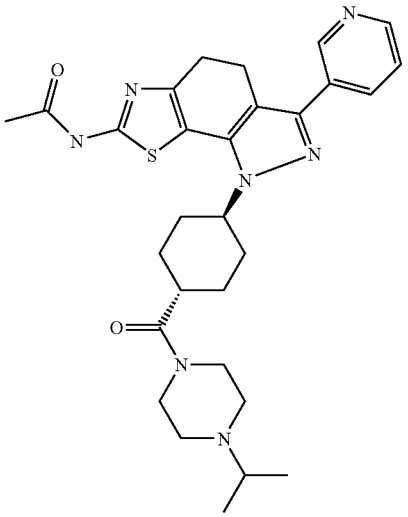 | 548 | 1.46 |
| 2.106 | trans-I-12 | 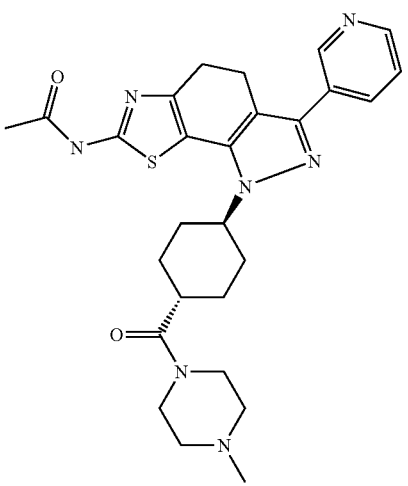 | 520 | 1.37 |

-continued

| # | Starting compound | Structure | Mass [M + 1]⁺ | HPLC Rt [min] or m.p. or TLC:R_f |
|---|---|---|---|---|
| 2.107 | trans-I-12 | 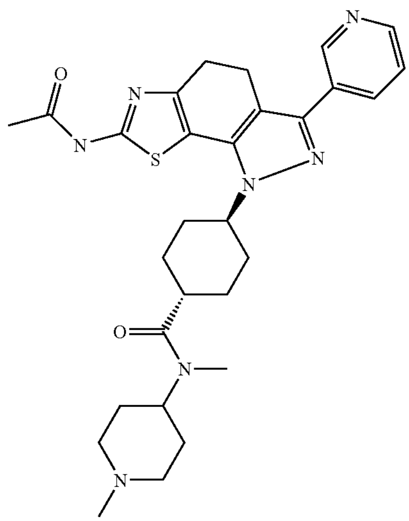 | 548 | 1.45 |
| 2.108 | trans-I-12 | 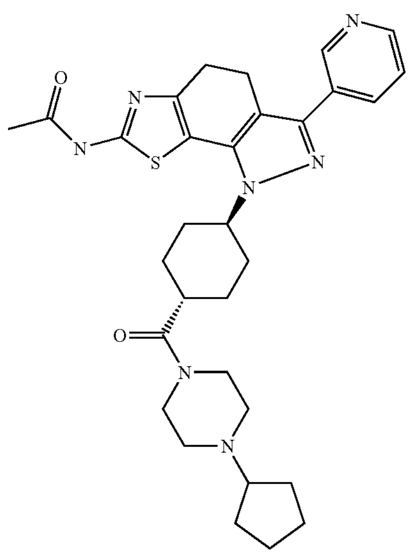 | 574 | 1.54 |
| 2.109 | I-23 | 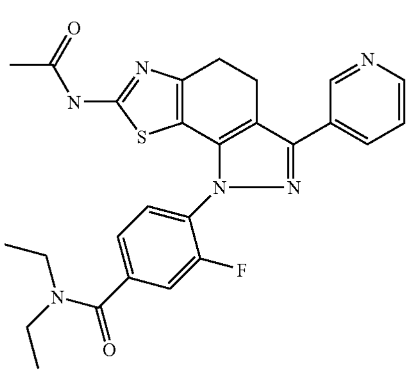 | 505 | 1.6 |

-continued

| # | Starting compound | Structure | Mass [M + 1]+ | HPLC Rt [min] or m.p. or TLC:R_f |
|---|---|---|---|---|
| 2.110 | I-23 | 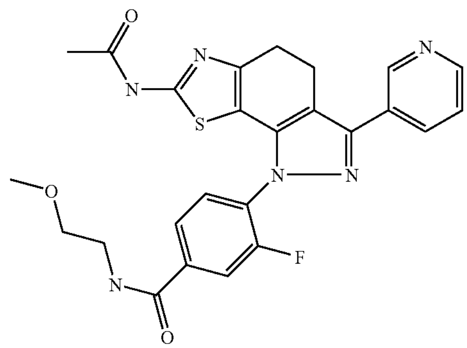 | 507 | 1.41 |
| 2.111 | I-23 | 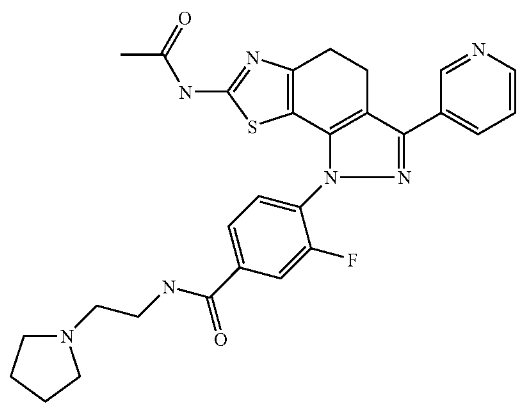 | 546 | 1.52 |
| 2.112 | I-23 | 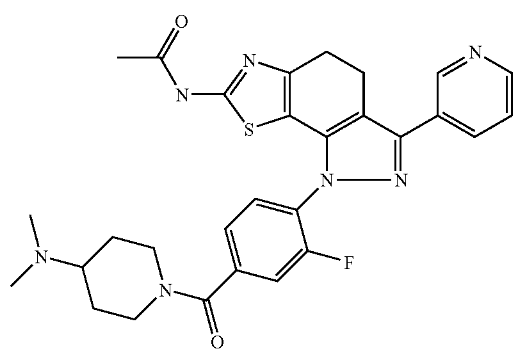 | 560 | 1.24 |
| 2.113 | I-23 | 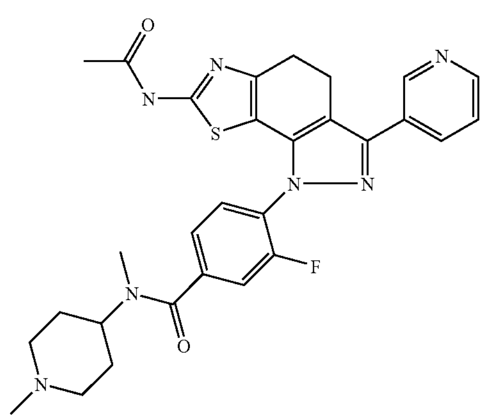 | 560 | 1.48 |

-continued

| # | Starting compound | Structure | Mass [M + 1]⁺ | HPLC Rt [min] or m.p. or TLC:R_f |
|---|---|---|---|---|
| 2.115 | I-23 | 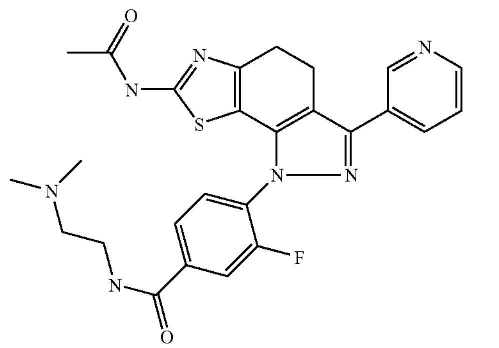 | 520 | 1.45 |
| 2.116 | I-23 | 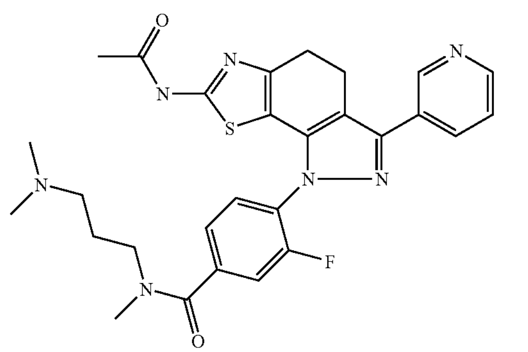 | 548 | 1.49 |
| 2.117 | I-23 | 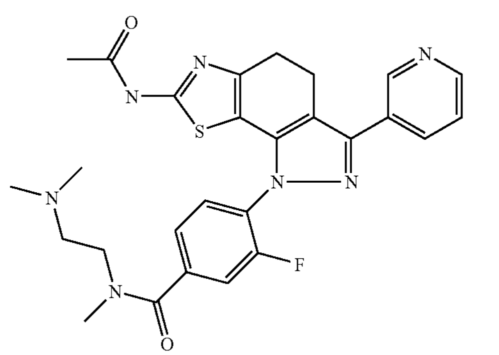 | 534 | 1.48 |
| 2.118 | I-23 | 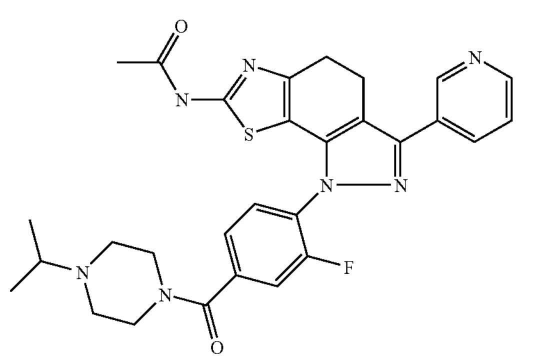 | 560 | 1.53 |

-continued

| # | Starting compound | Structure | Mass [M + 1]⁺ | HPLC Rt [min] or m.p. or TLC:R_f |
|---|---|---|---|---|
| 2.119 | I-23 | 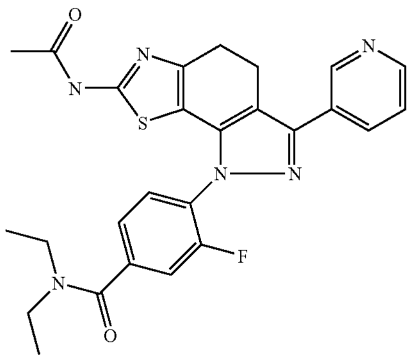 | 505 | 1.6 |
| 2.120 | I-23 | 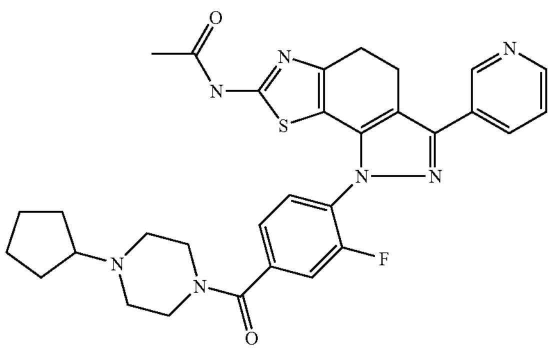 | 586 | 1.61 |
| 2.121 | I-23 | 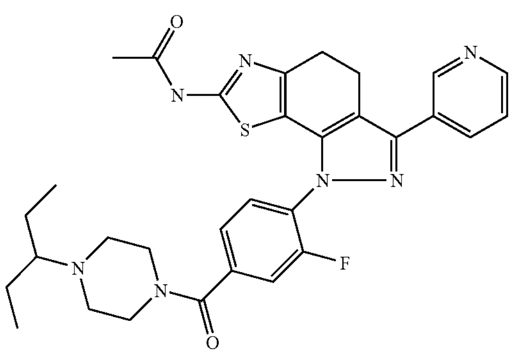 | 588 | 1.64 |
| 2.122 | I-23 | 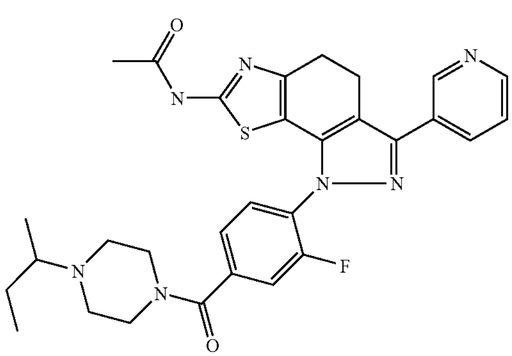 | 574 | 1.27 |

-continued
| # | Starting compound | Structure | Mass [M + 1]+ | HPLC Rt [min] or m.p. or TLC:R_f |
|---|---|---|---|---|
| 2.123 | I-23 | 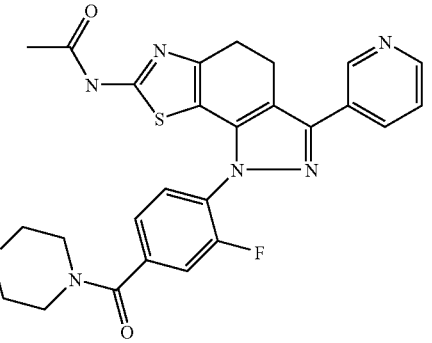 | 603 | 1.49 |
| 2.124 | I-23 | 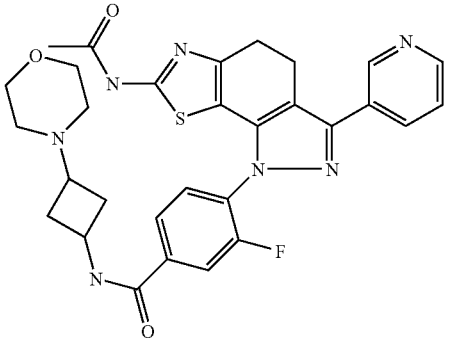 | 588 | 1.28 |
| 2.125 | I-23 | 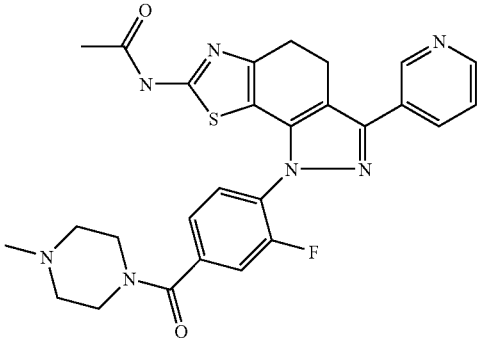 | 532 | 1.65 |
| 2.126 | I-25 | 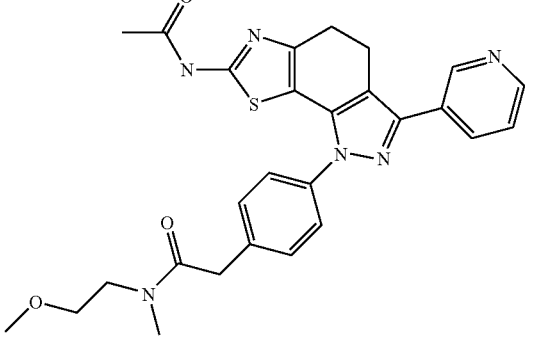 | 517 | R_f = 0.44 DCM: MEOH 9:1 |

|   | Starting | | Mass | HPLC Rt [min] |
|---|---|---|---|---|
| # | compound | Structure | [M + 1]⁺ | or m.p. or TLC:$R_f$ |
| 2.127 | I-25 | | 568 | $R_f$ = 0.18 DCM: MEOH 7:3 |
| 2.128 | I-25 | | 582 | $R_f$ = 0.24 DCM: MEOH 7:3 |
| 2.129 | I-25 | | 598 | 1.23 |

-continued

| # | Starting compound | Structure | Mass [M + 1]⁺ | HPLC Rt [min] or m.p. or TLC:R_f |
|---|---|---|---|---|
| 2.130 | I-25 | 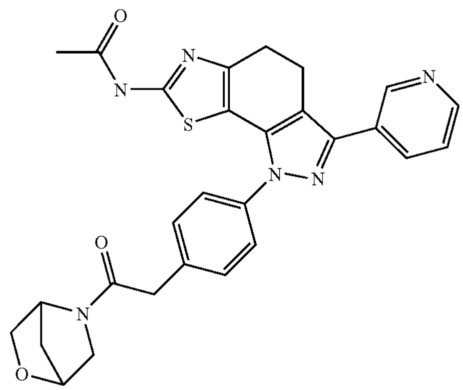 | 527 | 1.39 |
| 2.131 | I-25 | 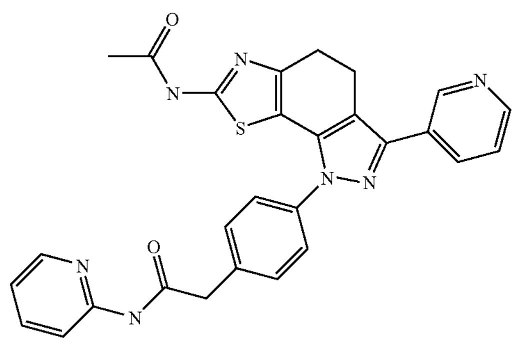 | 522 | 1.43 |
| 2.132 | I-25 | 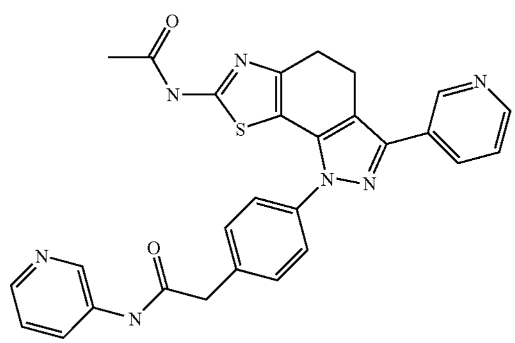 | 522 | R_f = 0.91 DCM: MEOH 9:1 |
| 2.133 | I-25 | 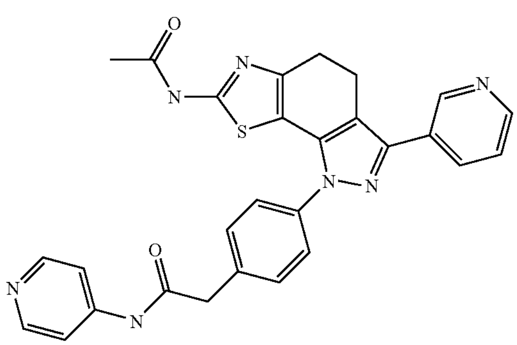 | 522 | R_f = 0.88 DCM: MEOH 9:1 |

-continued
| # | Starting compound | Structure | Mass [M + 1]+ | HPLC Rt [min] or m.p. or TLC:Rf |
|---|---|---|---|---|
| 2.134 | I-25 | 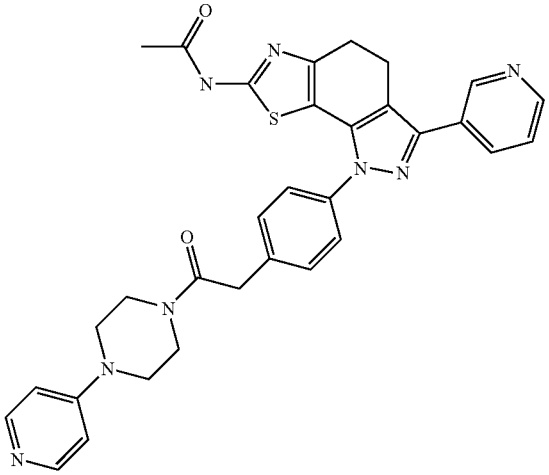 | 591 | Rf = 0.42 DCM: MEOH 9:1 |
| 2.135 | I-25 | 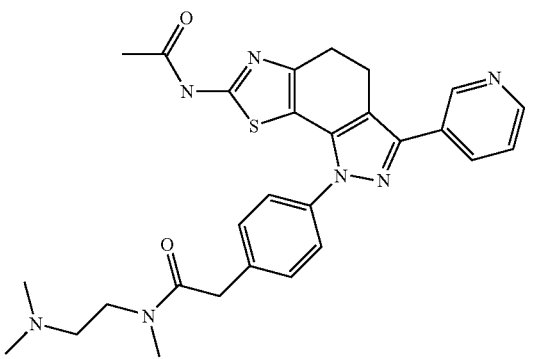 | 530 | Rf = 0.4 DCM: MEOH 9:1 |
| 2.136 | I-25 | 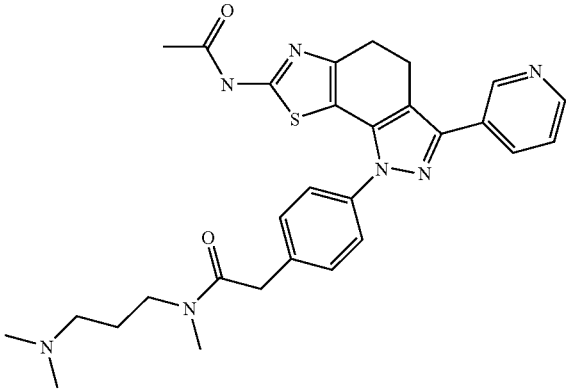 | 544 | Rf = 0.25 DCM: MEOH 9:1 |

-continued

| # | Starting compound | Structure | Mass [M + 1]⁺ | HPLC Rt [min] or m.p. or TLC:R_f |
|---|---|---|---|---|
| 2.137 | I-25 | 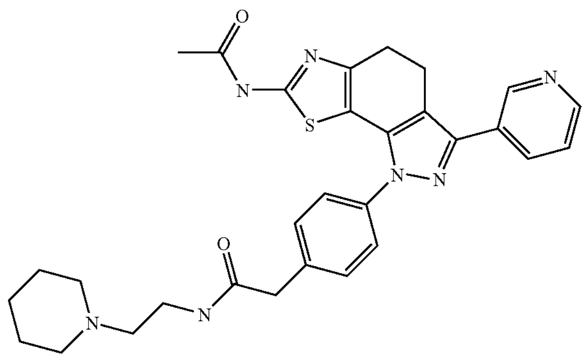 | 556 | 1.27 |
| 2.138 | I-25 | 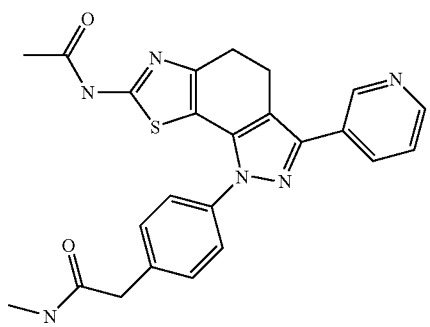 | 459 | R_f = 0.34 DCM: MEOH 9:1 |
| 2.139 | I-25 | 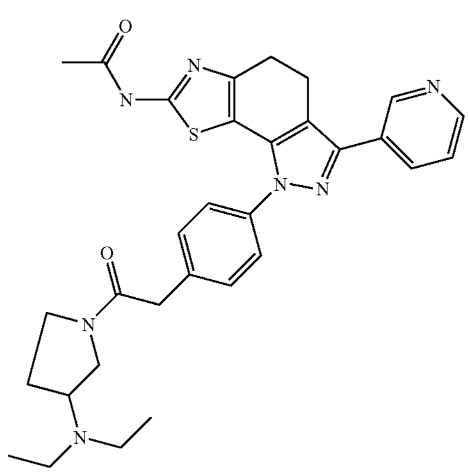 | 570 | R_f = 0.18 DCM: MEOH 8:2 |

-continued

| # | Starting compound | Structure | Mass [M + 1]⁺ | HPLC Rt [min] or m.p. or TLC:R_f |
|---|---|---|---|---|
| 2.140 | I-25 | 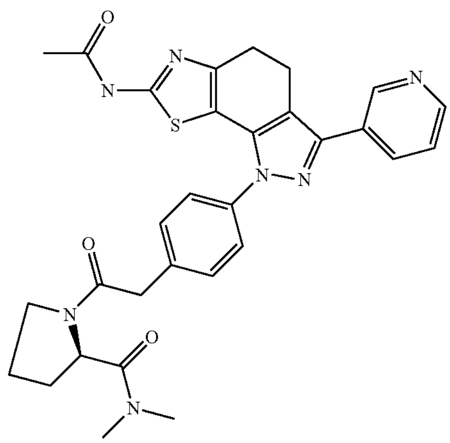 | 570 | 1.43 |
| 2.141 | I-20 | 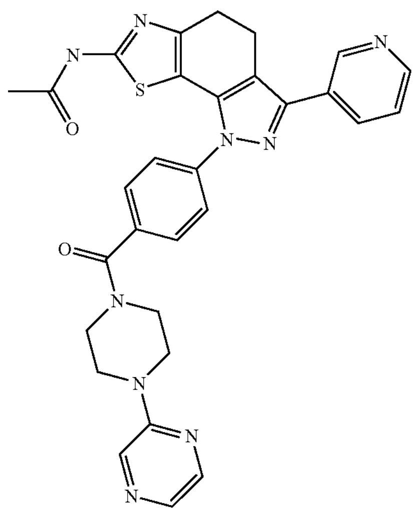 | 578 | 1.56 |
| 2.142 | I-20 | 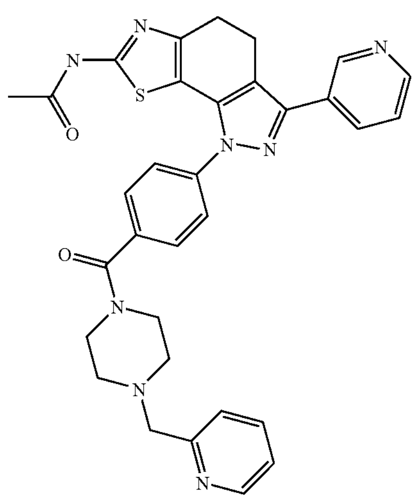 | 591 | 1.53 |

-continued

| # | Starting compound | Structure | Mass [M + 1]+ | HPLC Rt [min] or m.p. or TLC:R$_f$ |
|---|---|---|---|---|
| 2.143 | I-20 | 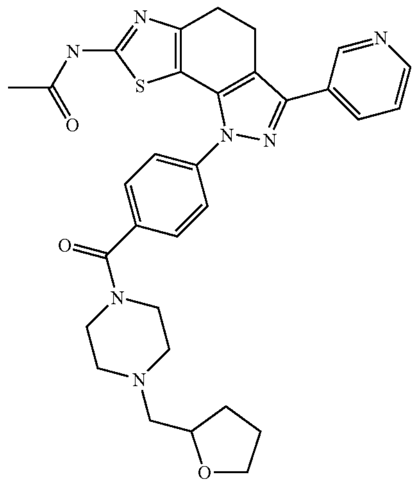 | 584 | 1.53 |
| 2.144 | I-20 | 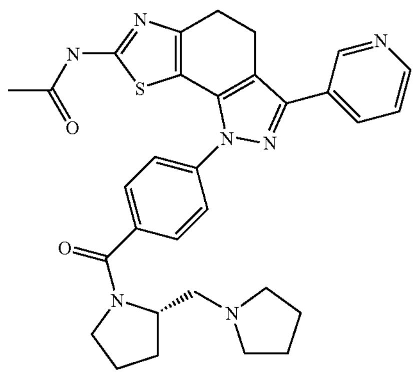 | 568 | 1.61 |
| 2.145 | I-20 | 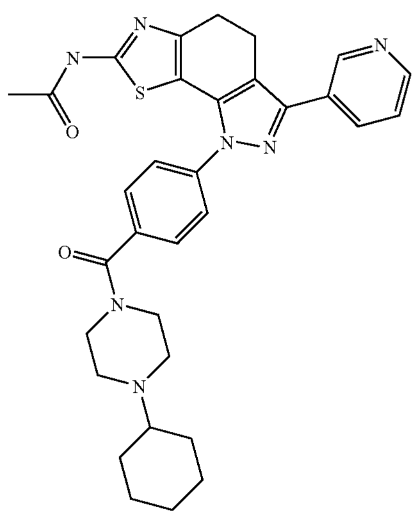 | 582 | 1.64 |

-continued

| # | Starting compound | Structure | Mass [M + 1]⁺ | HPLC Rt [min] or m.p. or TLC:R_f |
|---|---|---|---|---|
| 2.146 | I-20 | 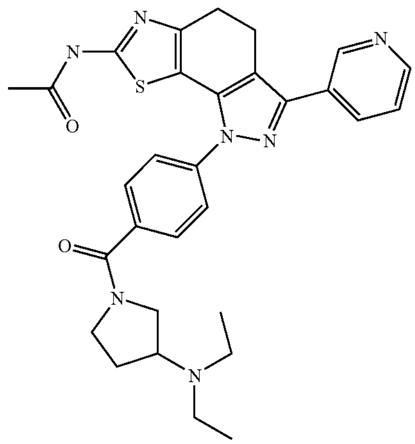 | 556 | 1.50 |
| 2.147 | I-20 | 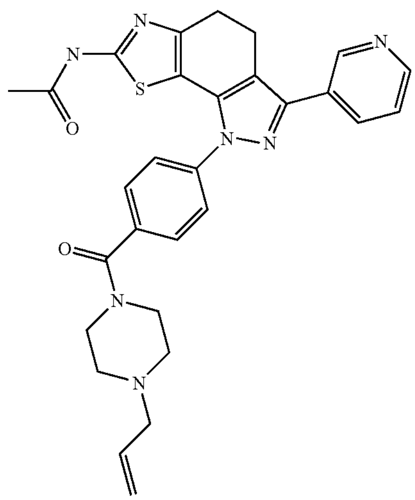 | 540 | 1.48 |
| 2.148 | I-20 | 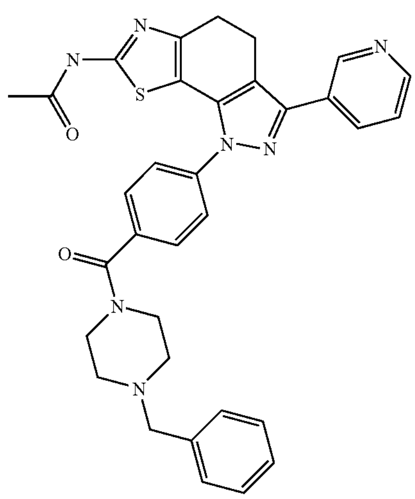 | 590 | 1.65 |

-continued

| # | Starting compound | Structure | Mass [M + 1]+ | HPLC Rt [min] or m.p. or TLC:R_f |
|---|---|---|---|---|
| 2.149 | I-20 | 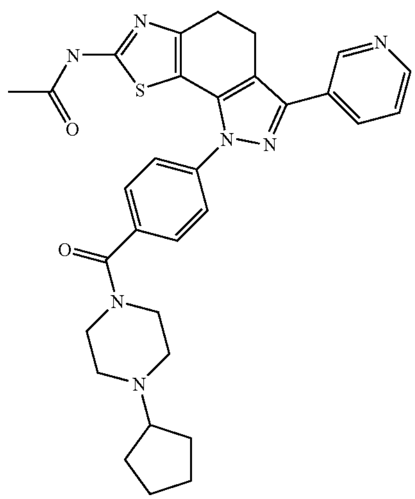 | 568 | 1.58 |
| 2.150 | I-20 | 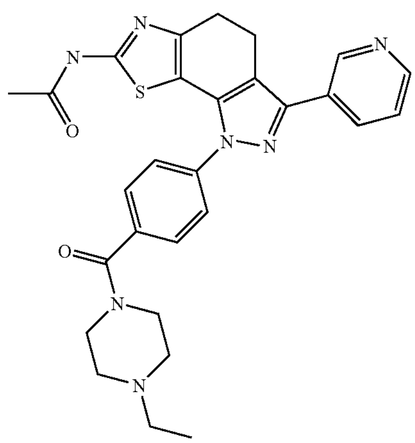 | 528 | 1.44 |
| 2.151 | I-20 | 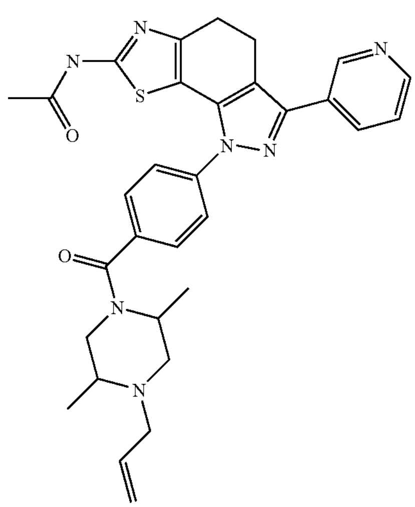 | 568 | 1.54 |

| # | Starting compound | Structure | Mass [M + 1]+ | HPLC Rt [min] or m.p. or TLC:Rf |
|---|---|---|---|---|
| 2.152 | I-20 | 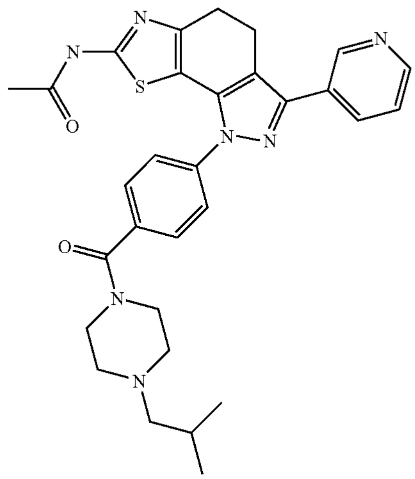 | 556 | 1.29 |
| 2.153 | I-20 | 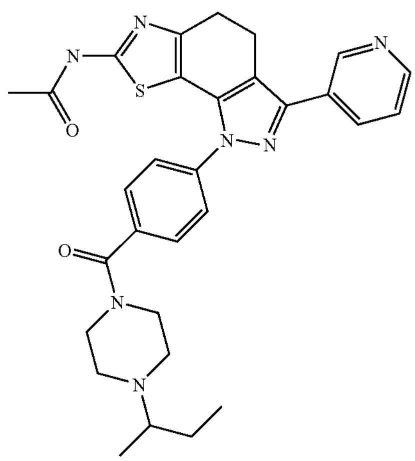 | 556 | 1.55 |
| 2.154 | I-21 | 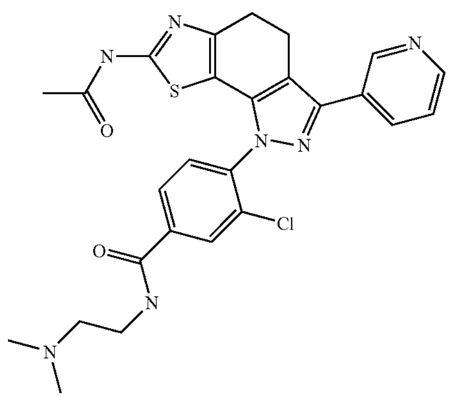 | 536 | 1.48 |

-continued
| # | Starting compound | Structure | Mass [M + 1]+ | HPLC Rt [min] or m.p. or TLC:R_f |
|---|---|---|---|---|
| 2.155 | I-21 | 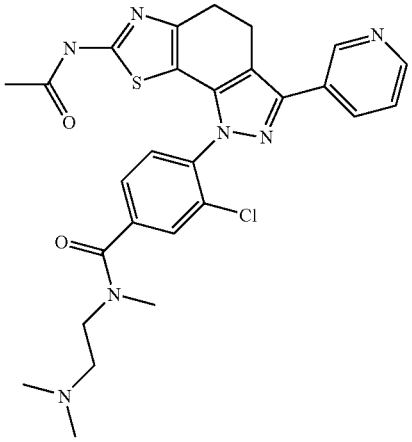 | 550 | 1.49 |
| 2.156 | I-21 | 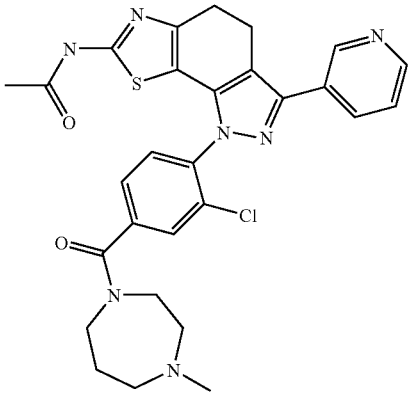 | 562 | 1.49 |
| 2.157 | I-21 | 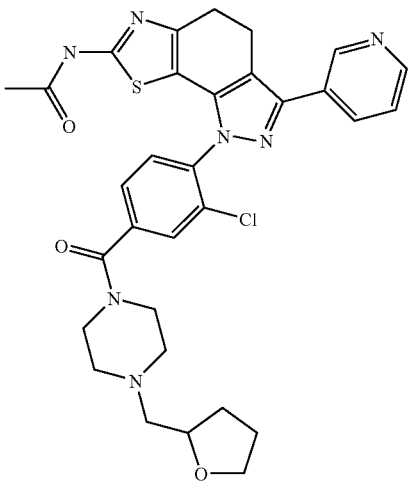 | 618 | 1.58 |

-continued

| # | Starting compound | Structure | Mass [M + 1]+ | HPLC Rt [min] or m.p. or TLC:R_f |
|---|---|---|---|---|
| 2.158 | I-21 | 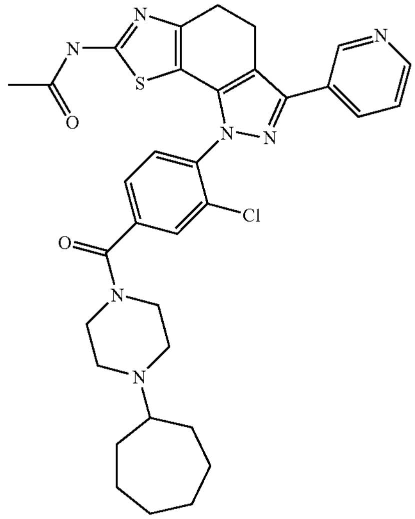 | 630 | 1.50 |
| 2.159 | I-21 | 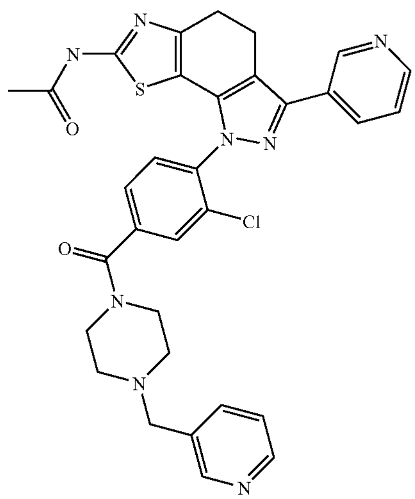 | 625 | 1.55 |
| 2.160 | I-21 | 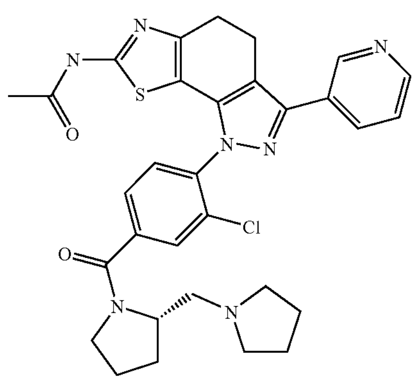 | 602 | 1.65 |

-continued

| # | Starting compound | Structure | Mass [M + 1]+ | HPLC Rt [min] or m.p. or TLC:Rf |
|---|---|---|---|---|
| 2.161 | I-21 | 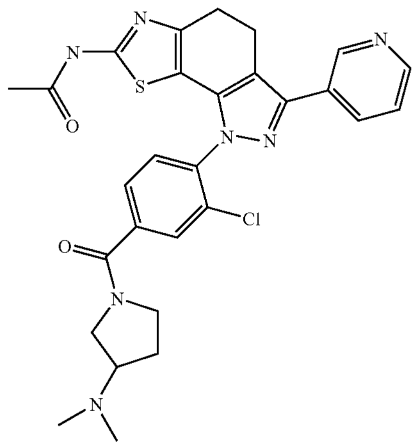 | 562 | 1.47 |
| 2.162 | I-21 | 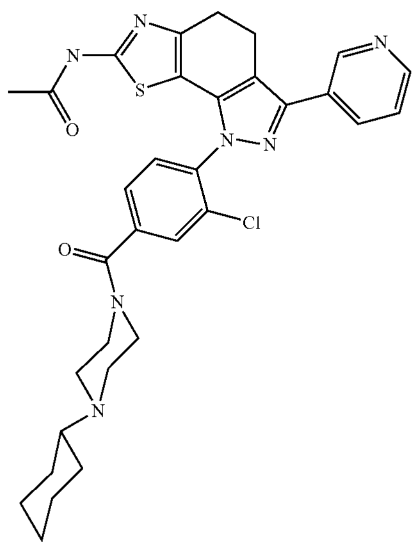 | 616 | 1.72 |
| 2.163 | I-21 | 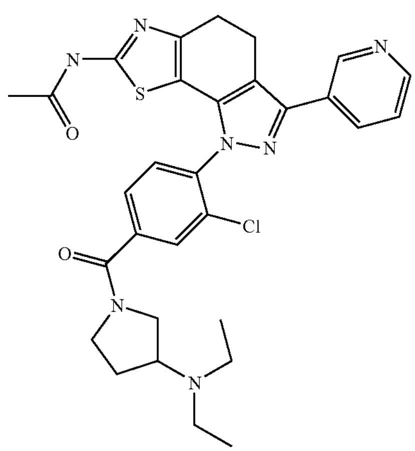 | 590 | 1.25 |

-continued

| # | Starting compound | Structure | Mass [M + 1]⁺ | HPLC Rt [min] or m.p. or TLC:R_f |
|---|---|---|---|---|
| 2.164 | I-21 | 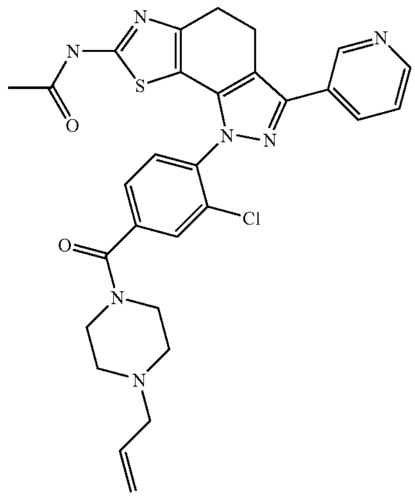 | 574 | 1.55 |
| 2.165 | I-21 | 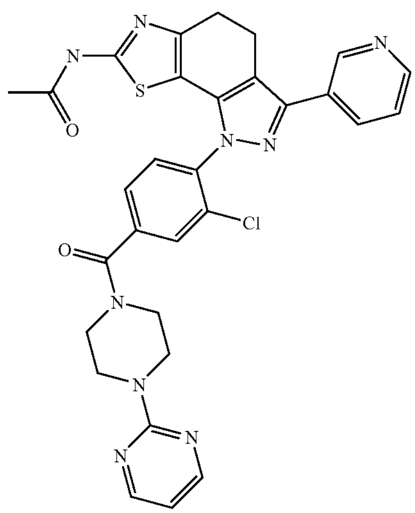 | 612 | 1.64 |
| 2.166 | I-21 | 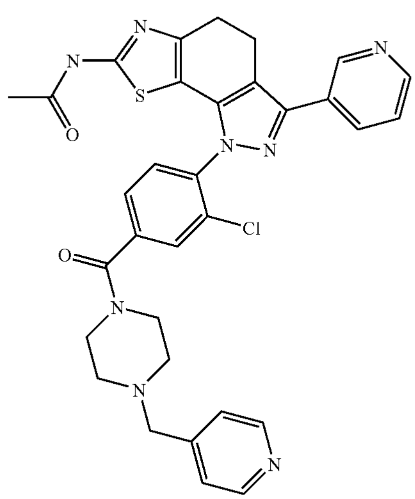 | 625 | 1.58 |

-continued

| # | Starting compound | Structure | Mass [M + 1]+ | HPLC Rt [min] or m.p. or TLC:R_f |
|---|---|---|---|---|
| 2.167 | I-21 | 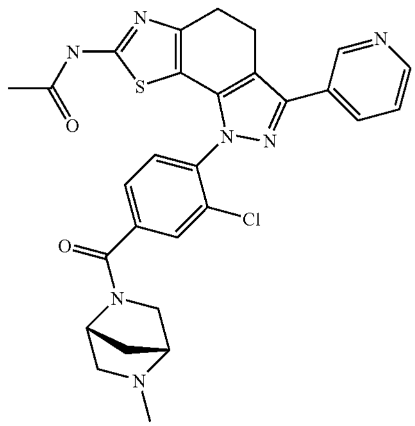 | 560 | 1.46 |
| 2.168 | I-21 | 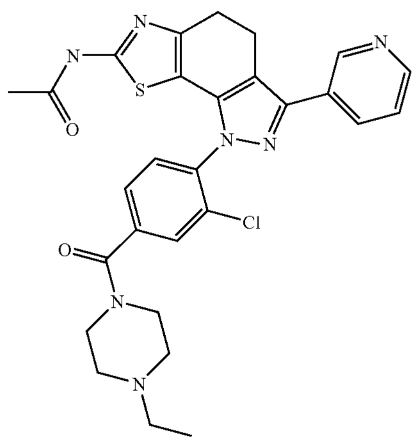 | 562 | 1.77 |
| 2.169 | I-21 | 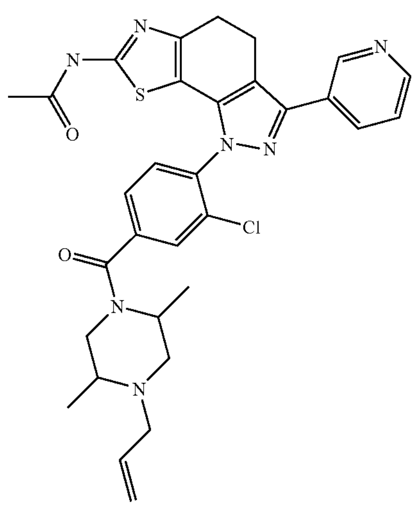 | 602 | 1.62 |

-continued

| # | Starting compound | Structure | Mass [M + 1]+ | HPLC Rt [min] or m.p. or TLC:R_f |
|---|---|---|---|---|
| 2.170 | I-21 | 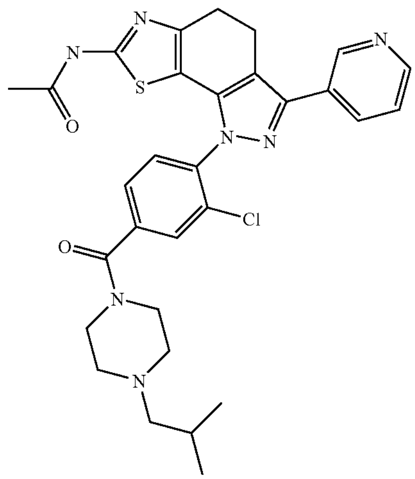 | 590 | 1.62 |
| 2.171 | I-21 | 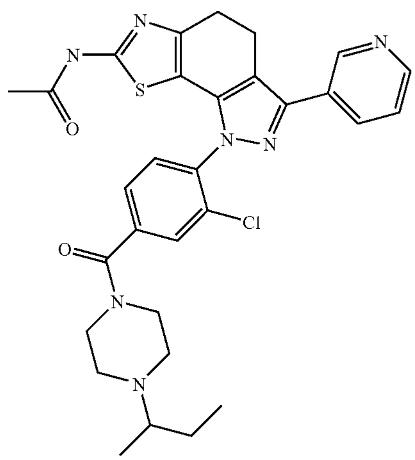 | 590 | 1.61 |
| 2.172 | I-21 | 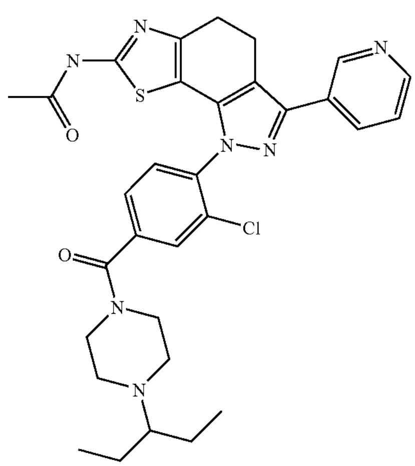 | 604 | 1.68 |

-continued

| # | Starting compound | Structure | Mass [M + 1]⁺ | HPLC Rt [min] or m.p. or TLC:R_f |
|---|---|---|---|---|
| 2.173 | I-21 | 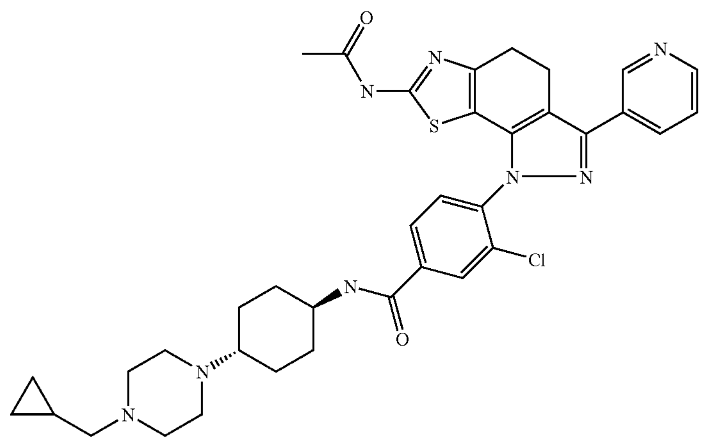 | 685 | 2.59 |
| 2.174 | I-20 | 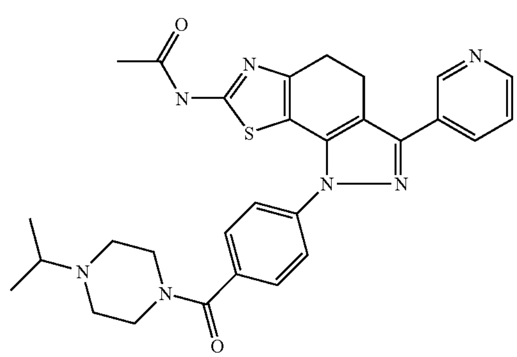 | 542 | 2.56 |
| 2.176 | I-41 | 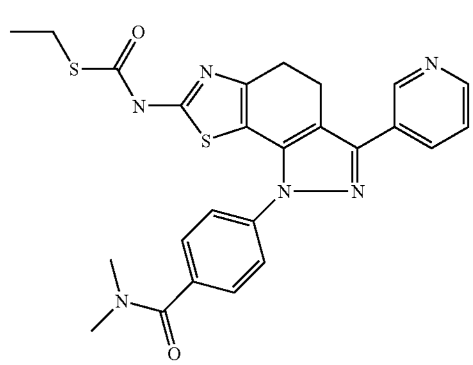 | 505 | |

-continued

| # | Starting compound | Structure | Mass [M + 1]⁺ | HPLC Rt [min] or m.p. or TLC:R_f |
|---|---|---|---|---|
| 2.177 | I-42 | 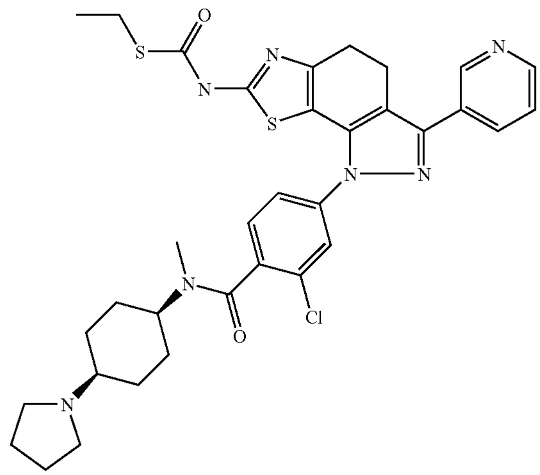 | 676 | |
| 2.178 | I-42 | 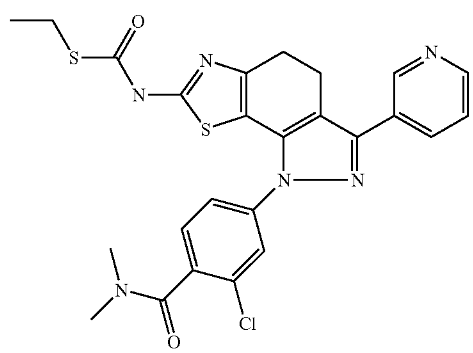 | 539 | |
| 2.179 | I-12 | 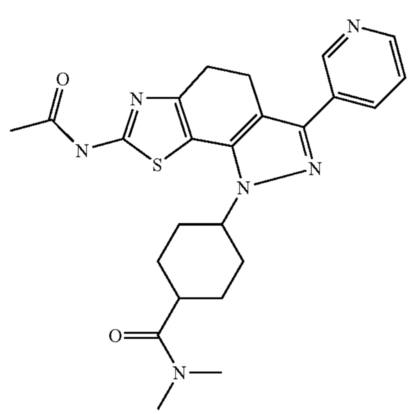 | 465 | 1.46 |

-continued

| # | Starting compound | Structure | Mass [M + 1]+ | HPLC Rt [min] or m.p. or TLC:R_f |
|---|---|---|---|---|
| 2.180 | I-21 | 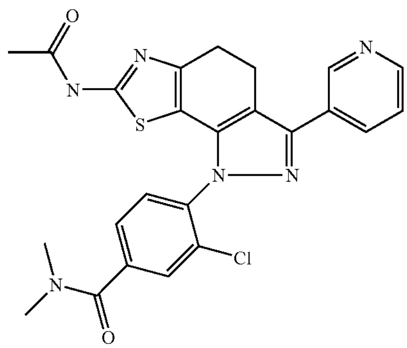 | 493 | 1.56 |
| 2.181 | I-20 | 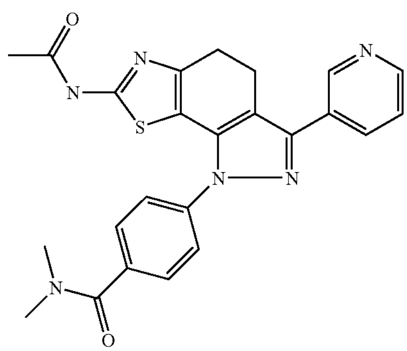 | 459 | 1.5 |
| 2.182 | I-23 | 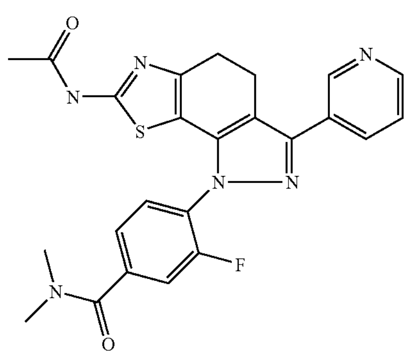 | 477 | 2.87 |
| 2.183 | II-19 | 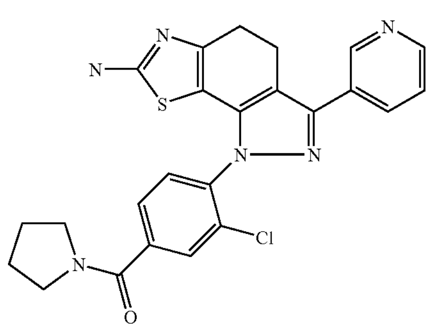 | 477 | 1.44 |

*In Example 2.18, the carboxylic acid is reacted with tert-butyl (2-aminocyclopropyl)carbamate. In the 2nd step, the BOC protecting group is eliminated with trifluoroacetic acid.

Examples 3

Reacting the Amines which have been Prepared

Synthesis Method E—Reacting with Sulphonyl Chlorides 0.5 mmol of sulphonyl chloride is added to a solution of 0.2 mmol of amine in 3 ml of pyridine and the mixture is stirred at RT for 15 h. The reaction mixture is evaporated and the residue is purified chromatographically.

Synthesis Method F—Reacting with Carboxylic Acids

HATU (0.55 mmol) and diisopropylethylamine (1.8 mmol) are added to a solution of the carboxylic acid (0.16 mmol) in 1.3 ml of DMF and the mixture is stirred at RT for 1 h. After a solution of 0.1 mmol of the appropriate amine in DMF has been added, the mixture is stirred at RT for a further 15 h. The reaction mixture is then filtered and evaporated and the residue is purified chromatographically.

Synthesis Method G—Reacting with Carbonyl Chlorides 0.5 mmol of carbonyl chloride is added to a solution of 0.2 mmol of amine in 3 ml of pyridine and the mixture is stirred at RT for 15. The reaction mixture is evaporated and the residue is purified chromatographically.

Examples 3.2-3.82

| # | Starting compound | Structure | Mass [M + 1]$^+$ | HPLC Rt [min] or m.p. or TLC:R$_f$ |
|---|---|---|---|---|
| 3.2 | II-1 | 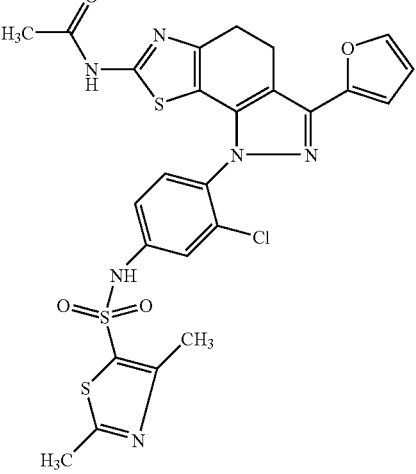 | 601 | 2.08 |
| 3.3 | II-3 | 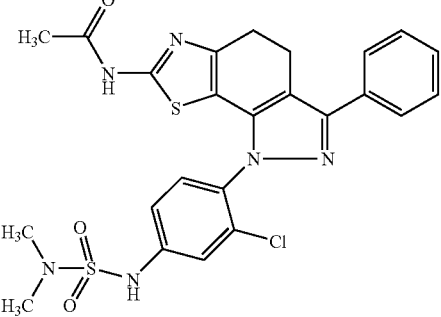 | 543 | 2.2 |

-continued

| # | Starting compound | Structure | Mass [M + 1]+ | HPLC Rt [min] or m.p. or TLC:R$_f$ |
|---|---|---|---|---|
| 3.4 | II-1 | 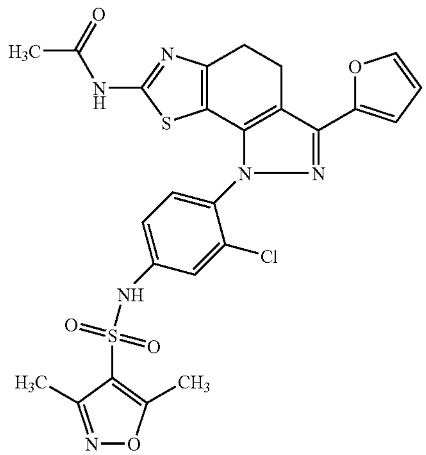 | 585 | 2.12 |
| 3.10 | II-4 | 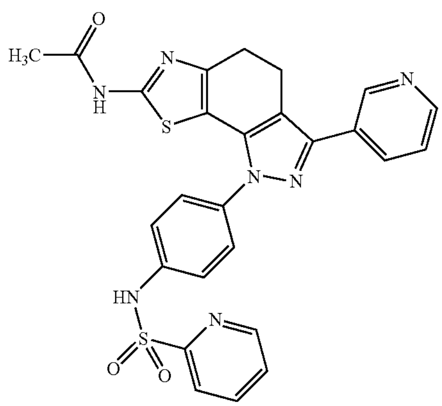 | 544 | 1.62 |
| 3.11 | II-4 | 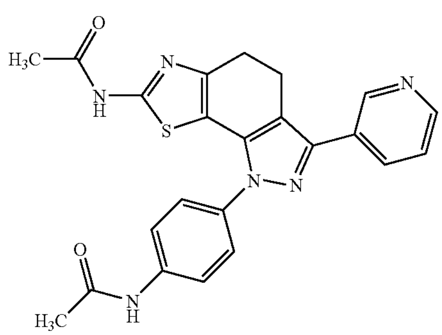 | 445 | 1.45 |
| 3.12 | II-4 | 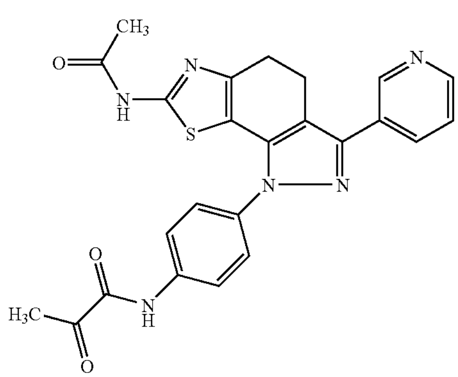 | 473 | 1.6 |

-continued
| # | Starting compound | Structure | Mass [M + 1]+ | HPLC Rt [min] or m.p. or TLC:R_f |
|---|---|---|---|---|
| 3.13 | II-4 | 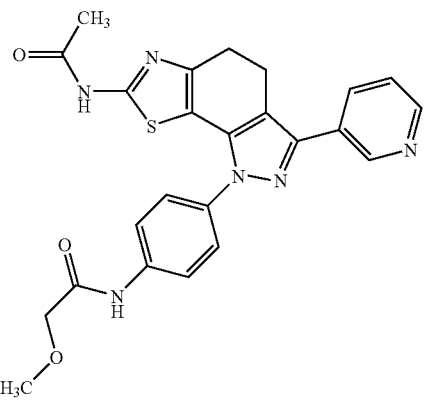 | 475 | 1.48 |
| 3.14 | II-4 | 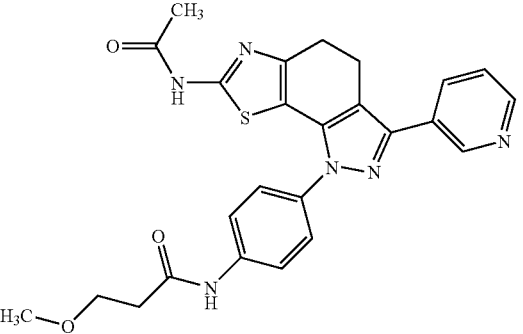 | 489 | 1.5 |
| 3.15 | II-4 | 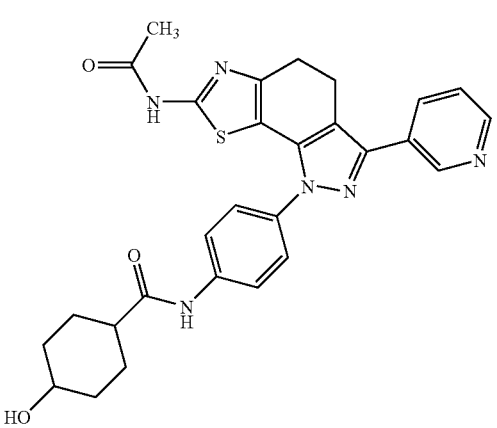 | 529 | 1.53 |

-continued
| # | Starting compound | Structure | Mass [M + 1]+ | HPLC Rt [min] or m.p. or TLC:R_f |
|---|---|---|---|---|
| 3.16 | II-4 | 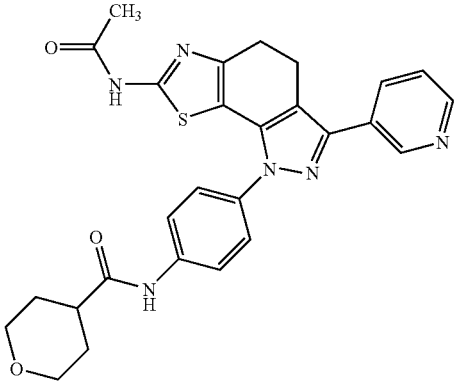 | 515 | 1.52 |
| 3.17 | II-4 | 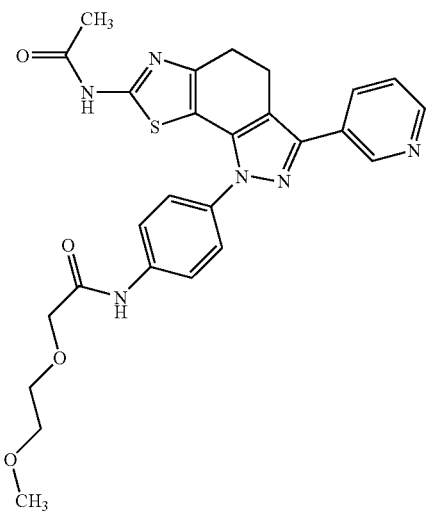 | 519 | 1.58 |
| 3.18 | II-4 | 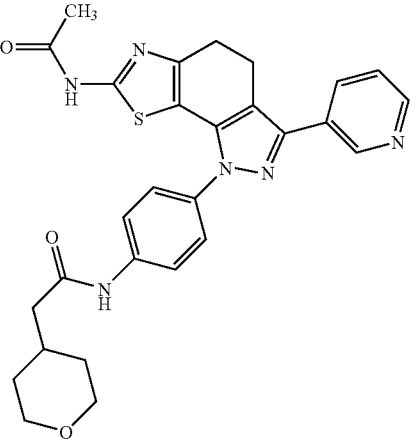 | 529 | 1.59 |

-continued

| # | Starting compound | Structure | Mass [M + 1]+ | HPLC Rt [min] or m.p. or TLC:Rf |
|---|---|---|---|---|
| 3.19 | II-4 | 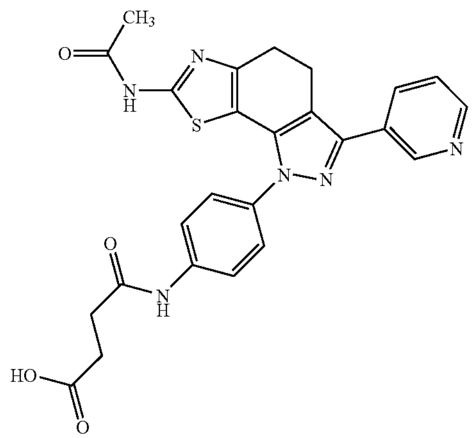 | 503 | 1.43 |
| 3.20 | II-4 | 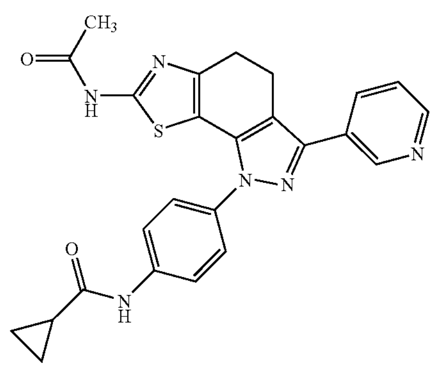 | 471 | 1.6 |
| 3.21 | II-4 | 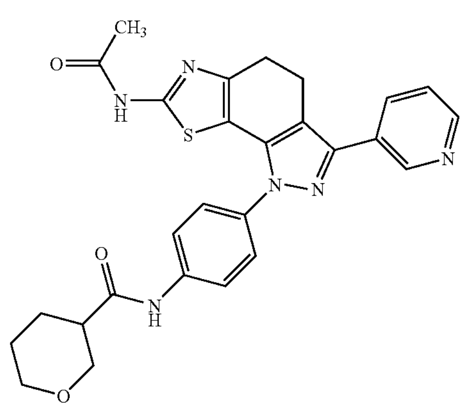 | 515 | 1.57 |

-continued
| # | Starting compound | Structure | Mass [M + 1]⁺ | HPLC Rt [min] or m.p. or TLC:$R_f$ |
|---|---|---|---|---|
| 3.22 | II-4 | 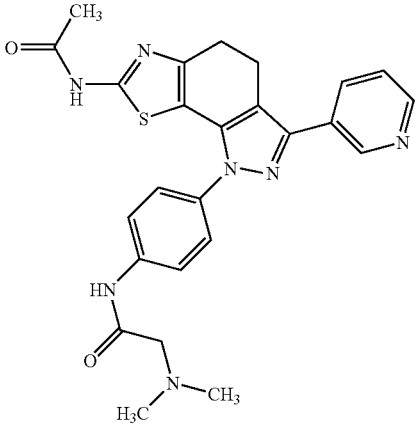 | 488 | 0.47 |
| 3.23 | II-5 | 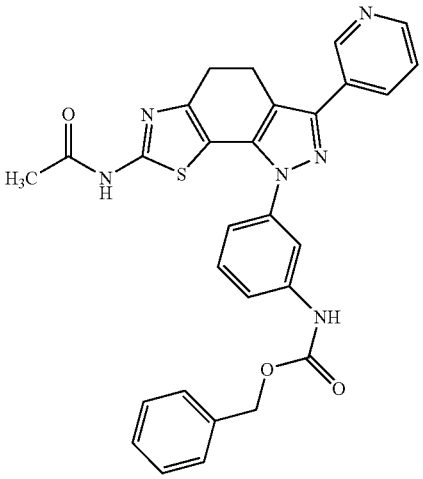 | 537 | 1.89 |
| 3.24 | II-5 | 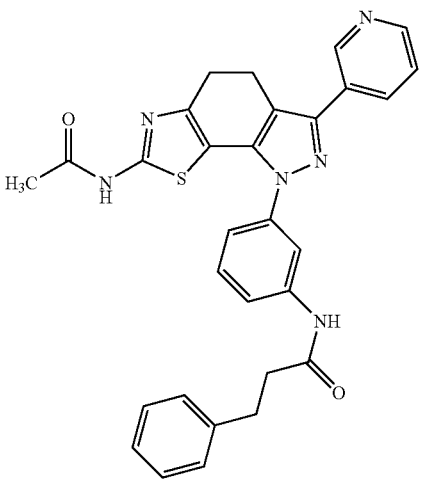 | 535 | 1.81 |

-continued

| # | Starting compound | Structure | Mass [M + 1]+ | HPLC Rt [min] or m.p. or TLC:R$_f$ |
|---|---|---|---|---|
| 3.25 | II-6 | 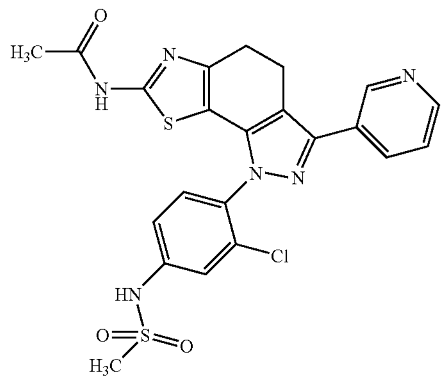 | 515 | 1.54 |
| 3.26 | II-6 | 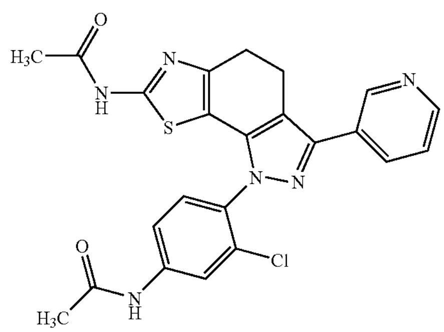 | 479 | 1.52 |
| 3.27 | II-6 | 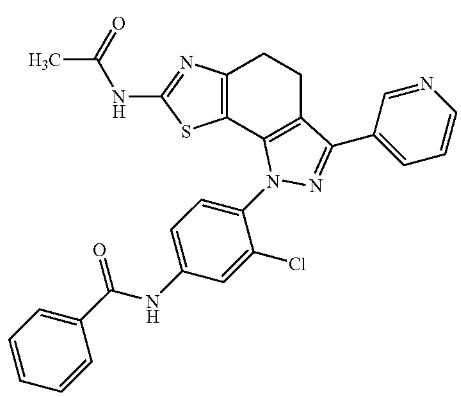 | 541 | 1.82 |
| 3.28 | II-6 | 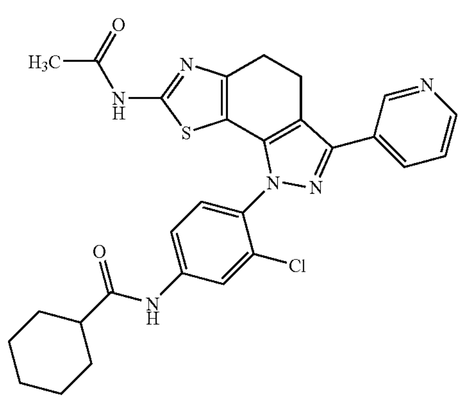 | 547 | 1.90 |

-continued

| # | Starting compound | Structure | Mass [M + 1]+ | HPLC Rt [min] or m.p. or TLC:R$_f$ |
|---|---|---|---|---|
| 3.29 | II-6 | 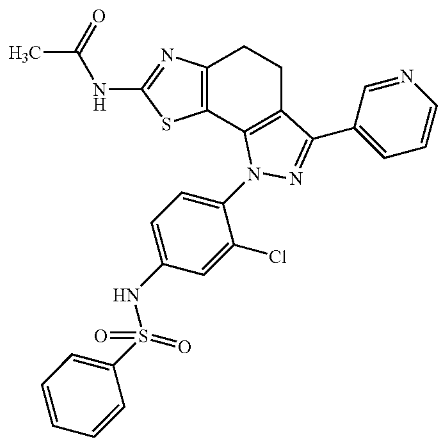 | 577 | 1.81 |
| 3.30 | II-6 | 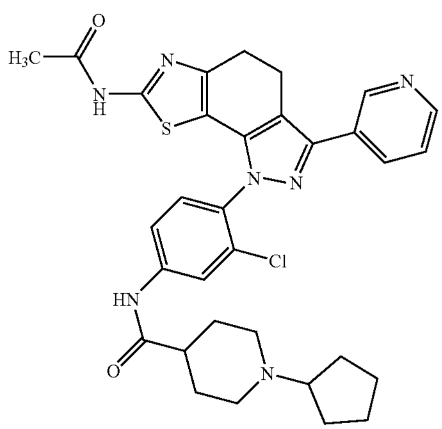 | 616 | 1.38 |
| 3.31 | II-6 | 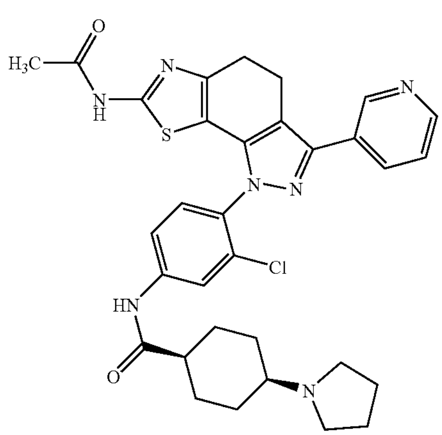 | 616 | Rf: 0.18 MeOH:NH$_4$OH 92.5:7.5:1 |

-continued

| # | Starting compound | Structure | Mass [M + 1]+ | HPLC Rt [min] or m.p. or TLC:R$_f$ |
|---|---|---|---|---|
| 3.32 | II-6 | 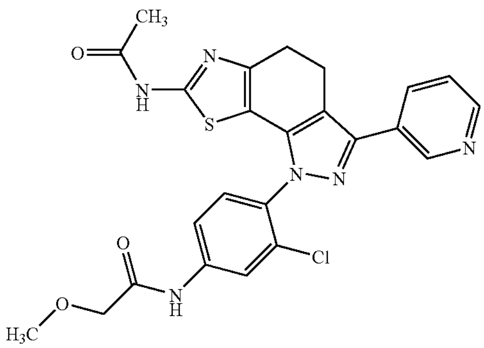 | 509 | 1.43 |
| 3.33 | II-6 | 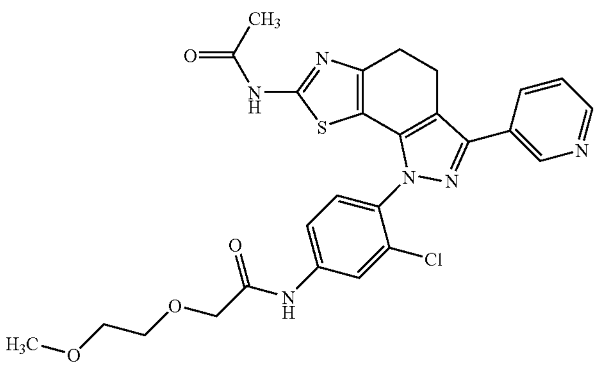 | 553 | 1.55 |
| 3.34 | II-12 | 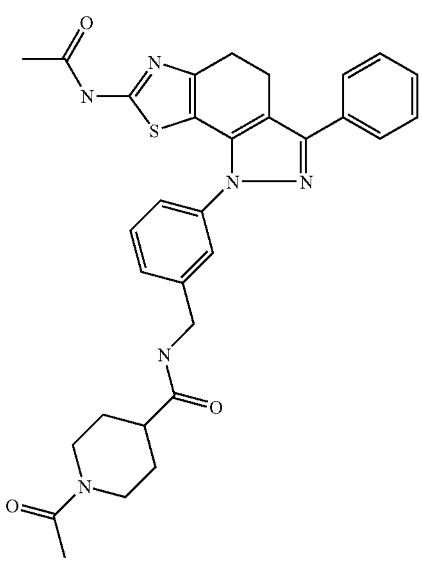 | 569 | m.p.: 277° C. |

-continued
| # | Starting compound | Structure | Mass [M + 1]+ | HPLC Rt [min] or m.p. or TLC:R$_f$ |
|---|---|---|---|---|
| 3.35 | II-12 | 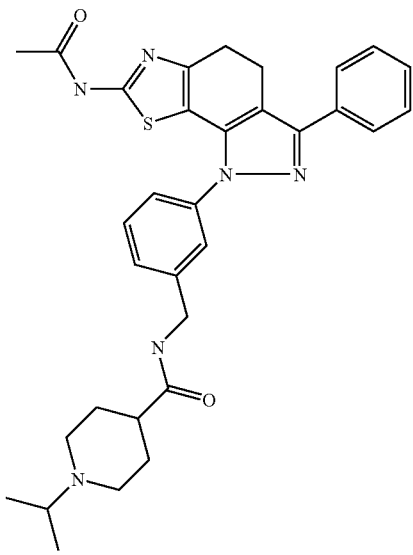 | 569 | 2.59 |
| 3.36 | II-12 | 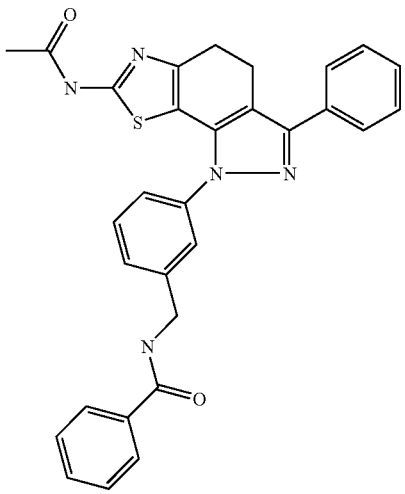 | 520 | m.p.: 282° C. |

-continued

| # | Starting compound | Structure | Mass [M + 1]+ | HPLC Rt [min] or m.p. or TLC:R_f |
|---|---|---|---|---|
| 3.37 | II-12 | 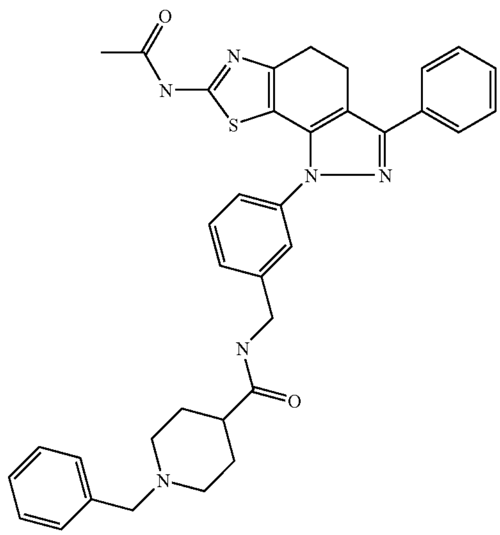 | 617 | m.p.: 227° C. |
| 3.38 | II-12 | 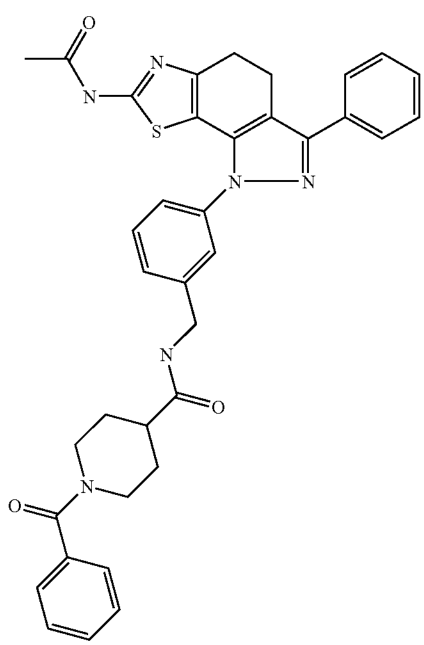 | 631 | m.p.: 294° C. |

-continued

| # | Starting compound | Structure | Mass [M + 1]+ | HPLC Rt [min] or m.p. or TLC:R$_f$ |
|---|---|---|---|---|
| 3.39 | II-12 | 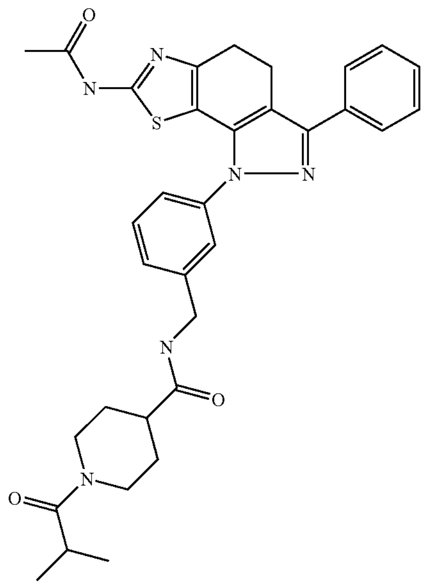 | 597 | 3.0 |
| 3.40 | II-12 | 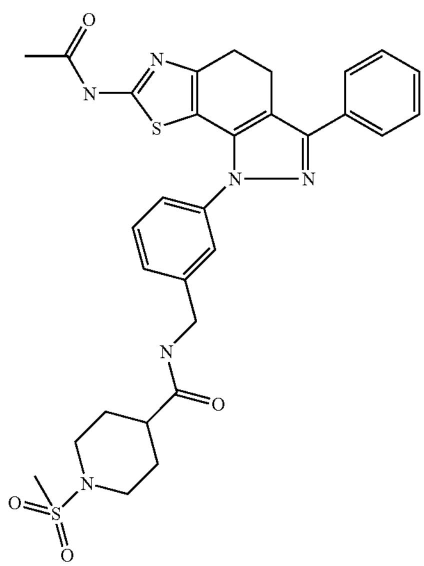 | 605 | 2.95 |
| 3.41 | I-11 | 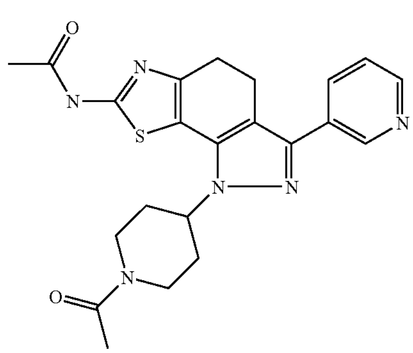 | 437 | 1.28 |

-continued

| # | Starting compound | Structure | Mass [M + 1]+ | HPLC Rt [min] or m.p. or TLC:Rf |
|---|---|---|---|---|
| 3.42 | I-11 | 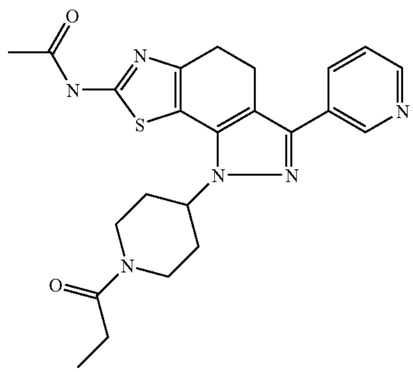 | 451 | 1.4 |
| 3.43 | I-11 | 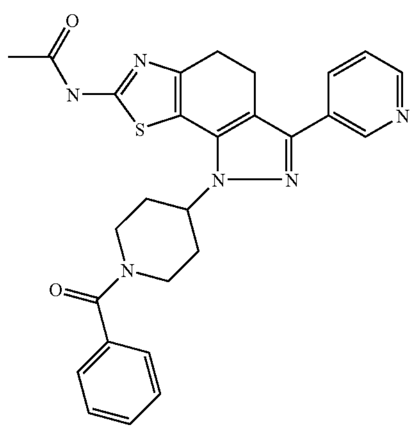 | 499 | 1.56 |
| 3.44 | I-11 | 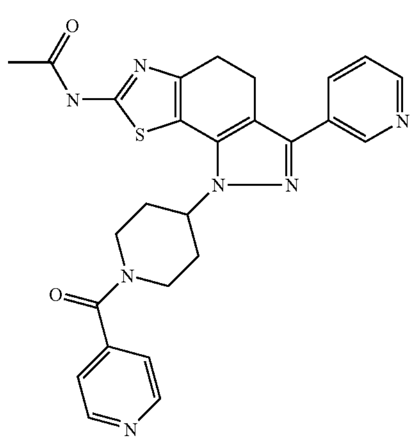 | 500 | 1.21 |

| # | Starting compound | Structure | Mass [M + 1]+ | HPLC Rt [min] or m.p. or TLC:R_f |
|---|---|---|---|---|
| 3.45 | I-11 | 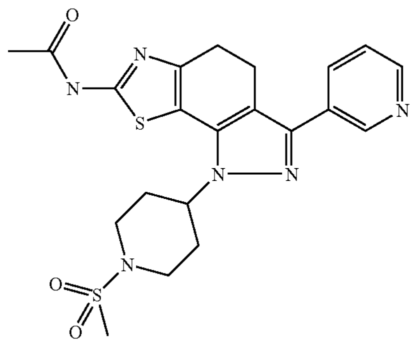 | 473 | 1.38 |
| 3.46 | I-11 | 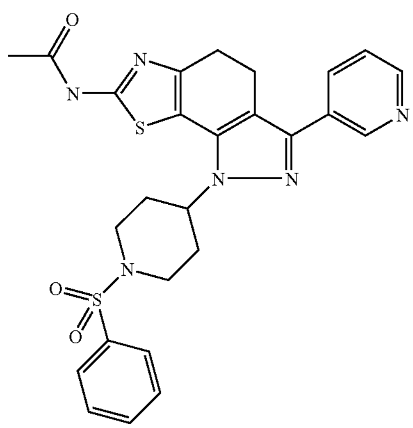 | 499 | 1.68 |
| 3.47 | I-11 | 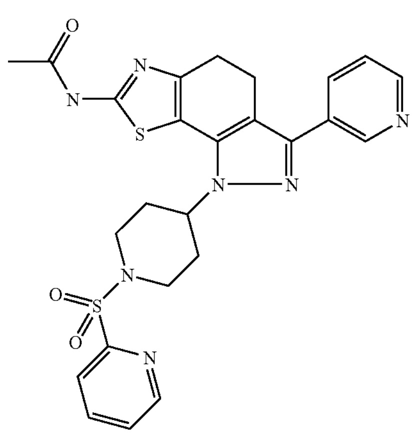 | 536 | 1.52 |

| # | Starting compound | Structure | Mass [M + 1]+ | HPLC Rt [min] or m.p. or TLC:R_f |
|---|---|---|---|---|
| 3.49 | I-40 | 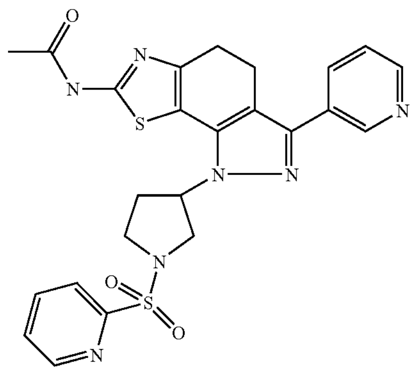 | 522 | 1.47 |
| 3.50 | I-11 | 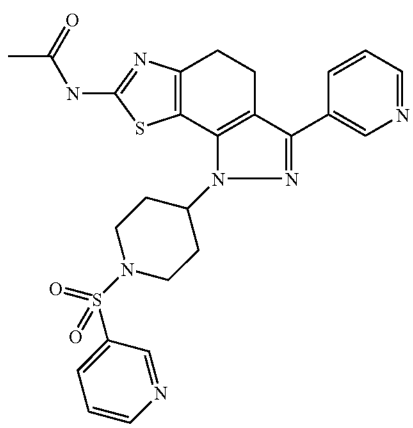 | 536 | 1.52 |
| 3.51 | I-11 | 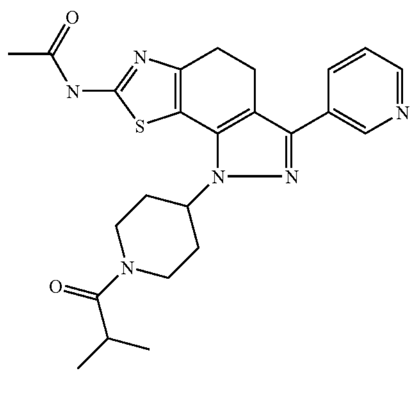 | 465 | 1.47 |

| # | Starting compound | Structure | Mass [M + 1]+ | HPLC Rt [min] or m.p. or TLC:R_f |
|---|---|---|---|---|
| 3.52 | I-11 | 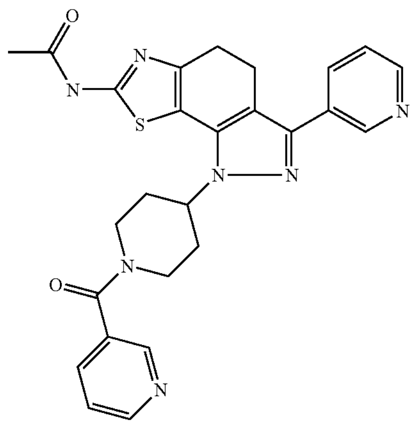 | 500 | 1.34 |
| 3.53 | I-11 | 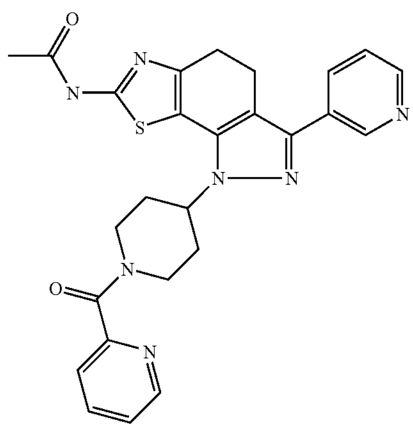 | 500 | 1.46 |
| 3.54 | II-13 | 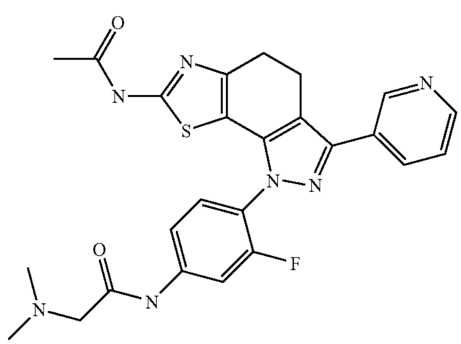 | 506 | 1.47 |
| 3.55 | II-13 | 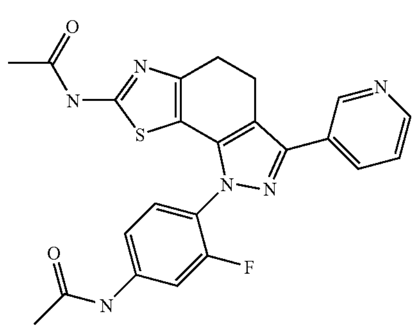 | 463 | 1.46 |

-continued

| # | Starting compound | Structure | Mass [M + 1]+ | HPLC Rt [min] or m.p. or TLC:R_f |
|---|---|---|---|---|
| 3.56 | II-4 | 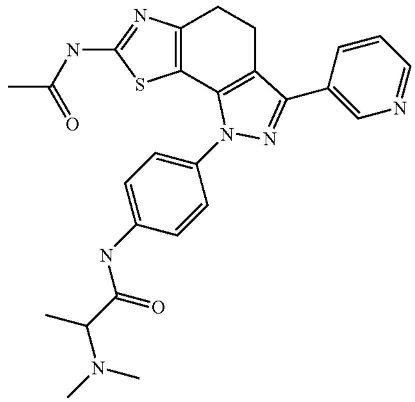 | 502 | 1.45 |
| 3.57 | II-4 | 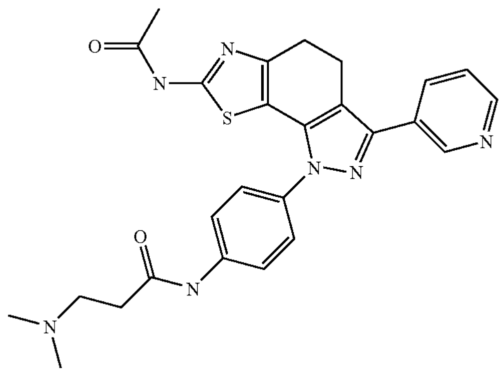 | 502 | 1.45 |
| 3.58 | II-14 | 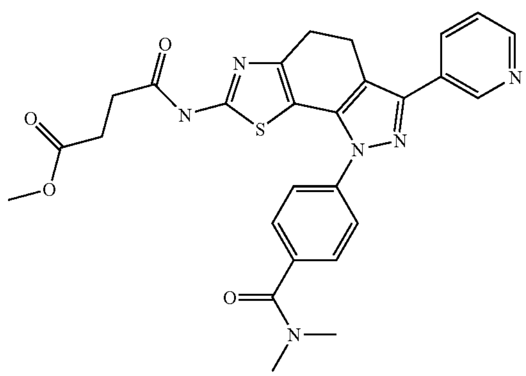 | 531 | 1.48 |
| 3.59 | II-14 | 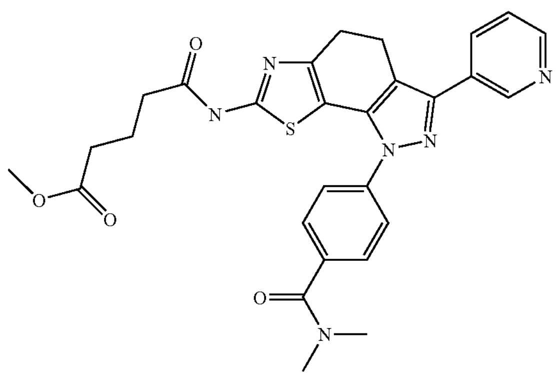 | 545 | 1.56 |

-continued

| # | Starting compound | Structure | Mass [M + 1]+ | HPLC Rt [min] or m.p. or TLC:R_f |
|---|---|---|---|---|
| 3.60 | II-14 | 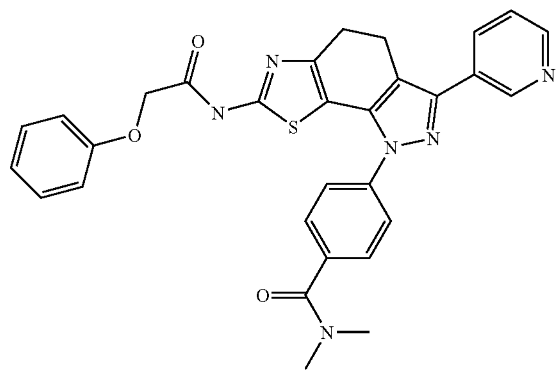 | 551 | 1.77 |
| 3.61 | II-14 | 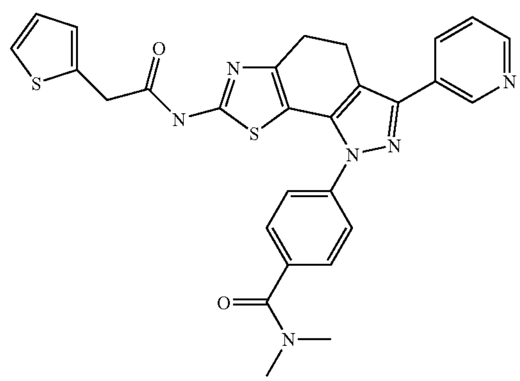 | 541 | 1.67 |
| 3.62 | II-14 | 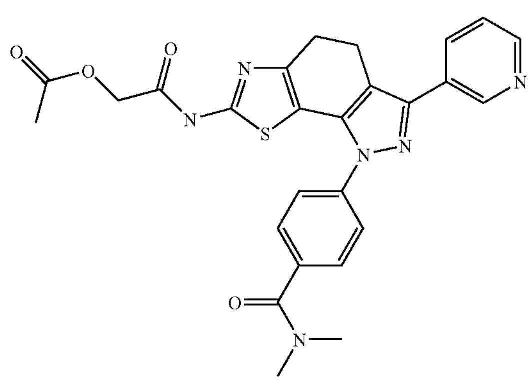 | 517 | 1.46 |
| 3.63 | II-14 | 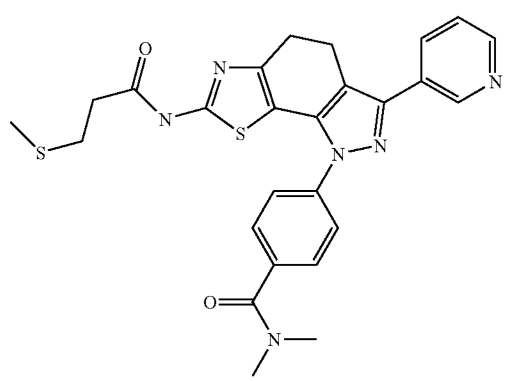 | 519 | 1.57 |

US 7,691,888 B2

195                                                                                       196

-continued

| # | Starting compound | Structure | Mass [M + 1]⁺ | HPLC Rt [min] or m.p. or TLC:R$_f$ |
|---|---|---|---|---|
| 3.64 | II-14 | 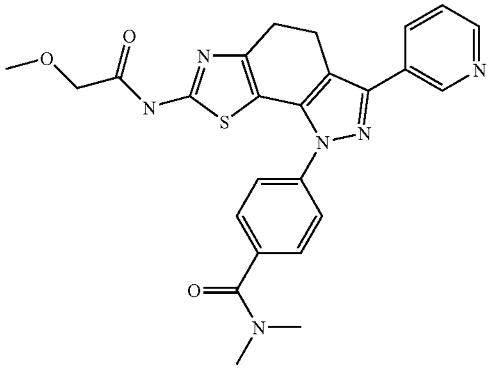 | 489 | 1.45 |
| 3.65 | II-15 | 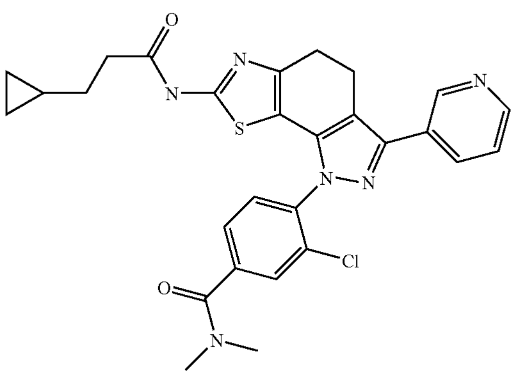 | 547 | 1.74 |
| 3.66 | II-16 | 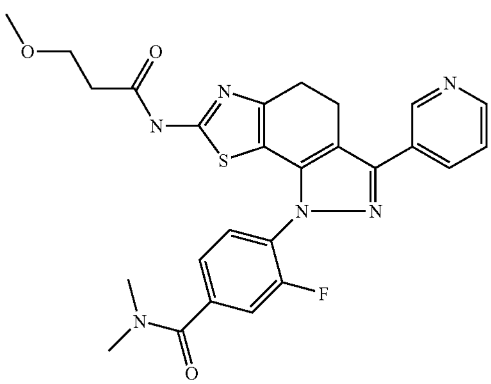 | 521 | 1.46 |
| 3.67 | II-16 | 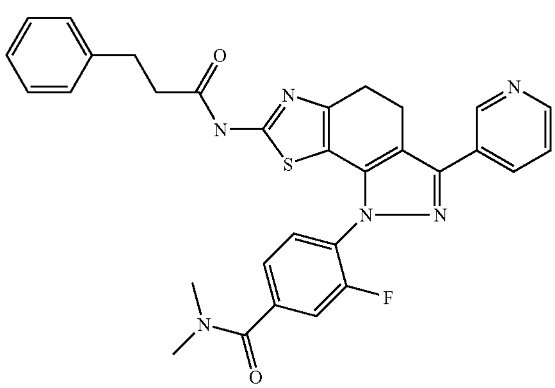 | 567 | 1.77 |

-continued

| # | Starting compound | Structure | Mass [M + 1]+ | HPLC Rt [min] or m.p. or TLC:R_f |
|---|---|---|---|---|
| 3.68 | II-17 | 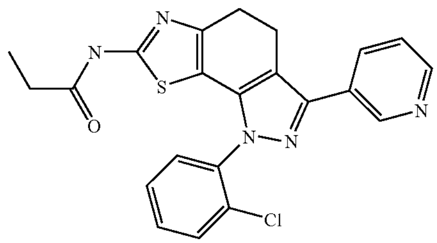 | 436 | 1.64 |
| 3.69 | II-17 | 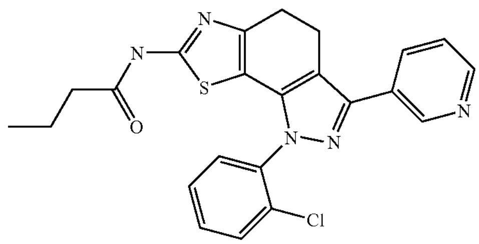 | 450 | 1.75 |
| 3.70 | II-17 | 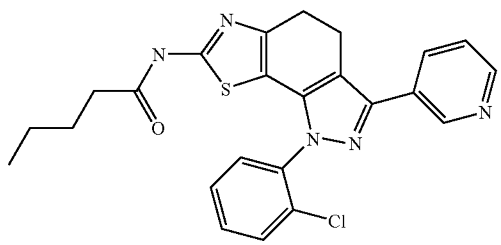 | 464 | 1.87 |
| 3.71 | II-17 | 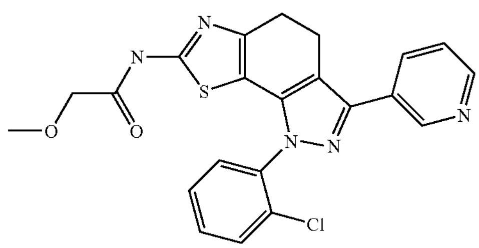 | 452 | 1.59 |
| 3.72 | II-17 | 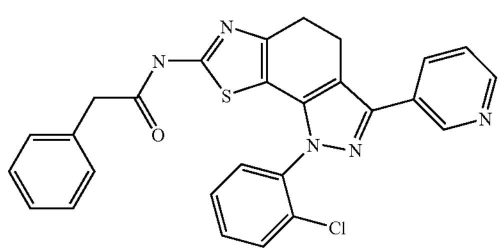 | 498 | 1.88 |
| 3.73 | II-17 | 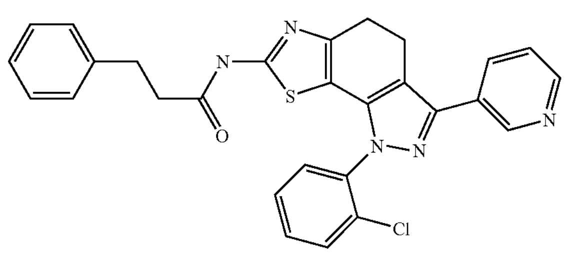 | 512 | 1.95 |

-continued
| # | Starting compound | Structure | Mass [M + 1]+ | HPLC Rt [min] or m.p. or TLC:R_f |
|---|---|---|---|---|
| 3.74 | II-17 | 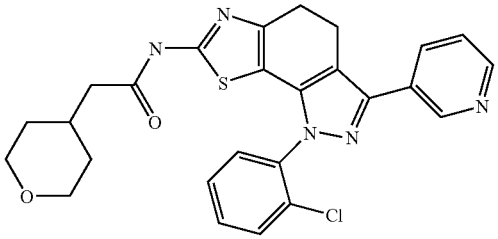 | 506 | 1.68 |
| 3.75 | II-17 | 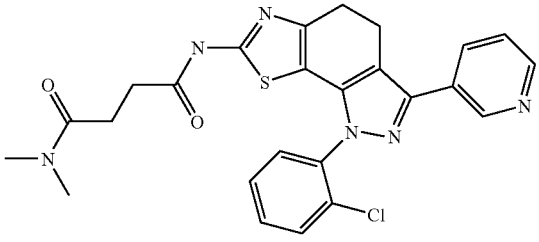 | 507 | 1.57 |
| 3.76 | II-17 | 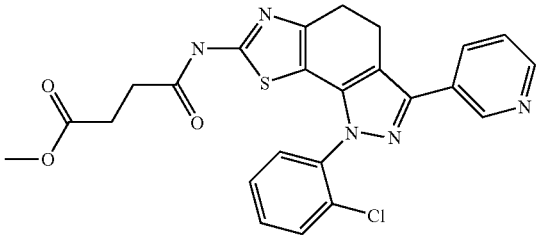 | 494 | 1.64 |
| 3.77 | II-17 | 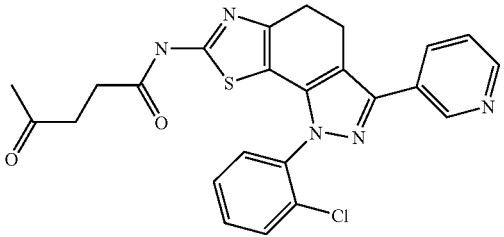 | 478 | 1.58 |
| 3.78 | II-17 | 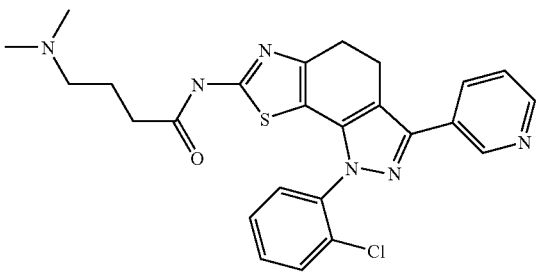 | 493 | 1.28 |

-continued

| # | Starting compound | Structure | Mass [M + 1]⁺ | HPLC Rt [min] or m.p. or TLC:R$_f$ |
|---|---|---|---|---|
| 3.79 | II-17 | 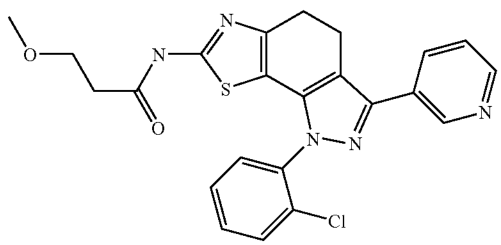 | 466 | 1.61 |
| 3.80 | II-18 | 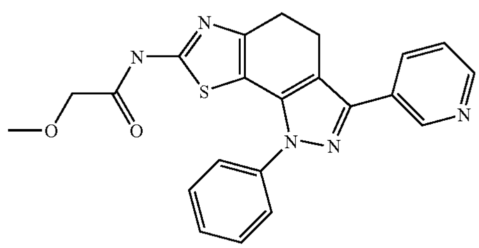 | 418 | 1.54 |
| 3.81 | II-18 | 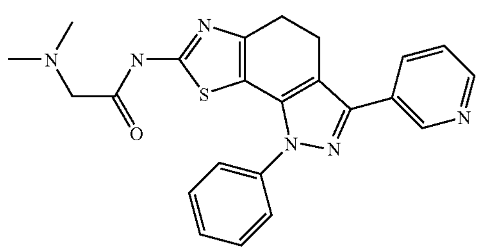 | 431 | 1.53 |
| 3.82 | II-18 | 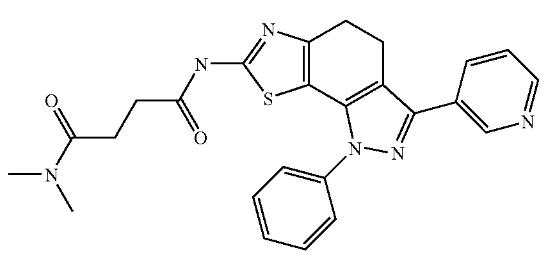 | 473 | 1.55 |

* 3.56 is synthesized by reacting II-4 with 2-bromopropionyl bromide and then performing a nucleophilic substitution with dimethylamine.

Examples 4

Reacting the Thiocarbamates with Amines and Alcohols

Preparing Ureas 0.17 mmol of amine and 30 µl of diisopropylethylamine are added to a solution of 0.11 mmol of thiocarbamate in 5 ml of ethanol and the mixture is stirred at 80° C. for 15 h in a pressure tube. After the solvent has been removed in vacuo, the residue is purified chromatographically.

Preparing Carbamates 5 ml of the appropriate alcohol are added to a solution of 0.11 mmol of thiocarbamate (or methylcarbamate) and the mixture is stirred at 80° C. for 15 h in a pressure tube. After the solvent has been removed in vacuo, the residue is purified chromatographically.

Examples 4.1-4.32

| # | Starting compound | Structure | Mass [M + 1]⁺ | HPLC Rt [min] or m.p. or TLC:R_f |
|---|---|---|---|---|
| 4.1 | II-9 | | 508 | 1.43 |

$^1$H-NMR DMSO-d6, d [ppm]: 893 (d, 1.7 Hz, 1H), 8.79 (s, 1H), 8.58 (dd, 1.5 and 4.8 Hz, 1H), 8.22 (s, 1H), 8.12-8.09 (m, 1H), 7.99 (d, 2.1 Hz, 1H), 7.70 (dd 2.3 and 8.8 Hz, 1H), 7.54-7.47 (m, 2H), 3.17-3.12 (m, 2H), 3.05-3.01(m, 2H), 2.9 (s, 6H), 2.08 (s, 3H).

| # | Starting compound | Structure | Mass [M + 1]⁺ | HPLC Rt [min] |
|---|---|---|---|---|
| 4.2 | II-9 | 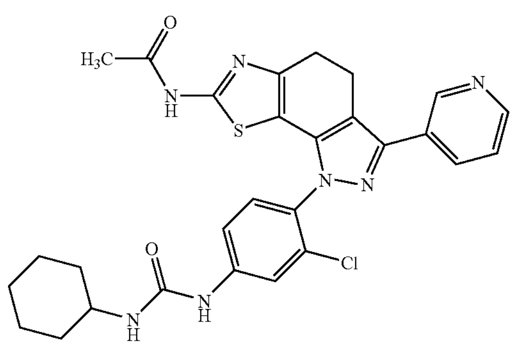 | 562 | 1.86 |
| 4.3 | II-9 | 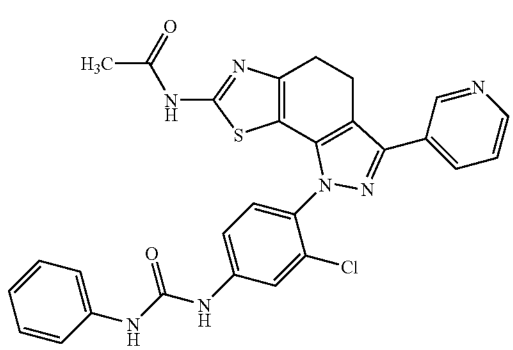 | 556 | 1.85 |

-continued

| # | Starting compound | Structure | Mass [M + 1]+ | HPLC Rt [min] or m.p. or TLC:R_f |
|---|---|---|---|---|
| 4.4 | II-9 | 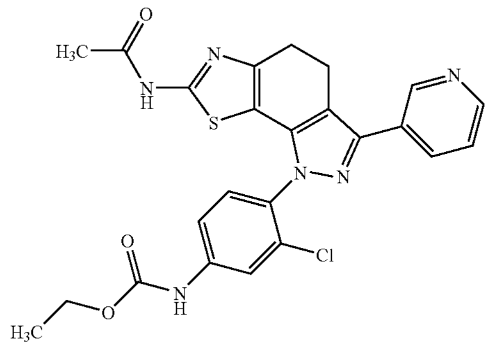 | 509 | 1.73 |
| 4.5 | II-9 | 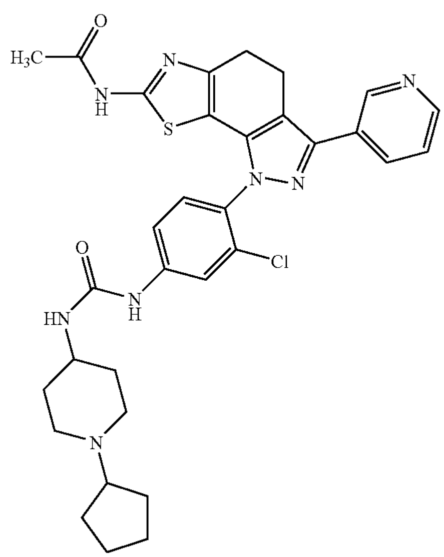 | 631 | 1.58 |
| 4.6 | II-9 | 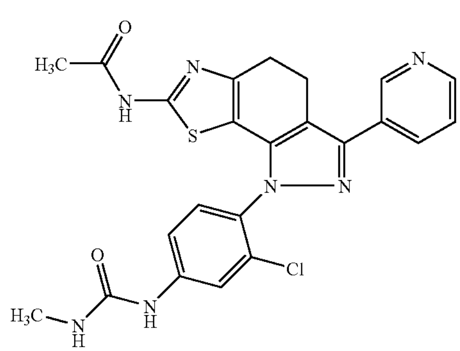 | 493 | 2.02 |

-continued

| # | Starting compound | Structure | Mass [M + 1]+ | HPLC Rt [min] or m.p. or TLC:R_f |
|---|---|---|---|---|
| 4.7 | II-9 | 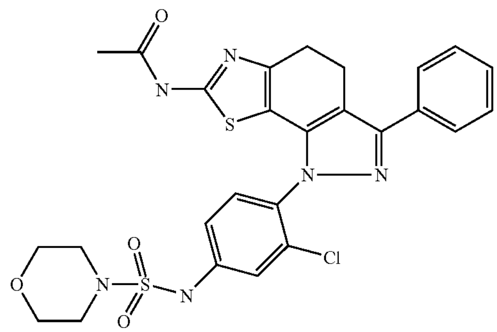 | 585 | m.p.: 160° C. |
| 4.8 | II-9 | 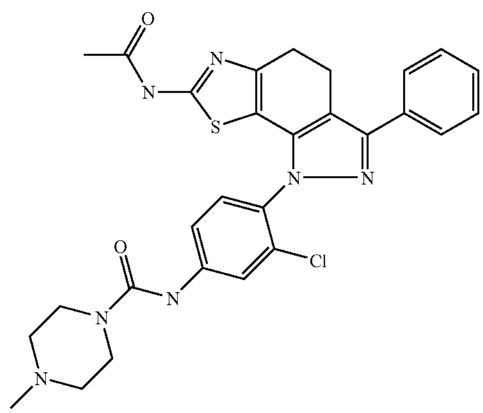 | 562 | 1.59 |
| 4.9 | II-9 | 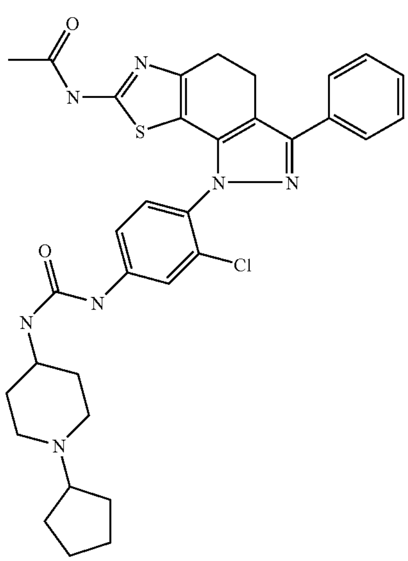 | 630 | 1.68 |

| # | Starting compound | Structure | Mass [M + 1]⁺ | HPLC Rt [min] or m.p. or TLC:R$_f$ |
|---|---|---|---|---|
| 4.10 | II-9 | 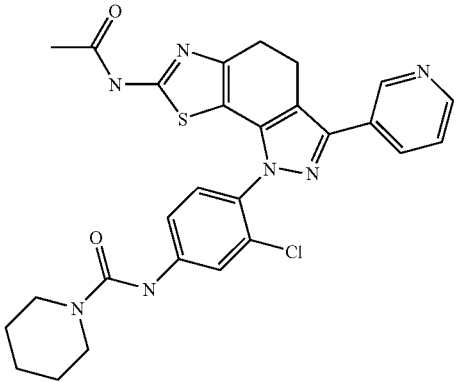 | 549 | 1.65 |
| 4.11 | II-9 | 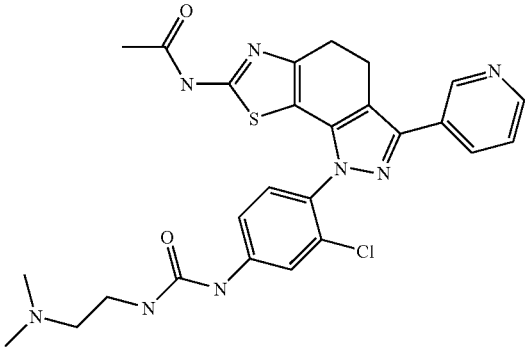 | 551 | R$_f$ = 0.02 DCM:MeOH 9:1 |
| 4.12 | II-9 | 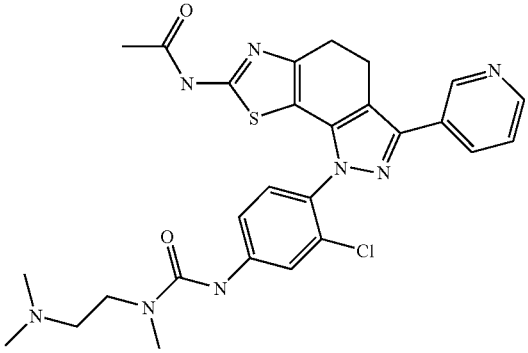 | 565 | R$_f$ = 0.05 DCM:MeOH 9:1 |
| 4.13 | II-9 | 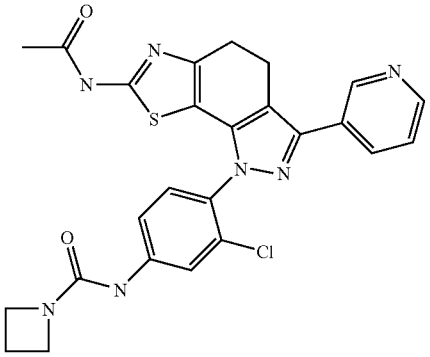 | 520 | 1.43 |

-continued
| # | Starting compound | Structure | Mass [M + 1]⁺ | HPLC Rt [min] or m.p. or TLC:R_f |
|---|---|---|---|---|
| 4.14 | II-9 | 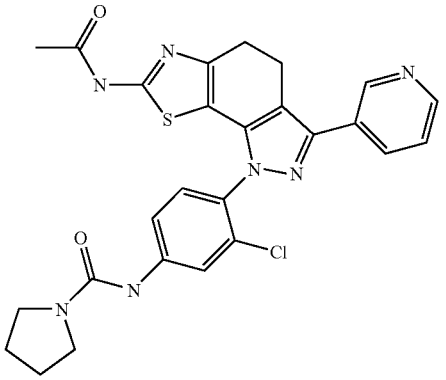 | 534 | 1.54 |
| 4.15 | II-9 | 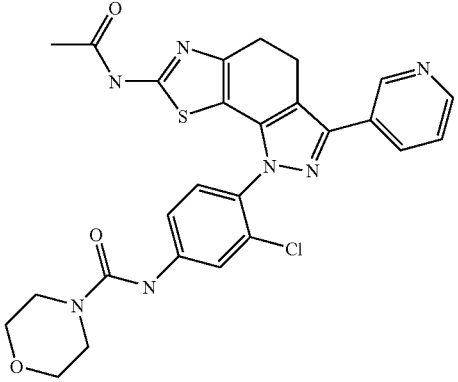 | 550 | 1.43 |
| 4.16 | II-9 | 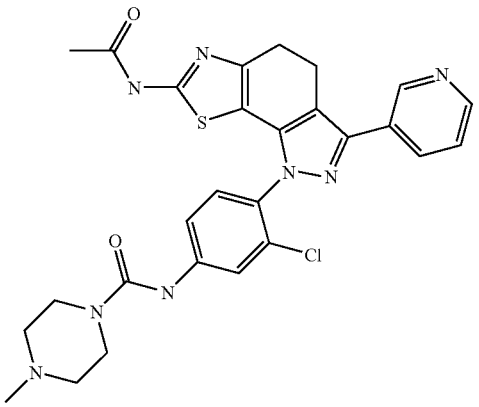 | 563 | 1.3 |

-continued

| # | Starting compound | Structure | Mass [M + 1]+ | HPLC Rt [min] or m.p. or TLC:R$_f$ |
|---|---|---|---|---|
| 4.17 | II-9 | 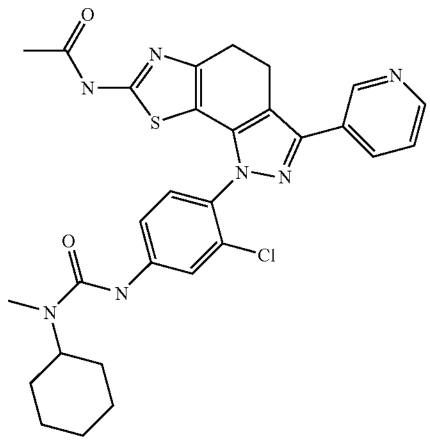 | 576 | 1.83 |
| 4.18 | II-9 | 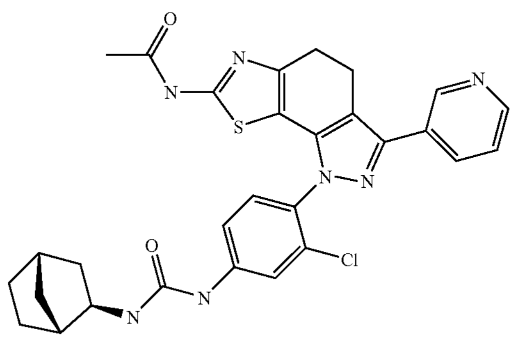 | 574 | 1.79 |
| 4.19 | II-9 | 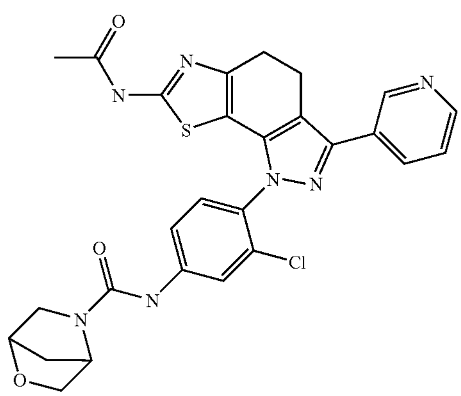 | 562 | 1.42 |
| 4.20 | II-9 | 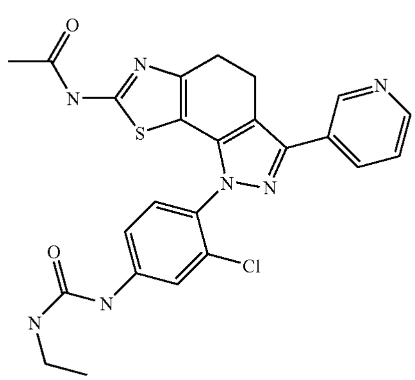 | 508 | 1.49 |

-continued

| # | Starting compound | Structure | Mass [M + 1]+ | HPLC Rt [min] or m.p. or TLC:R_f |
|---|---|---|---|---|
| 4.21 | II-9 | 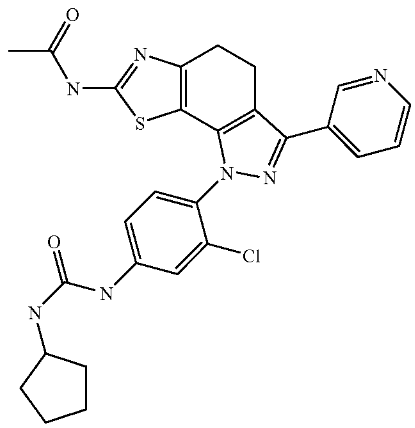 | 548 | 1.68 |
| 4.22 | 2.176 | 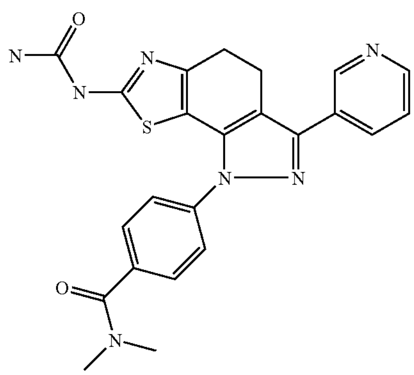 | 460 | 1.43 |
| 4.23 | 2.176 | 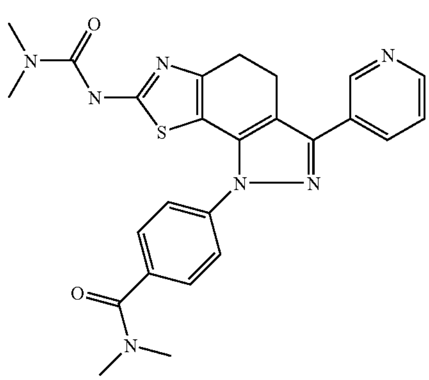 | 488 | 1.45 |

-continued
| # | Starting compound | Structure | Mass [M + 1]+ | HPLC Rt [min] or m.p. or TLC:R_f |
|---|---|---|---|---|
| 4.24 | 2.177 | 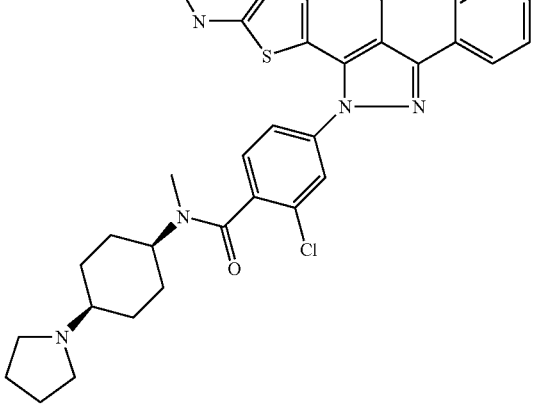 | 685 | 1.49 |
| 4.25 | 2.177 | 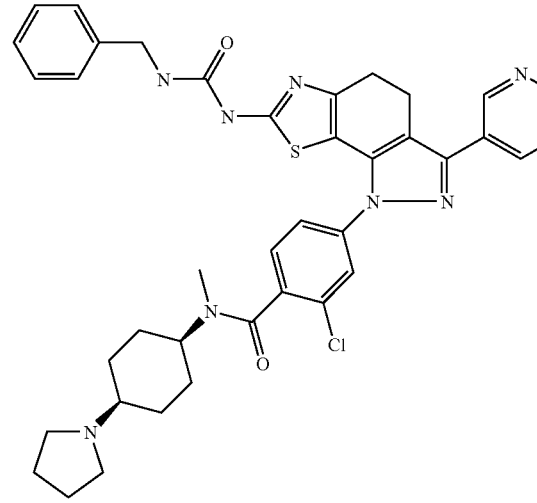 | 721 | 1.55 |
| 4.26 | 2.178 | 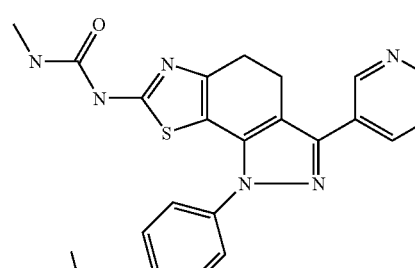 | 508 | 1.58 |

-continued

| # | Starting compound | Structure | Mass [M + 1]+ | HPLC Rt [min] or m.p. or TLC:R_f |
|---|---|---|---|---|
| 4.27 | I-43 | 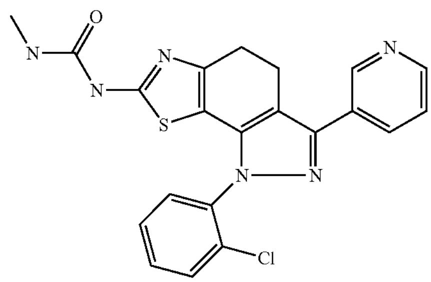 | 437 | 1.59 |
| 4.28 | I-44 | 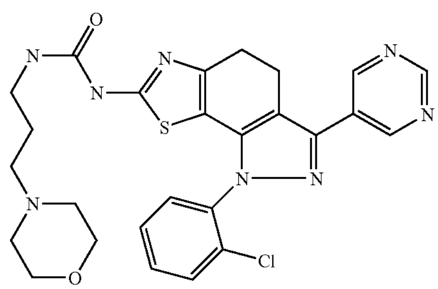 | 551 | m.p.: 199° C. |
| 4.29 | I-44 | 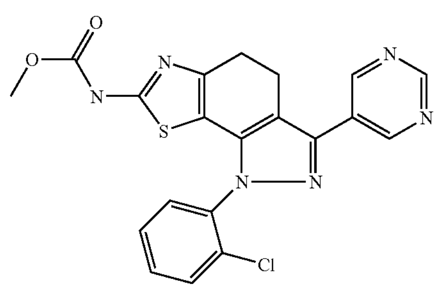 | 439 | m.p.: 273° C. |
| 4.30 | I-44 | 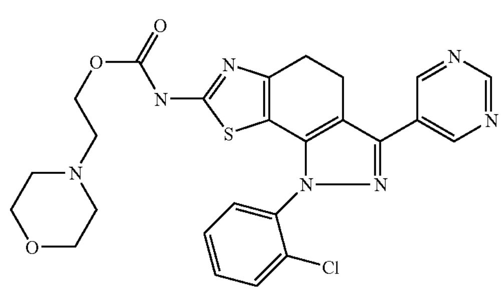 | 538 | m.p.: 220° C. |

-continued

| # | Starting compound | Structure | Mass [M + 1]⁺ | HPLC Rt [min] or m.p. or TLC:R$_f$ |
|---|---|---|---|---|
| 4.31 | I-43 | 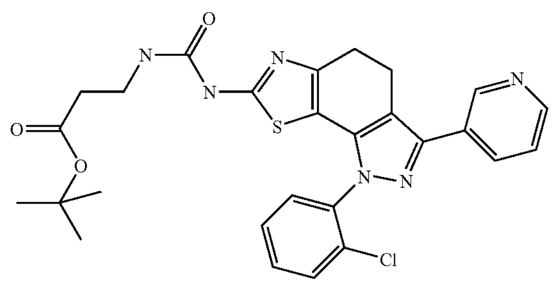 | 551 | 1.94 |
| 4.32 | I-1 | 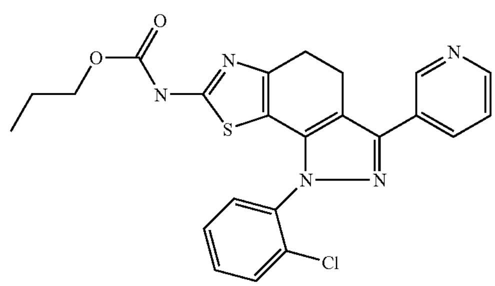 | 466 | 3.61 |

Examples 5

Reacting the Chloropyridyl Building Blocks

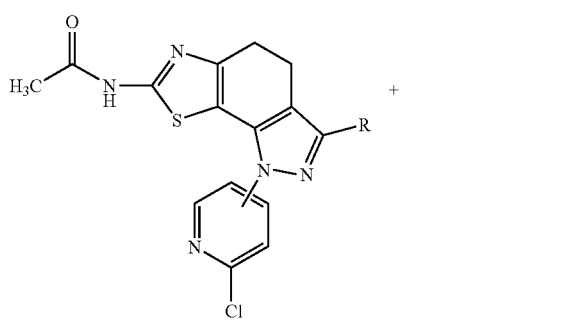

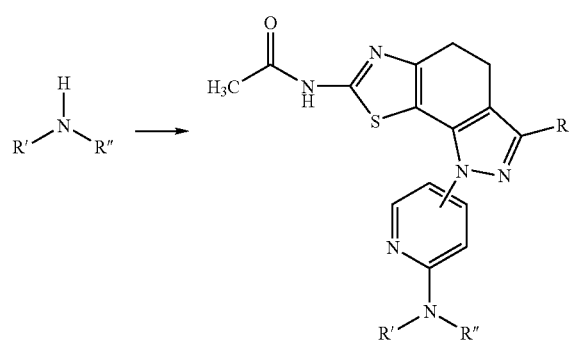

Synthesis Method H

If the amines are present in liquid form, 0.2 mmol of the chloropyridine building block is dissolved in 0.5 ml of amine and the solution is heated at 120° C. for 10 min in a microwave (CEM). After the excess amine has been removed, the residue is purified chromatographically.

Synthesis Method I

A solution of 1.2 mmol of chloropyridine building block and 3 mmol of amine in 3 ml of N-methylpyrrolidinone, DMSO or DMF is heated at 120° C. for 10 min in a microwave (CEM). After the solvent and the excess amine have been removed, the residue is purified chromatographically.

Examples 5.1-5.23

| # | Starting compound | Structure | Mass [M + 1]⁺ | HPLC Rt [min] or m.p. or TLC:R_f |
|---|---|---|---|---|
| 5.1 | I-3 | *(structure)* H-NMR DMSO-d-6, d [ppm]: 8.28 (d, 5.4 Hz, 1H), 7.79 (s, 1H), 7.05 (s, 1H), 6.9-6.88 (m, 1H), 6.8 (d, 3.3 Hz, 1H), 6.64-6.62 (m, 1H), 3.72-3.67 (m, 2H), 3.58-3.55 (m, 2H), 3.11-3.06 (m, 2H), 3.04-3.00 (m, 2H), 2.13 (s, 3H). | 463 | 1.67 |
| 5.2 | I-3 | *(structure)* | 421 | 1.44 |
| 5.3 | I-14 | *(structure)* | 462 | 0.3 |

-continued

| # | Starting compound | Structure | Mass [M + 1]+ | HPLC Rt [min] or m.p. or TLC:R_f |
|---|---|---|---|---|
| 5.4 | I-14 | 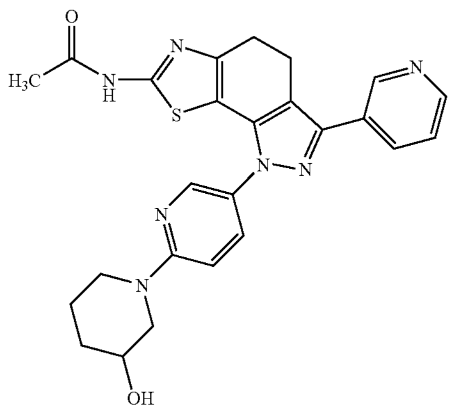 | 488 | 0.28 |
| 5.5 | I-14 | 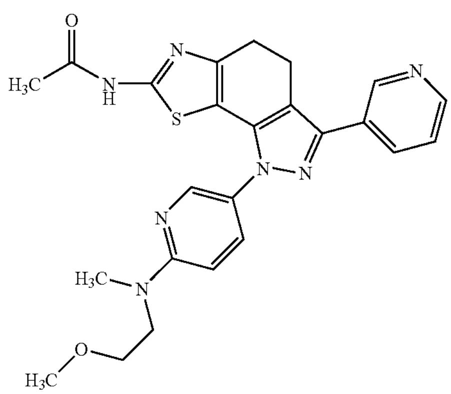 | 476 | 1.5 |
| 5.6 | I-14 | 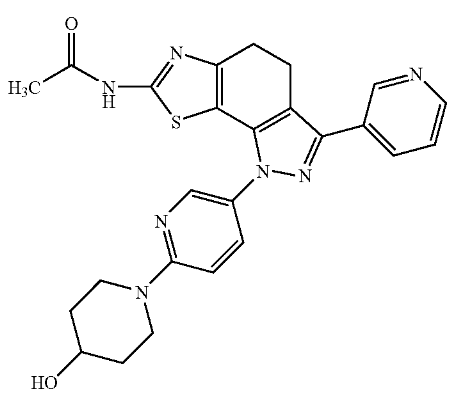 | 488 | 1.34 |

-continued

| # | Starting compound | Structure | Mass [M + 1]+ | HPLC Rt [min] or m.p. or TLC:R$_f$ |
|---|---|---|---|---|
| 5.7 | I-14 | 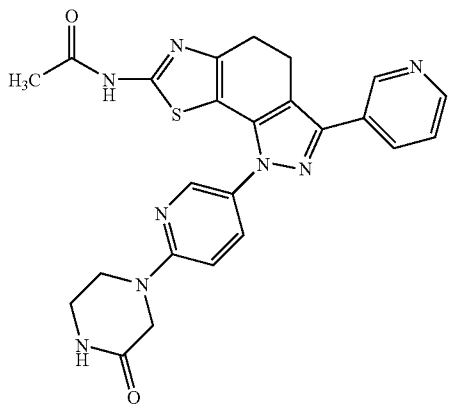 | 487 | 1.35 |
| 5.8 | I-14 | 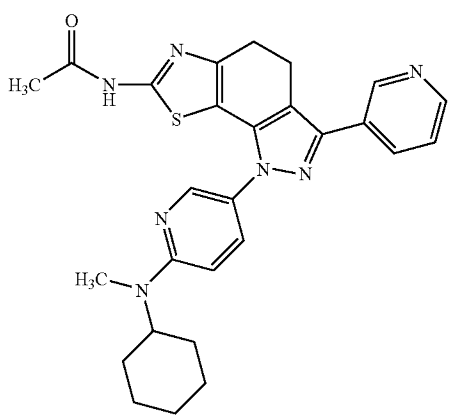 | 500 | 1.89 |
| 5.9* | I-14 | 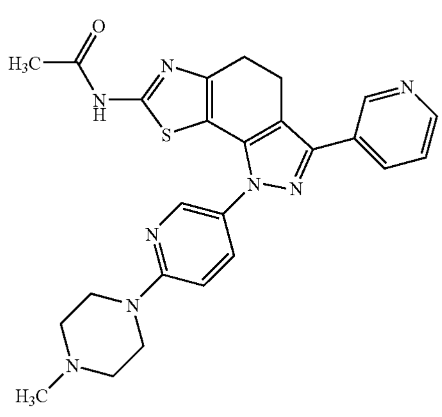 | 487 | 1.16 |

-continued

| # | Starting compound | Structure | Mass [M + 1]⁺ | HPLC Rt [min] or m.p. or TLC:R_f |
|---|---|---|---|---|
| 5.9b | I-14 | 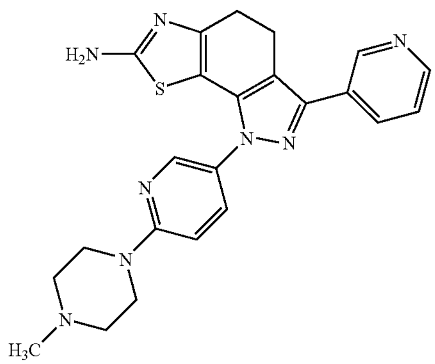 | 445 | R_f = 0.02 DCM:MeOH 9:1 |
| 5.10 | I-14 | 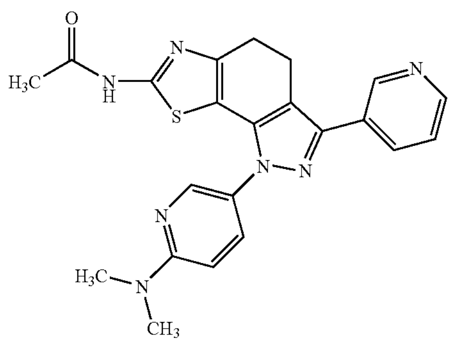 | 432 | 1.26 |
| 5.11 | I-14 | 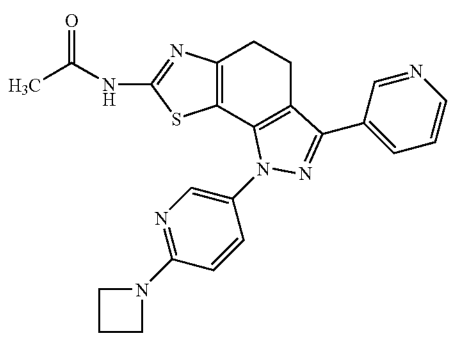 | 444 | 1.31 |
| 5.12 | I-14 | 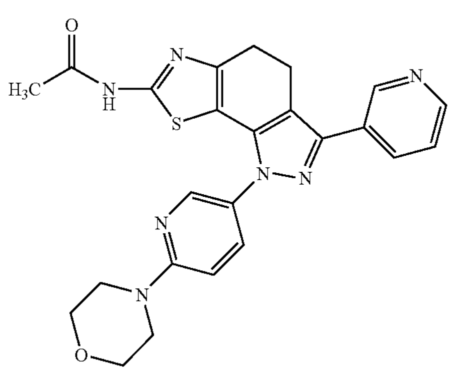 | 474 | 1.52 |

-continued

| # | Starting compound | Structure | Mass [M + 1]+ | HPLC Rt [min] or m.p. or TLC:R$_f$ |
|---|---|---|---|---|
| 5.13 | I-14 | 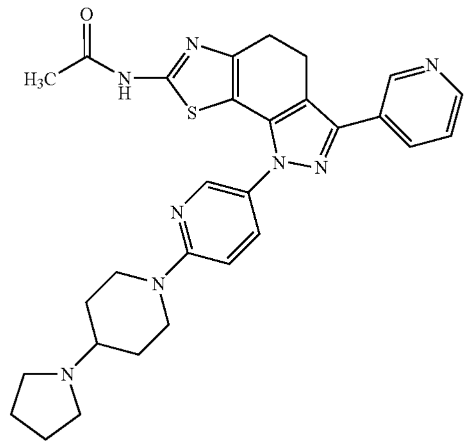 | 541 | 2.93 |
| 5.14 | I-14 | 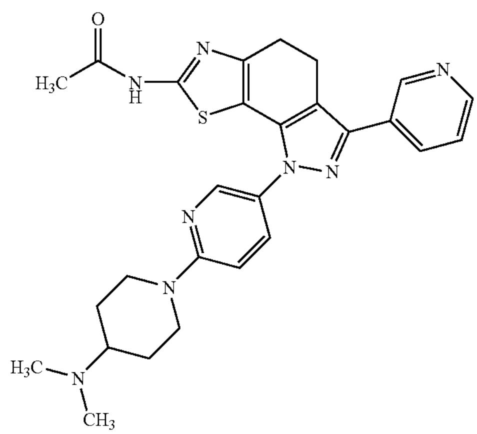 | 515 | 2.78 |
| 5.15 | I-14 | 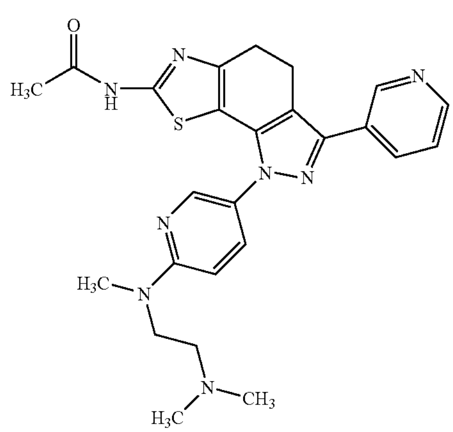 | 489 | 1.26 |

-continued

| # | Starting compound | Structure | Mass [M + 1]⁺ | HPLC Rt [min] or m.p. or TLC:R_f |
|---|---|---|---|---|
| 5.16* | I-14 | 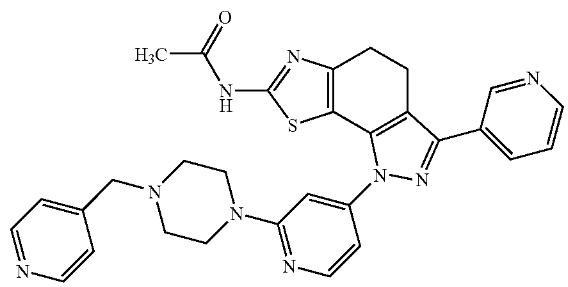 | 564 | R_f = 0.56 MeOH |
| 5.16b | I-15 | 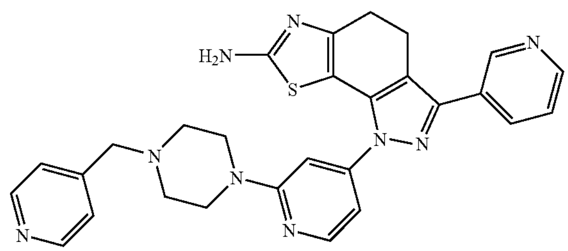 | 522 | 1.13 |
| 5.17 | I-15 | 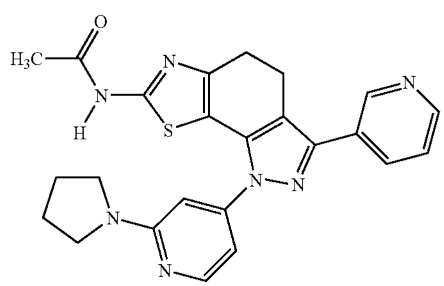 | 458 | R_f = 0.41 DCM:MeOH 8:2 |
| 5.18 | I-15 | 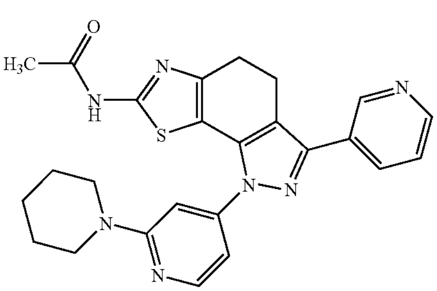 | 472 | 1.36 |

-continued

| # | Starting compound | Structure | Mass [M + 1]+ | HPLC Rt [min] or m.p. or TLC:R_f |
|---|---|---|---|---|
| 5.19 | I-14 | 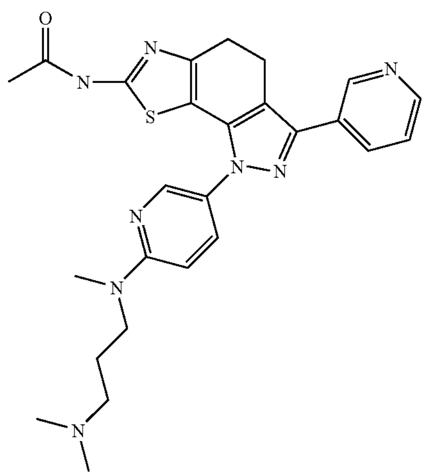 | 503 | R_f = 0.06 DCM:MeOH 9:1 |
| 5.20 | I-14 | 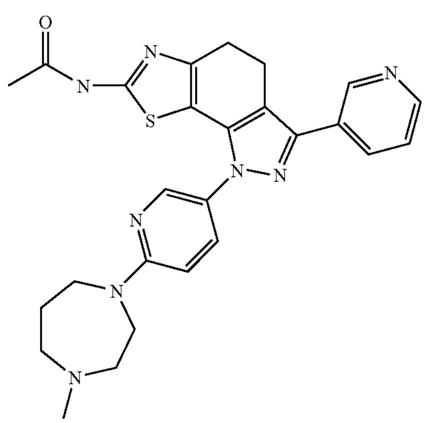 | 501 | R_f = 0.08 DCM:MeOH 9:1 |
| 5.21 | I-14 | 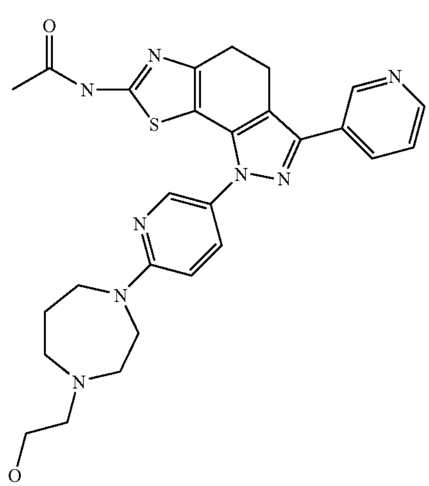 | 531 | 1.17 |

| # | Starting compound | Structure | Mass [M + 1]+ | HPLC Rt [min] or m.p. or TLC:R$_f$ |
|---|---|---|---|---|
| 5.22 | I-14 | 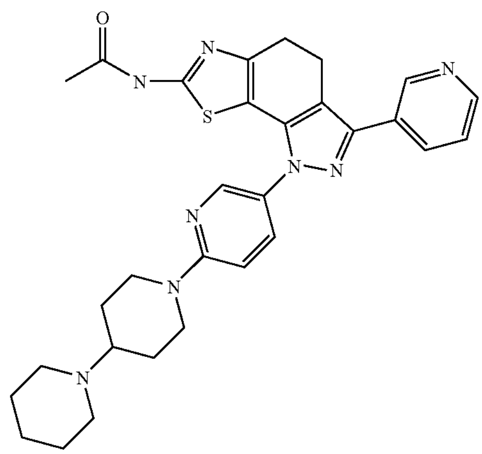 | 555 | 1.28 |
| 5.23* | I-14 | 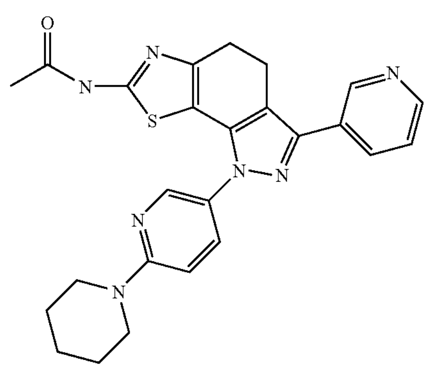 | 472 | 3.35 |
| 5.23b | I-14 | 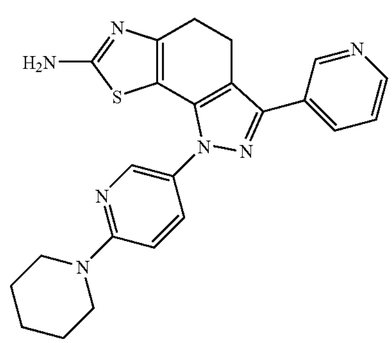 | 430 | 3.12 |

*Under the reaction conditions, the acetyl group is observed to be eliminated. The corresponding isolated free amine in Examples 5.9b, 5.16b and 5.23b is reacetylated with acetic anhydride in dioxane.

Examples 6

Reductive Amination

Method J

A solution of 70 mg of II-10 (0.15 mmol) and 22 of N-methylpiperidin-4-one (0.18 mmol) in 5 ml of dichloromethane is stirred at RT for 2 h. After 40 mg of sodium triacetoxyborohydride (0.18 mmol) have been added, the reaction mixture is stirred for a further 15 h. The mixture is diluted with dichloromethane and washed with a dilute solution of sodium hydrogen carbonate; the organic phase is dried and evaporated. The residue is solubilized in a very small quantity of ethyl acetate/methanol and crystallized using diethyl ether. The crystals which have precipitated out are filtered off and dried in vacuo.

Method K

A solution of 220 mg of II-11 (0.5 mmol) and 0.1 ml of benzylamine (1 mmol) in 5 ml of methanol is stirred at 60° C. for 15 h after which 155 mg of sodium triacetoxyborohydride (0.7 mmol) and 40 mg of sodium acetate (0.5 mmol) are added. Following hydrolysis with sodium hydrogen carbonate and extraction with dichloromethane, the organic phase is dried and evaporated and the residue is purified chromatographically.

Examples 6.1-6.4

| # | Starting compound | Method | Structure | Mass [M + 1]$^+$ | HPLC:Rt [min] or m.p. or TLC:R$_f$ |
|---|---|---|---|---|---|
| 6.1 | II-10 | I | 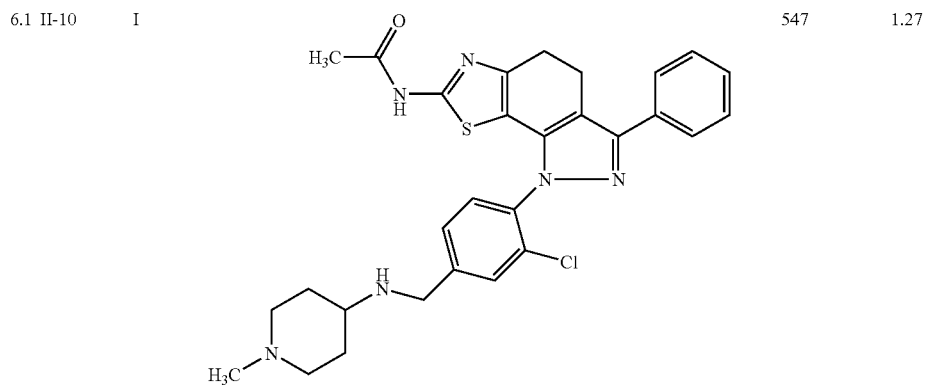 | 547 | 1.27 |
| 6.2 | II-11 | K | 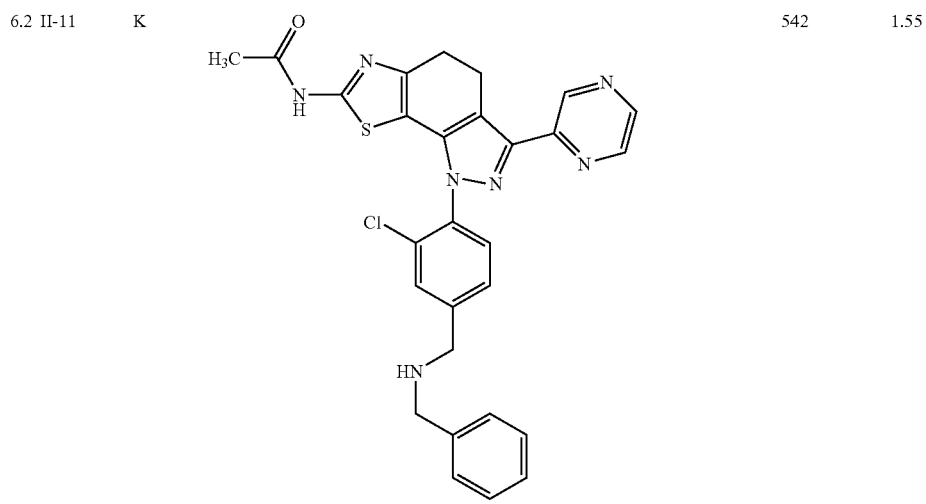 | 542 | 1.55 |

-continued

| Starting # compound | Method | Structure | Mass [M + 1]⁺ | HPLC:Rt [min] or m.p. or TLC:R_f |
|---|---|---|---|---|
| 6.3 II-11 | K | | 603 | 0.30 |
| 6.4 II-12 | I | | 541 | m.p.: 166° C. |

Examples 7

Synthesis Method L—Crosscoupling with Arylboronic Acids 0.3 mmol of the appropriate boronic acid is added to a suspension of 100 mg of I-24 (0.2 mmol) in 3 ml of acetone. 4.4 mg of palladium(II) acetate (19 mmol), 4 µl of diazabicyclooctane (39 mmol) and 80 mg of potassium carbonate are then added and the reaction vessel is heated at 100° C. for 20 min in a microwave; after that, it is heated a further 2× for in each case 40 min at 120° C. and 70° C. After the solvent has been removed, the reaction mixture is purified chromatographically.

Synthesis Method M—Crosscoupling with Alkynes 56 mg of N,N-dimethylaminoprop-2-yne (0.7 mmol) and diisopropylethylamine are added, while stirring and under an argon atmosphere, to a solution of 200 mg of I-31 (0.3 mmol), 6 mg of copper(I) iodide (34 mmol) and 24 mg of triphenylphosphinepalladium(II) chloride (34 mmol) in 25 ml of degassed THF and the reaction mixture is stirred at 80° C. for 15 h. 100 µl of alkyne, as well as 10 mg of CuI and 20 mg of Pd catalyst, are added and the mixture is left to stir at 55° C. for a further 24 h. The mixture is then made alkaline with an aqueous solution of NH₃, diluted with water and extracted 2× with THF. The combined organic phases are extracted by shaking with a saturated solution of NaCl, dried, filtered and evaporated. The residue is purified chromatographically.

Synthesis Method N—Palladium-Catalysed Amination 30 mg of tri-tert-butylphosphine tetrafluoroborate (0.1 mmol) are added to a solution of 200 mg of I-31 (0.3 mmol), 38 mg of 4-aminopyridine (0.4 mmol), 47 mg of tris(dibenzylideneacetone)dipalladium (51 mmol) and 111 mg of sodium tert-butoxide (1 mmol) in 4 ml of degassed DMF and the mixture is stirred at 90° C. for 4 h under argon. Following hydrolysis with phosphate buffer and water, the mixture is extracted with dichloromethane. The organic phase is dried, filtered and evaporated and the residue is purified chromatographically.

Examples 7.1-7.8

| # | Starting compound | Structure | Mass [M + 1]⁺ | HPLC Rt [min] |
|---|---|---|---|---|
| 7.1 | I-24 | 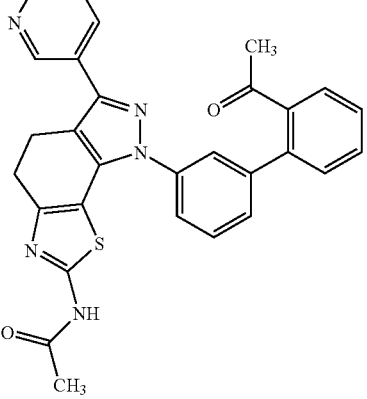 ¹H-NMR DMSO-d-6, d [ppm]: 8.95 (s, 1H), 8.61-8.58 (m,1H),8.14-8.11 (m, 1H), 7.67-7.65 (m,2H),7.63-7.58 (m, 3H), 7.56-7.48 (m, 2H),7.45-7.41 (m, 1H), 3.17-3.12 (m,2H),3.06-3.01 (m, 2H), 2.26 (s, 3H), 2.10 (s, 3H). | 506 | 1.83 |
| 7.2 | I-24 | 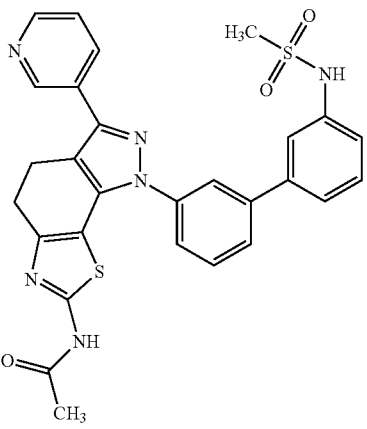 | 557 | 3.63 |

-continued
| # | Starting compound | Structure | Mass [M + 1]+ | HPLC Rt [min] |
|---|---|---|---|---|
| 7.3 | I-24 | 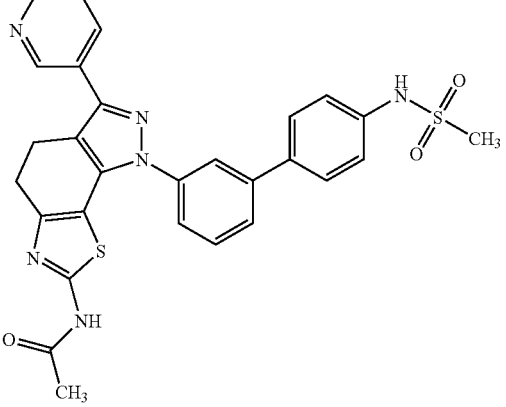 | 557 | 3.24 |
| 7.4 | I-24 | 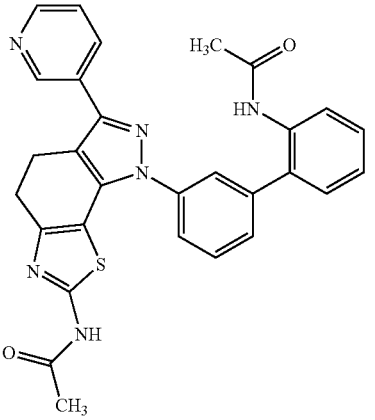 | 521 | 1.66 |
| 7.5 | I-24 | 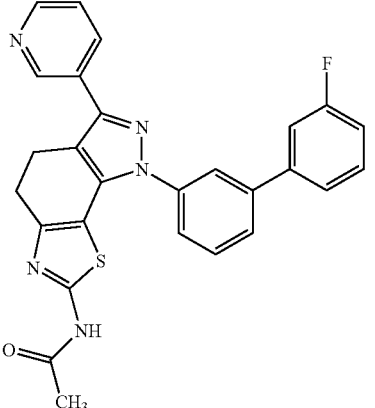 | 482 | 3.57 |

-continued

| # | Starting compound | Structure | Mass [M + 1]⁺ | HPLC Rt [min] |
|---|---|---|---|---|
| 7.6 | I-24 | 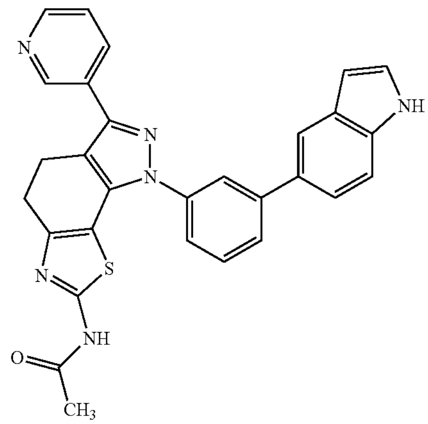 | 503 | 1.89 |
| 7.7 | I-31 | 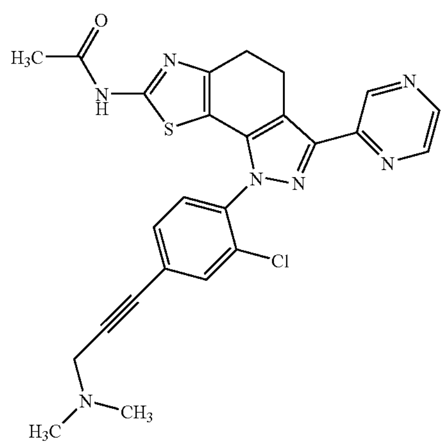 | 504 | 1.47 |
| 7.8 | I-31 | 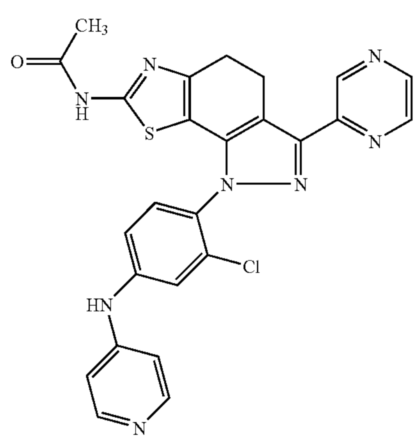 | 515 | 1.47 |

Example 8

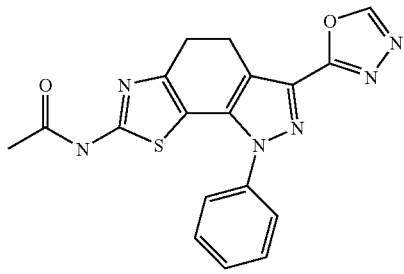

60 mg of N-(3-hydrazinocarbonyl-1-phenyl-4,5-dihydro-1H-pyrazolo[3',4':3,4]benzo[1,2-d]thiazol-7-yl)-acetamide (0.16 mmol), which can be prepared from I-6 and hydrazine in accordance with synthesis method B, are treated with 3 ml of triethyl orthoformate at 180° C. for 30 min in a microwave.

After the excess ortho ester has been removed in vacuo, the residue is purified chromatographically. Yield 4 mg

[M+1]⁺=379

Rt=1.75 min.

Examples 9.1-9.4

The following compounds are prepared in analogy with the synthesis of Example II-2.

| # | Starting compound | Structure | [M + 1]⁺ | Rt [min] |
|---|---|---|---|---|
| 9.1 | I-34 | 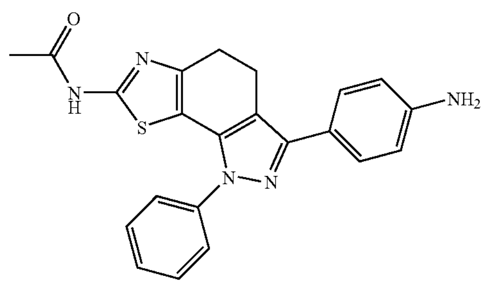 | 402 | 1.63 |

$^1$H-NMR DMSO-d6, d [ppm]: 7.61-7.51 (m, 5H), 7.40 (d, 8.5 Hz, 2H), 6.64 (d, 8.5 Hz, 2H), 3.06-2.95 (m, 4H), 2.09 (s, 3H).

| 9.2 | I-33 | | 436 | 1.67 |
| 9.3 | I-32 | | 402 | 1.56 |

-continued

| Starting # | compound | Structure | [M + 1]+ | Rt [min] |
|---|---|---|---|---|
| 9.4 | I-35 | 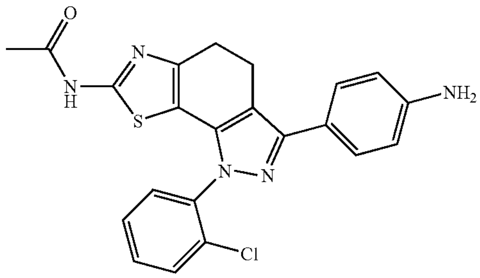 | 436 | 1.66 |

The following example describes the biological effect of the compounds according to the invention without limiting the invention to this example.

HCT116 Cytotoxicity Test

The test is based on the reduction of AlamarBlue (Biosource Int., USA) in living (metabolically active) cells to give a fluorometrically detectable product. The substrate can no longer be reduced in the presence of substances which are toxic to the cells, which means that it is not possible to measure any increase in fluorescence.

HCT116 (human colon carcinoma cell line) cells are sown in microtiter plates and incubated overnight in culture medium at 37° C. and 5% $CO_2$. The test substances are diluted stepwise in medium and added to the cells such that the total volume is 200 µl/well. Cells to which medium, but not substance, is added serve as controls. After an incubation time of 4-6 days, 20 µl of AlamarBlue are added/well and the cells are incubated at 37° C. for a further 6-8 h. For measuring the fluorescence, excitation takes place at a wavelength of 545 nm and the emission is measured at 590 nm.

$EC_{50}$ values are calculated using the GraphPad Prism program.

All the examples cited have an $EC_{50}$ (HCT-116) of less than 5 µM.

The substances of the present invention are PI3 kinase inhibitors. On account of their biological properties, the novel compounds of the general formula (1) and their isomers and their physiologically tolerated salts, are suitable for treating diseases which are characterized by excessive or anomalous cell proliferation.

These diseases include, for example: viral infections (e.g. HIV and Kaposi's sarcoma); inflammation and autoimmune diseases (e.g. colitis, arthritis, Alzheimer's disease, glomerulonephritis and wound healing); bacterial, fungal and/or parasitic infections; leukaemias, lymphomas and solid tumours; skin diseases (e.g. psoriasis); bone diseases; cardiovascular diseases (e.g. restenosis and hypertrophy). In addition, the compounds are useful for protecting proliferating cells (e.g. hair cells, intestinal cells, blood cells and progenitor cells) from DNA damage due to irradiation, UV treatment and/or cytostatic treatment (Davis et al., 2001).

For example, the following cancer diseases can be treated with compounds according to the invention, without, however, being restricted thereto: brain tumours, such as acoustic neurinoma, astrocytomas such as piloid astrocytomas, fibrillary astrocytoma, protoplasmic astrocytoma, gemistocytic astrocytoma, anaplastic astrocytoma and glioblastomas; brain lymphomas, brain metastases, hypophyseal tumour such as prolactinoma, HGH (human growth hormone) producing tumour and ACTH-producing tumour (adrenocorticotrophic hormone), craniopharyngiomas, medulloblastomas, meningiomas and oligodendrogliomas; nerve tumours (neoplasms) such as tumours of the vegetative nervous system such as neuroblastoma sympathicum, ganglioneuroma, paraganglioma (phaeochromocytoma and chromaffinoma) and glomus caroticum tumour, tumours in the peripheral nervous system such as amputation neuroma, neurofibroma, neurinoma (neurilemoma, schwannoma) and malignant schwannoma, as well as tumours in the central nervous system such as brain and spinal cord tumours; intestinal cancer such as rectal carcinoma, colon carcinoma, anal carcinoma, small intestine tumours and duodenal tumours; eyelid tumours such as basalioma or basal cell carcinoma; pancreatic gland cancer or pancreatic carcinoma; bladder cancer or bladder carcinoma; lung cancer (bronchial carcinoma) such as small-cell bronchial carcinomas (oat cell carcinomas) and non-small-cell bronchial carcinomas such as squamous epithelium carcinomas, adenocarcinomas and large-cell bronchial carcinomas; breast cancer such as mammary carcinoma, such as infiltrating ductal carcinoma, colloid carcinoma, lobular invasive carcinoma, tubular carcinoma, adenoid cystic carcinoma, and papillary carcinoma; non-Hodgkin's lymphomas (NHL) such as Burkitt's lymphoma, low-malignancy non-Hodkgin's lymphomas (NHL) and mucosis fungoides; uterine cancer or endometrial carcinoma or corpus carcinoma; CUP syndrome (cancer of unknown primary); ovarian cancer or ovarian carcinoma such as mucinous, endometrial or serous cancer; gall bladder cancer; bile duct cancer such as Klatskin's tumour; testicular cancer such as seminomas and non-seminomas; lymphoma (lymphosarcoma) such as malignant lymphoma, Hodgkin's disease, non-Hodgkin's lymphomas (NHL) such as chronic lymphatic leukaemia, hair cell leukaemia, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as vocal cord tumours, supraglottal, glottal and subglottal laryngeal tumours; bone cancer such as osteochondroma, chondroma, chrondoblastoma, chondromyxoidfibroma, osteoma, osteoid-osteoma, osteoblastoma, eosinophilic granuloma, giant cell tumour, chondrosarcoma, osteosarcoma, Ewing's sarcoma, reticulosarcoma, plasmocytoma, fibrous dysplasia, juvenile bone cyst and aneurysmatic bone cyst; head/neck tumours such as tumours of the lips, tongue, floor of the mouth, oral cavity, gingiva, pallet, salivary glands, pharynx, nasal cavities, paranasal sinuses, larynx and middle ear; liver cancer such as liver cell carcinoma or hepatocellular carcinoma (HCC); leukaemias, such as acute leukaemias, such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or stomach carcinoma such as papillary, tubular and mucinous adenocarcinoma, signet ring cell carcinoma, adenoid squamous cell carcinoma, small-cell carcinoma and undifferentiated carcinoma; melanomas such as superficially spreading, nodular malignant lentigo and acral lentiginous melanoma; renal cancer, such as kidney cell carcinoma or hypernephroma or Grawitz's tumour; oesophageal cancer or oesophageal carcinoma; cancer of the penis; prostate cancer; pharyngeal cancer or pharyngeal carcinomas such as nasopharyngeal carcinomas, oropharyngeal carcinomas and hypopharyngeal carcinomas; retinoblastoma; vaginal cancer or vaginal carcinoma; squamous epithelium carcinomas, adeno carcinomas, in situ carcinomas, malignant melanomas and sarcomas; thyroid gland carcinomas such as papillary, follicular and medullary thyroid gland carcinoma, and also anaplastic carcinomas; spinalioma, prickle cell carcinoma and squamous epithelium carcinoma of the skin; thymomas, urethral cancer and vulvar cancer.

The novel compounds can be used for the prevention or short-term or long-term treatment of the abovementioned diseases including, where appropriate, in combination with other state-of-the-art compounds such as other anti-tumour substances, cytotoxic substances, cell proliferation inhibitors, antiangiogenic substances, steroids or antibodies.

The compounds of the general formula (1) can be used on their own or in combination with other active compounds according to the invention and, where appropriate, in combination with other pharmacologically active compounds as well. Chemotherapeutic agents which can be administered in combination with the compounds according to the invention include, without being restricted thereto, hormones, hormone analogs and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone and octreotide), aromatase inhibitors (e.g. anastrozole, letrozole, liarozole, vorozole, exemestane and atamestane), LHRH agonists and antagonists (e.g. goserelin acetate and luprolide), inhibitors of growth factors (growth factors such as platelet-derived growth factor and hepatocyte growth factor, examples of inhibitors are growth factor antibodies, growth factor receptor antibodies and tyrosine kinase inhibitors, such as gefitinib, imatinib, lapatinib and trastuzumab); antimetabolites (e.g. antifolates such as methotrexate and raltitrexed, pyrimidine analogs such as 5-fluorouracil, capecitabine and gemcitabine, purine and adenosine analogs such as mercaptopurine, thioguanine, cladribine and pentostatin, cytarabine and fludarabine); antitumour antibiotics (e.g. anthracyclines, such as doxorubicin, daunorubicin, epirubicin and idarubicin, mitomycin C, bleomycin, dactinomycin, plicamycin and streptozocin); platinum derivatives (e.g. cisplatin, oxaliplatin and carboplatin); alkylating agents (e.g. estramustine, meclorethamine, melphalan, chlorambucil, busulphan, dacarbazine, cyclophosphamide, ifosfamide and temozolomide, nitrosoureas such as carmustine and lomustine and thiotepa); antimitotic agents (e.g. vinca alkaloids such as vinblastine, vindesine, vinorelbine and vincristine; and taxans such as paclitaxel and docetaxel); topoisomerase inhibitors (e.g. epipodophyllotoxins such as etoposide and etopophos, teniposide, amsacrine, topotecan, irinotecan and mitoxantrone) and various chemotherapeutic agents such as amifostin, anagrelide, clodronate, filgrastin, interferon alpha, leucovorin, rituximab, procarbazine, levamisole, mesna, mitotan, pamidronate and porfimer.

Examples of suitable forms for use are tablets, capsules, suppositories, solutions, in particular solutions for injection (s.c., i.v., i.m.) and infusion, juices, emulsions or dispersible powders. In this connection, the proportion of the pharmaceutically active compound(s) should in each case be in the range of 0.1-90% by weight, preferably 0.5-50% by weight, of the total composition, that is in quantities which are sufficient to achieve the dosage range which is specified below. If necessary, the doses mentioned can be given several times a day.

Appropriate tablets can be obtained, for example, by mixing the active compound(s) with known auxiliary substances, for example inert diluents, such as calcium carbonate, calcium phosphate or lactose, disintegrants, such as maize starch or alginic acid, binders, such as starch or gelatine, lubricants, such as magnesium stearate or talc, and/or agents for achieving a depot effect, such as carboxymethyl cellulose, cellulose acetate phthalate or polyvinyl acetate. The tablets can also comprise several layers.

Correspondingly, sugar-coated tablets can be produced by coating cores, which have been prepared in analogy with tablets, with agents which are customarily used in sugar coatings, for example collidone or shellac, gum arabic, talc, titanium dioxide or sugar. The core can also comprise several layers in order to achieve a depot effect or to avoid incompatibilities. In the same way, the sugar coating can also comprise several layers in order to achieve a depot effect, with it being possible to use the auxiliary substances which are mentioned above in the case of the tablets.

Juices of the active compounds or active compound combinations according to the invention can additionally comprise a sweetening agent, such as saccharine, cyclamate, glycerol or sugar as well as a taste-improving agent, e.g. flavouring agents such as vanillin or orange extract. They can also comprise suspension aids or thickeners, such as sodium carboxymethyl cellulose, wetting agents, for example condensation products of fatty alcohols and ethylene oxide, or protectants such as p-hydroxybenzoates.

Injection and infusion solutions are produced in a customary manner, e.g. while adding isotonizing agents, preservatives, such as p-hydroxybenzoates, or stabilizers, such as alkali metal salts of ethylenediaminetetraacetic acid, where appropriate using emulsifiers and/or dispersants, with it being possible, for example, to employ, where appropriate, organic solvents as solubilizing agents or auxiliary solvents when using water as diluent, and aliquoted into injection bottles or ampoules or infusion bottles.

The capsules, which comprise one or more active compounds or active compound combinations, can, for example, be produced by mixing the active compounds with inert carriers, such as lactose or sorbitol, and encapsulating the mixture in gelatine capsules. Suitable suppositories can be produced, for example, by mixing with excipients which are envisaged for this purpose, such as neutral fats or polyethylene glycol, or their derivatives.

Auxiliary substances which may be mentioned by way of example are water, pharmaceutically unobjectionable organic solvents, such as paraffins (e.g. petroleum fractions), oils of vegetable origin (e.g. groundnut oil or sesame oil), monofunctional or polyfunctional alcohols (e.g. ethanol or glycerol), carrier substances such as natural mineral powders (e.g. kaolins, argillaceous earths, talc and chalk), synthetic mineral powders (e.g. highly disperse silicic acid and silicates), sugars (e.g. cane sugar, lactose and grape sugar), emulsifiers (e.g. lignin, sulphite waste liquors, methyl cellulose, starch and polyvinylpyrrolidone) and glidants (e.g. magnesium stearate, talc, stearic acid and sodium lauryl sulphate).

Administration is effected in a customary manner, preferably orally or transdermally, in particular and preferably orally. In the case of oral use, the tablets can naturally also comprise, in addition to the abovementioned carrier substances, additives such as sodium citrate, calcium carbonate and dicalcium phosphate together with a variety of further substances such as starch, preferably potato starch, gelatine and the like. It is furthermore also possible to use glidants, such as magnesium stearate, sodium lauryl sulphate and talc, for the tableting. In the case of aqueous suspensions, a variety of taste improvers or dyes can also be added to the active compounds in addition to the abovementioned auxiliary substances.

For parenteral administration, it is possible to employ solutions of the active compounds while using suitable liquid carrier materials. The dosage for intravenous administration is 1-1000 mg per hour, preferably between 5 and 500 mg per hour.

Despite this, it may be necessary, where appropriate, to diverge from the abovementioned quantities, depending on the body weight or the nature of the route of administration, on the individual response to the medicament, on the nature of its formulation and on the time or interval at which the administration is effected. Thus, it may, in some cases, be sufficient to make do with less than the previously mentioned lowest quantity whereas, in other cases, the above-mentioned upper limit has to be exceeded. When relatively large quantities are being administered, it may be advisable to divide these into several single doses which are given over the course of the day.

The following formulation examples illustrate the present invention without, however, restricting its scope:

Pharmaceutical Formulation Examples

| A) Tablets | per tablet |
|---|---|
| Active compound in accordance with formula (1) | 100 mg |
| Lactose | 140 mg |
| Maize starch | 240 mg |
| Polyvinylpyrrolidone | 15 mg |
| Magnesium stearate | 5 mg |
| | 500 mg |

The finely ground active compound, lactose and a part of the maize starch are mixed with each other. The mixture is sieved, after which it is moistened with a solution of polyvinylpyrrolidone in water, kneaded, wet-granulated and dried. The granular material, the remainder of the maize starch and the magnesium stearate are sieved and mixed with each other. The mixture is pressed into tablets of suitable shape and size.

| B) Tablets | per tablet |
|---|---|
| Active compound in accordance with formula (1) | 80 mg |
| Lactose | 55 mg |
| Maize starch | 190 mg |
| Microcrystalline cellulose | 35 mg |
| Polyvinylpyrrolidone | 15 mg |
| Sodium carboxymethyl starch | 23 mg |
| Magnesium stearate | 2 mg |
| | 400 mg |

The finely ground active compound, a part of the maize starch, the lactose, microcrystalline cellulose and polyvinylpyrrolidone are mixed with each other, after which the mixture is sieved and worked, together with the remainder of the maize starch and water, into a granular material, which is dried and sieved. The sodium carboxymethyl starch and the magnesium stearate are then added to the granular material and mixed with it, and the mixture is pressed into tablets of suitable size.

| C) Ampoule solution | |
|---|---|
| Active compound in accordance with formula (1) | 50 mg |
| Sodium chloride | 50 mg |
| Water for injection | 5 ml |

The active compound is dissolved, either at its intrinsic pH or, where appropriate, at pH 5.5-6.5, in water after which sodium chloride is added as isotonizing agent. The resulting solution is rendered pyrogen-free by filtration and the filtrate is aliquoted, under aseptic conditions, into ampoules, which are then sterilized and sealed by melting. The ampoules contain 5 mg, 25 mg and 50 mg of active compound.

What is claimed is:

1. A compound of formula (1),

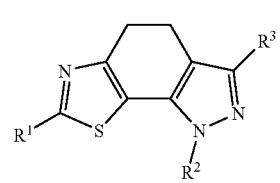

in which $R^1$ is selected from the group consisting of —$NHR^c$, —$NHC(O)R^c$, —$NHC(O)OR^c$, —$NHC(O)NR^cR^c$ and —$NHC(O)SR^c$;

$R^2$ is a radical which is optionally substituted by one or more $R^4$ and which is selected from the group consisting of $C_{1-6}$alkyl, $C_{3-8}$cycloalkyl, 3-8-membered heterocycloalkyl, $C_{6-10}$aryl, $C_{7-16}$arylalkyl and 5-10-membered heteroaryl;

$R^3$ is a radical which is optionally substituted by one or more $R^e$ and/or $R^f$ and is selected from the group consisting of $C_{6-10}$aryl and 5-10-membered heteroaryl;

$R^4$ is a radical selected from the group consisting of $R^a$, $R^b$ and $R^a$ which is substituted by one or more, identical or different, $R^c$ and/or $R^b$;

each $R^a$ is, independently of each other, selected from the group consisting of $C_{1-6}$alkyl, $C_{3-8}$cycloalkyl, $C_{4-11}$cycloalkylalkyl, $C_{6-10}$aryl, $C_{7-16}$arylalkyl, 2-6-membered heteroalkyl, 3-8-membered heterocycloalkyl, 4-14-membered heterocycloalkylalkyl, 5-10-membered heteroaryl and 6-16-membered heteroarylalkyl;

each $R^b$ is a suitable radical and in each case selected, independently of each other, from the group consisting of =O, —$OR^c$, $C_{1-3}$haloalkyloxy, —$OCF_3$, =S, —$SR^c$, =$NR^c$, =$NOR^c$, —$NR^cR^c$, halogen, —$CF_3$, —CN, —NC, —OCN, —SCN, —NO, —$NO_2$, =$N_2$, —$N_3$, —$S(O)R^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)_2NR^cR^c$, —$C(O)R^c$, —$C(O)OR^c$, —$C(O)NR^cR^c$, —$C(O)N(R^g)NR^cR^c$, —$C(O)N(R^g)$ OR$^c$, —CN(R$^g$)NR$^c$R$^c$, —OC(O)R$^c$, —OC(O)OR$^c$, —OC(O)NR$^c$R$^c$, —OCN(R$^g$)NR$^c$R$^c$, —N(R$^g$)C(O)R$^c$, —N(R$^g$)C(O)R$^c$, —N(R$^g$)C(S)R$^c$, —N(R$^g$)S(O)$_2$R$^c$, —N(R$^g$)S(O)$_2$NR$^c$R$^c$, —N[S(O)$_2$]$_2$R$^c$, —N(R$^g$)C(O) OR$^c$, —N(R$^g$)C(O)NR$^c$R$^c$, and —N(R$^g$)CN(R$^g$)NR$^c$R$^c$;

each R$^c$ is, independently of each other, hydrogen or a radical which is optionally substituted by one or more, identical or different, R$^d$ and/or R$^e$ and which is selected from the group consisting of C$_{1-6}$alkyl, C$_{3-8}$cycloalkyl, C$_{4-11}$cycloalkylalkyl, C$_{6-10}$aryl, C$_{7-16}$arylalkyl, 2-6-membered heteroalkyl, 3-8-membered heterocycloalkyl, 4-14-membered heterocycloalkylalkyl, 5-10-membered heteroaryl and 6-16-membered heteroarylalkyl, each R$^d$ is, independently of each other, hydrogen or a radical which is optionally substituted by one or more, identical or different, R$^e$ and/or R$^f$ and which is selected from the group consisting of C$_{1-6}$alkyl, C$_{3-8}$cycloalkyl, C$_{4-11}$cycloalkylalkyl, C$_{6-10}$aryl, C$_{7-16}$arylalkyl, 2-6-membered heteroalkyl, 3-8-membered heterocycloalkyl, 4-14-membered heterocycloalkylalkyl, 5-10-membered heteroaryl and 6-16-membered heteroarylalkyl, each R$^e$ is a suitable radical and in each case selected, independently of each other, from the group consisting of =O, —OR$^f$, C$_{1-3}$haloalkyloxy, —OCF$_3$, =S, —SR$^f$, =NR$^f$, =NOR$^f$, —NR$^f$R$^f$, halogen, —CF3, —CN, —NC, —OCN, —SCN, —NO, —NO$_2$, =N$_2$, —N$_3$, —S(O)R$^f$, —S(O)$_2$R$^f$, —S(O)$_2$OR$^f$, —S(O)NR$^f$R$^f$, —S(O)$_2$NR$^f$R$^f$, —OS(O)R$^f$, —OS(O)$_2$R$^f$, —OS(O)$_2$OR$^f$, —OS(O)$_2$NR$^f$R$^f$, —C(O)R$^f$, —C(O)OR$^f$, —C(O)NR$^f$R$^f$, —CN(R$^g$)NR$^f$R$^f$, —OC(O)R$^f$, —OC(O)OR$^f$, —OC(O)NR$^f$R$^f$, —OCN(R$^g$)NR$^f$R$^f$, —N(R$^g$)C(O)R$^f$, —N(R$^g$)C(S)R$^f$, —N(R$^g$)S(O)$_2$R$^f$, —N(R$^g$)C(O)OR$^f$, —N(R$^g$)C(O)NR$^f$R$^f$, and —N(R$^g$)CN(R$^g$)NR$^f$R$^f$;

each R$^f$ is, independently of each other, hydrogen or a radical which is optionally substituted by one or more, identical or different, R$^g$ and is selected from the group consisting of C$_{1-6}$alkyl, C$_{3-8}$cycloalkyl, C$_{4-11}$cycloalkylalkyl, C$_{6-10}$aryl, C$_{7-16}$arylalkyl, 2-6-membered heteroalkyl, 3-8-membered heterocycloalkyl, 4-14-membered heterocycloalkylalkyl, 5-10-membered heteroaryl and 6-16-membered heteroarylalkyl, each R$^g$ is, independently of each other, hydrogen, C$_{1-6}$alkyl, C$_{3-8}$cycloalkyl, C$_{4-11}$cycloalkylalkyl, C$_{6-10}$aryl, C$_{7-16}$arylalkyl, 2-6-membered heteroalkyl, 3-8-membered heterocycloalkyl, 4-14-membered heterocycloalkylalkyl, 5-10-membered heteroaryl and 6-16-membered heteroarylalkyl, or a pharmaceutically acceptable acid addition salt thereof.

2. The compound according to claim 1, wherein R$^3$ is a radical selected from the group consisting of phenyl, furyl, pyridyl, pyrimidinyl and pyrazinyl, optionally substituted by one or more R$^4$.

3. The compound according to claim 2, wherein R$^3$ is pyridyl.

4. The compound according to claim 1, wherein R$^1$ is —NHC(O)R$^c$.

5. The compound according to claim 4, wherein R$^1$ is —NHC(O)CH$_3$.

6. A pharmaceutical preparation which comprises one or more compounds of the formula (1) according to claim 1, in combination with customary auxiliary substances and/or carrier substances.

* * * * *